United States Patent
Pedersen et al.

(10) Patent No.: US 11,608,504 B2
(45) Date of Patent: Mar. 21, 2023

(54) NUCLEIC ACID CONSTRUCT FOR IN VITRO AND IN VIVO GENE EXPRESSION

(71) Applicant: GLYCOM A/S, Hørsholm (DK)

(72) Inventors: Margit Pedersen, Roskilde (DK); Manos Papadakis, Copenhagen (DK)

(73) Assignee: GLYCOM A/S, Hørsholm (DK)

( * ) Notice: Subject to any disclaimer, the term of this patent is extended or adjusted under 35 U.S.C. 154(b) by 79 days.

(21) Appl. No.: 16/956,092

(22) PCT Filed: Dec. 19, 2018

(86) PCT No.: PCT/IB2018/060355
§ 371 (c)(1),
(2) Date: Jun. 19, 2020

(87) PCT Pub. No.: WO2019/123324
PCT Pub. Date: Jun. 27, 2019

(65) Prior Publication Data
US 2021/0102216 A1    Apr. 8, 2021

(30) Foreign Application Priority Data

Dec. 21, 2017  (DK) .......................... PA 2017 00737
Apr. 18, 2018  (DK) .......................... PA 2018 00173
May 24, 2018  (DK) .......................... PA 2018 00231

(51) Int. Cl.
C12N 15/70    (2006.01)
C12N 15/113    (2010.01)
C12N 15/11    (2006.01)
C12N 15/67    (2006.01)

(52) U.S. Cl.
CPC .............. *C12N 15/70* (2013.01); *C12N 15/11* (2013.01); *C12N 15/113* (2013.01); *C12N 15/67* (2013.01); *C12Q 2525/143* (2013.01)

(58) Field of Classification Search
None
See application file for complete search history.

(56) References Cited

U.S. PATENT DOCUMENTS

2016/0279175 A1    9/2016    Kaznessis et al.

FOREIGN PATENT DOCUMENTS

| EP | 0424117 A1 | 4/1991 |
| EP | 1016712 A2 | 5/2000 |
| EP | 2298880 A1 | 3/2011 |
| WO | 9640722 | 12/1996 |
| WO | 03089605 A2 | 10/2003 |
| WO | 2007013695 A1 | 2/2007 |
| WO | 2015188834 A1 | 12/2015 |
| WO | 2017152918 A1 | 9/2017 |
| WO | 2017182965 A1 | 10/2017 |

OTHER PUBLICATIONS

Wegener et al. Journal of Microbiological Methods 131 181-187 (Year: 2016).*
Zhu et al. Journal of Agricultural and Food Chemistry 69, 11342-11349 (Year: 2021).*
Beijer, L., et al., "The glpP and glpF genes of the glycerol regulon in Bacillus subtilis," Journal of General Microbiology, 1993, vol. 139, pp. 349-359.
Co-expression with pETDuet-1 (Duet Expression System) From Novagen. (Jan. 18, 2010). Biocompare. Retrieved on Sep. 18, 2020, from https://www.biocompare.com/Product-Reviews/40993-Co-expression-with-pETDuet-1-Duet-Expression-System-From-Novagen/.
Datsenko, K.A., et al., "One-step inactivation of chromosomal genes in *Escherichia coli* K-12 using PCR products," PNAS, 2000, vol. 97(12), pp. 6640-6645.
Diaz Ricci, J.C., et al., "Plasmid Effects on Escherichia coli Metabolism," Critical Reviews in Biotechnology,, 2000, vol. 20(2), pp. 79-108.
Drouillard, S., et al., "Efficient synthesis of 60-sialyllactose, 6,60-disialyllactose, and 60-KDO-lactose by metabolically engineered *E. coli* expressing a multifunctional sialyltransferase from the Photobacterium sp. JT-ISH-224," Carbohydrate Research, 2010, vol. 345, pp. 1394-1399.
Drouillard, S., et al., "Large-Scale Synthesis of H-Antigen Oligosaccharides by Expressing Helicobacter pylori a1,2-Fucosyltransferase in Metabolically Engineered *Escherichia coli* Cells," Angew. Chem. Int. Ed., 2006, vol. 45, pp. 1778-1780.
Fierfort, N., et al., "Genetic engineering of *Escherichia coli* for the economical production of sialylated oligosaccharides," Journal of Biotechnology, 2008, vol. 134, pp. 261-265.
Francia, M.V., et al., "Gene Integration in the *Escherichia coli* Chromosome Mediated by Tn21 Integrase (Int21)," Journal of Bacteriology, 1996, vol. 178(3), pp. 894-898.
Gebus, C., et al., "Synthesis of a-galactosyl epitopes by metabolically engineered *Escherichia coli*," Carbohydrate Research, 2012, vol. 361, pp. 83-90.
Hannig, G. et al., "Strategies for optimizing heterologous protein expression in *Escherichia coli*," Trends in Biotechnology, 1998, vol. 16, pp. 54-60.
Herring, C.D., et al., "Gene replacement without selection: regulated suppression of amber mutations in *Escherichia coli*," Gne, 2003, vol. 331, pp. 153-163.
Hoffmann, J., et al., "Functional Characterization of the Mannitol Promoter of Pseudomonas fluorescens DSM 50106 and Its Application for a Mannitol-Inducible Expression System for Pseudomonas putida KT2440," PLOS One, 2015, vol. 10(7), 22 pages. DOI: 10.1371/journal.pone.0133248.
Juhas, M., et al., "*Escherichia coli* Flagellar Genes as Target Sites for Integration and Expression of Genetic Circuits," PLOS One, 2014, vol. 9(10), 7 pages.

(Continued)

*Primary Examiner* — Brian Whiteman
(74) *Attorney, Agent, or Firm* — Neal, Gerber & Eisenberg LLP

(57) ABSTRACT

The present invention relates to the field of recombining production of biological molecules in host cells. The invention provides nucleic acid constructs that allow to modify expression of a desired gene using both in vitro and in vivo gene expression systems. The constructs can advantageously be used to produce a variety of biological molecules recombinantly in industrial scales, e.g. human milk oligosaccharides (HMO).

20 Claims, 17 Drawing Sheets
Specification includes a Sequence Listing.

(56) References Cited

OTHER PUBLICATIONS

Juhas, M., et al., "Flagellar region 3b supports strong expression of integrated DNA and the highest chromosomal integration efficiency of the *Escherichia coli* flagellar regions," Microbial Biotechnology, 2015, vol. 8, pp. 726-738.
Larson, T.J., et al., "Purification and Characterization of the Repressor for the sn-Glycerol 3-Phosphate Regulon of *Escherichia coli* K12," The Journal of Biological Chemistry, 1987, vol. 262(33), pp. 15869-15874.
Makrides, S.C., "Strategies for Achieving High-Level Expression of Genes in *Escherichia coli*," Microbiological Reviews, 1996, vol. 60(3), pp. 512-538.
Martíez-Gómez, K., et al., "New insights into *Escherichia coli* metabolism: carbon scavenging, acetate metabolism and carbon recycling responses during growth on glycerol," Microbial Cell Factories, 2012, vol. 11, pp. 1-21.
Meynial-Salles, I., et al., "New Tool for Metabolic Pathway Engineering in *Escherichia coli*: One-Step Method To Modulate Expression of Chromosomal Genes," Applied and Environmental Microbiology, 2005, vol. 71(4), pp. 2140-2144.
Murphy, K.C., "Use of Bacteriophage λ Recombination Functions To Promote Gene Replacement in *Escherichia coli*," Journal of Bacteriology, 1998, vol. 180(8), pp. 2063-2071.
Muyrers, J.P.P., et al., "Point mutation of bacterial artificial chromosomes by ET recombination," EMBO Reports, 2000, vol. 1(3), pp. 239-243.
Olson, P., et al., "High-Level Expression of Eukaryotic Polypeptides from Bacterial Chromosomes," Protein Expression and Purification, 1998, vol. 14, pp. 160-166.
Priem, B., et al., "A new fermentation process allows large-scale production of human oligosaccharides by metabolically engineered bacteria," Glycobiology, vol. 12(4), pp. 235-240.
Sabri, S., et al., "Knock-in/Knock-out (KIKO) vectors for rapid integration of large DNA sequences, including whole metabolic pathways, onto the *Escherichia coli* chromosome at well-characterised loci," Microbial Cell Factories, 2013, vol. 12, pp. 1-14.
Sanchez-Romero, J., et al. (1999). Genetic engineering of nonpathogenic Pseudomonas strains as biocatalysts for industrial and environmental process. In A.L. Damain and J.E. Davies (Eds.). Manual of Industrial Microbiology and Biotechnology, 2nd ed. (pp. 460-474). Washington, D.C.: ASM Press.
Schweizer, H.P., "Vectors to express foreign genes and techniques to monitor gene expression in Pseudomonads," Current Opinion in Biotechnology, 2001, vol. 12, pp. 439-445.
Sevillano, L., et al., "New approaches to achieve high level enzyme production in Streptomyces lividans," Microbial Cell Factories, 2016, vol. 15, pp. 1-10.

Shimada, T., et al., "Novel Roles of cAMP Receptor Protein (CRP) in Regulation of Transport and Metabolism of Carbon Sources," PLOS One, 2011, vol. 6(6), 11 pages.
Slater R.J., et al. (2002). The Expression of Foreign DNA in Bacteria. In J.M. Walker and R. Rapley (Eds.). Molecular Biology and Biotechnology, 4th ed. (pp. 125-153). Cambridge, UK: The Royal Society of Chemistry.
Stevens, R.C., "Design of high-throughput methods of protein production for structural biology," Structure, 2000, vol. 8(9), pp. r177-r185.
Terpe, K., "Overview of bacterial expression systems for heterologous protein production: from molecular and biochemical fundamentals to commercial systems," Appl Microbiol Biotechnol, 2006, vol. 72, pp. 211-222.
Truniger, V., et al., "Molecular Analysis of the glpFKX Regions of *Escherichia coli* and Shigella flexneri," Journal of Bacteriology, 1992, vol. 174(21), pp. 6981-6991.
Vetcher, L., et al., "Rapid Engineering of the Geldanamycin Biosynthesis Pathway by Red/ET Recombination and Gene Complementation," Applied and Environmental Microbiology, 2005, vol. 71(4), pp. 1829-1835.
Waddell, C.S., et al., "Tn7 transposition: two transposition pathways directed by five Tn7-encoded genes," Genes & Development, 1988, vol. 2, pp. 137-149.
Weissenborn, D.L., et al., "Structure and Regulation of the glpFK Operon Encoding Glycerol Diffusion Facilitator and Glycerol Kinase of *Escherichia coli* K-12," The Journal of Biological Chemistry, 19962, vol. 267(9), pp. 6122-6131.
Wenzel, S.C., "Heterologous Expression of a Myxobacterial Natural Products Assembly Line in Pseudomonads via Red/ET Recombineering," Chemistry & Biology, 2005, vol. 12, pp. 349-356.
Yang, B., et al., "Multiple promoters are responsible for transcription of the glpEGR operon of *Escherichia coli* K-12," Biochimica et Biophysica Acta, 1998, vol. 1396, pp. 114-126.
Zhang, Y., et al., "A new logic for DNA engineering using recombination in *Escherichia coli*," Nature Genetics, 1998, vol. 20, pp. 123-128.
Zhang, Z., et al., "A Novel Mechanism of Transposon-Mediated Gene Activation," PLOS Genetics, 2009, vol. 5(10), 9 pages.
Zhao, N., et al., "Characterization of the Interaction of the glp Repressor of *Escherichia coli* K-12 with Single and Tandem glp Operator Variants," Journal of Bacteriology, 1994, vol. 176(8), pp. 2393-2397.
Chen, X., "Human Milk Oligosaccharides (HMOS): Structure, Function, and Enzyme-Catalyzed Synthesis," Advances in Carbohydrate Chemistry and Biochemistry, 2015, vol. 72, pp. 113-190.
Urashima, T. et al. (2011) Nutrition and Diet Research Progress: Milk Oligosaccharides. New York: Nova Science Publishers, Inc. 92 pages.
Larson, T.J., et al., "Interaction at a Distance between Multiple Operators Controls the Adjacent, Divergently Transcribed glpTQ-glpACB Operons of *Escherichia coli* K-12," The Journal of Biological Chemistry, 1992, vol. 267(9), pp. 6114-6121.

\* cited by examiner

Variants of SEQ ID NO: 12 comprising a modification in the -10 box

| Strain | Promoter | Fragment of the DNA sequence comprising a modification |
|---|---|---|
| | | -35　　　　　　　　　　　　　　　　-10　　　　+1 |
| MAP808 | PglpF (SEQ ID NO: 12) | 5'-TTCTCGTTTTTGCTCGTTAACGATAAGTTTACAGCA-3' |
| MAP1010-9 | PglpF_9 (SEQ ID NO: 23) | 5'------------------------TTAA--------3' |
| MAP1010-11 | PglpF_11 (SEQ ID NO: 24) | 5'------------------------C--AA--------3' |
| MAP1010-13 | PglpF_13 (SEQ ID NO: 25) | 5'------------------------TTCC--------3' |
| MAP1010-17 | PglpF_17 (SEQ ID NO: 26) | 5'------------------------TGA---------3' |
| MAP1010-19 | PglpF_19 (SEQ ID NO: 27) | 5'------------------------G-AGC-------3' |
| MAP1010-20 | PglpF_20 (SEQ ID NO: 30) | 5'------------------------C---A-------3' |

NUCLEIC ACID CONSTRUCT FOR IN VITRO AND IN VIVO GENE EXPRESSION

CROSS-REFERENCE TO RELATED APPLICATIONS

This is a national stage filing in accordance with 35 U.S.C. § 371 of PCT/IB2018/060355, filed Dec. 19, 2018, which claims the benefit of the priority of Denmark Patent Application Nos. PA 2017 00737, filed Dec. 21, 2017, PA 2018 00173, filed Apr. 18, 2018, and PA 2018 00231, filed May 24, 2018, the contents of all of which are incorporated herein by reference.

SEQUENCE LISTING

This instant application contains a Sequence Listing which has been submitted in PDF format via EFS-Web and is hereby incorporated by reference in its entirety. Said PDF copy, created on Jun. 19, 2020, is named 029037-8040_Sequence_Listing.pdf, and is 79,251 bytes in size.

FIELD OF THE INVENTION

The present invention relates to the field of recombining production of biological molecules in host cells. The invention provides nucleic acid constructs that allow to modify expression of a desired gene using both in vitro and in vivo gene expression systems. The constructs can advantageously be used to produce a variety of biological molecules recombinantly in industrial scales, e.g. human milk oligosaccharides (HMO).

BACKGROUND OF INVENTION

The commercial importance of bacterial cells to produce recombining molecules is increasing. Currently, production of recombining proteins in bacterial hosts, in particular *E. coli*, mostly uses plasmid-borne expression systems. Since these systems provide high gene dosage and are well established, they have become widely accepted, also because the available cloning protocols are simple to handle. However, usage of plasmid-based expression systems, especially on a manufacturing scale has a bundle of downsides as well.

The plasmid-borne prokaryotic expression systems are typically characterized by high plasmid copy numbers, such as up to several hundred per cell. Expression plasmids usually carry the gene of interest under the control of a promoter, an origin of replication (ori) and a marker gene for selection of plasmid-carrying clones. In addition, coding or non-coding or non-functional backbone sequences are frequently present on said plasmids (i.e. vectors). The presence of plasmids and the corresponding replication mechanism alter the metabolism of the host cell (Diaz-Rizzi and Hernandez, (2000) *Crit Rev Biotechnol;* 20(2):79-108) and impose a high metabolic burden on the cells, thereby limiting their resources for recombining protein production. In addition, the application of strong promoters in combination with high gene dosage triggers a rate of recombining protein formation that is usually too high for the host cell to cope with and may therefore lead to a quick and irreversible breakdown of the cell metabolism. Consequently, the host cell's potential cannot be fully exploited in plasmid-based systems, resulting in low yield and quality of the recombining protein. Thus, one of the major drawbacks of plasmid-based expression systems may be attributed to the increased demand for nutrients and energy that is required for plasmid replication and maintenance.

Another typical phenomenon in plasmid-based systems is the change of plasmid copy number in the course of cultivation. Recombinant protein production is accompanied, at high expression rates, with starvation and cellular stress that lead to increased pools of uncharged tRNAs. This leads to an interference with the control mechanism of plasmid copy number (PCN). Consequently, PCN increases rapidly and causes a breakdown of the cultivation process (so-called "run-away effect").

Segregational instability, (i.e. the formation of plasmid free host cells) and structural instability (i.e. mutations in plasmid sequence) are further problems often seen in plasmid-based systems. During cell division, cells may lose the plasmid and, consequently, also the gene of interest. Such loss of plasmid depends on several external factors and increases with the number of cell divisions (generations). This means that plasmid-based fermentations are limited with regard to the number of generations or cell doublings.

Overall, due to these properties of plasmid-based expression systems, there is a limited yield of recombining protein and a reduced controllability of process operation and process economics.

In the search of an efficient alternative to plasmid-based expression, genome-based expression WO 1996/40722 describes a method that makes use of integration of a circular vector (so-called "circular chromosomal transfer DNA", CTD) including a selectable marker into the bacterial chromosome (i.e. at the attB site of *E. coli*). In that method, by using duplicate DNA sequences flanking the selection marker, amplification of the chromosomal gene dosage was achieved. Thereby, the obtained chromosomal gene dosage was approximately 15-40 copies per cell, which is similar to those achieved by commonly used plasmid vectors. Cultivation of clones containing chromosomal transfer DNA integrated into the bacterial genome resulted in levels of recombining proteins similar to those obtained by plasmid-based systems (Olson et al., 1998). This method requires in vitro ligation of CTD and is, regarding integration, limited to the attB site.

The genome-based expression systems seem to have a great potential to ensure stable and selection-marker-free expression of recombining genes. However, often expression of a recombining gene on a manufacturing scale is achievable only by increasing the gene dosage in the chromosome to the plasmid level, as a single copy of the gene is not able to provide expression on a manufacturing scale. Further, the selection of an integration site is a challenge, and the regulation of expression is often complex and/or not suitable for industrial production. Thus, there is not a simple and effective genome-based bacterial expression system for industrial production of recombining polypeptides.

One approach to overcome the problem of insufficient level of production and complex regulation of genome-based bacterial expression of heterologous polypeptides is the use of strong inducible promoters for controlling the transcription of integrated recombining genes. A number of different inducible promoters have been described. For example, promoters induced by high temperatures such as $\lambda P_R$ and $\lambda P_L$, tryptophan starvation such as trp, 1-arabinose such as araBAD, mannitol such as mtsE, phosphate starvation such as phoA, nalidixic acid such as recA, osmolarity such as proU, glucose starvation such as cst-1, tetracycline such as tetA, pH such as cadA, anaerobic conditions such as nar, T4 infection such as T4 gene32, alkyl- or halo-benzoates such as Pm, alkyl- or halo-toluenes such as Pu, salicylates such as Psal, and oxygen such as VHb, have all been examined as alternatives to IPTG inducible promoters (for the reference see, e.g., Makrides, S. C. (1996) Microbiol. Rev. 60, 512-538; Hannig G. & Makrides, S. C. (1998) TIBTECH 16, 54-60; Stevens, R. C. (2000) Structures 8, R177-R185; Hoffmann J & Altenbuchner J (2015) PLoS One, 10(7) e0133248; J. Sanchez-Romero & V. De Lorenzo, Genetic Engineering of Nonpathogenic *Pseudomonas* strains as Biocatalysts for Industrial and Environmental Processes, in Manual of Industrial Microbiology and Biotechnology (A. Demain & J. Davies, eds.) pp. 460-74 (1999) (ASM Press, Washington, D.C.); H. Schweizer, Vectors to express foreign genes and techniques to monitor gene expression for Pseudomonads, Current Opinion in Biotechnology, 12:439-445 (2001); and R. Slater & R. Williams, The Expression of Foreign DNA in Bacteria, in Molecular Biology and Biotechnology (J. Walker & R. Rapley, eds.) pp. 125-54 (2000) (The Royal Society of Chemistry, Cambridge, UK). However, there is a number of problems with these inducible promoters, such as high temperature induction that is harmful to cells and, in time, may not be practical for large scale fermentation due to equipment limitations; oxygen manipulation may affect the overall dynamics of the cell growth density aspects of the fermentation, reducing ideal conditions; the use of toluenes or other similar types of potentially toxic chemicals may require further purification to ensure that these compounds are not present in the final product; and pH may affect the ability of the peptide of interest to correctly fold or be solubilized in the host, making purification more costly and difficult, makes the plasmid-borne expression systems still to be the preferred choice for industrial production.

The carbon source regulation of promoter activity is probably the most attractive option for controlling expression of the target polypeptide in industrial settings. There are several reasons for this, e.g., a more efficient utilization of a carbon source and the reduction of extended metabolic stresses on the host cell. However, at present the choice of such promoters is rather limited, and most of them have been adopted for plasmid-borne expression (Terpe K. Appl Microbiol Biotechnol (2006) 72:211-222). Still, the genome of a bacterial cell, e.g. *E. coli*, contains thousands of promoters, and many of them are regulated by changes in the carbon source, allowing carbon availability in the environment to influence the expression pattern of genes under their control. It has been suggested that the global transcription regulator, cAMP-CRP, which is formed when glucose is limited, regulates a minimum of 378 promoters of a bacterial cell (Shimada T. et al., PloS One 6(6): e20081, (2011)), however, there is no data that would suggest which of these promoters are powerful ones that are capable to drive a genome-based stable controllable high-yield production of recombining polypeptides in industrial settings.

The respiratory metabolism of glycerol of *Escherichia coli* (*E.coli*) is controlled by 12 genes organized in 5 glp operons: glpFKX, glpABC, glpTQ, glpD, and PglpEGR. The glpFKX operon genes encode the glycerol diffusion facilitator, glycerol kinase, and a fructose 1,6-bisphosphatase. The glpABC operon gene encodes the anaerobic glycerol-P dehydrogenase subunits A, B and C. The glpTQ operon genes encode the glycerol-P carrier and glycerophosphodiesterase. The glpD gene encodes the aerobic glycerol-P-dehydrognase. The glpR gene encodes the GlpR transcriptional repressor, glpE a thiosulfate sulfurtransferase, and glpG encods a serine protease protein. Transcription of genes each of the glp operons is controlled by promoters, pglpFKX, pglpABC, pglpTQ, pglpD and pglpEGR, correspondingly, which activity is strictly catabolically regulated (Larson T J, J. et al, (1987); *Biol. Chem.* 262:15869-74 Zhao N et al (1994) *J Bacteriol,* 176: 2393-239). Recently, Selivano L., et al (*Microb Cell Fact* 15:28,(2016)), in a search for new promoters suitable for expression of recombining genes, tested a glp promoter, pglpQ, from Streptomyces coelicolor in a bacterial plasmid-borne expression system, however, this promoter demonstrated a rather low activity and therefore was disregarded as a promising candidate for industrial applications.

SUMMARY OF INVENTION

A first aspect of the invention relates to nucleic acid construct comprising a synthetic non-coding DNA sequence (i) that comprises a first DNA fragment and a second DNA fragment, wherein the first DNA fragment is a DNA sequence derived from the 5'-untranslated region (5'-UTR) of a glp gene of *Escherichia coli* and the second DNA fragment is DNA sequence CAAGGAGGAAACAGCT (SEQ ID NO: 10), or a variant of said sequence, and wherein the first fragment is located upstream of the second fragment. In particular, the inventions relate to nucleic acid construct comprising three operably linked DNA sequences: a promoter DNA sequence (ii), a synthetic non-coding DNA sequence comprising a ribosomal binding site (RBS) (i), and a coding DNA sequence (iii). Preferably, the first DNA fragment is derived from the 5'UTR DNA sequence of the glpF, glpA or glpD gene and comprises the first 5 to 65 consecutive nucleotides downstream of the transcription initiation site of the glpF, glpA or glpD promoters. In one preferred embodiment, the promoter DNA sequence (ii) corresponds to a DNA sequence of the promoter of a glp operon of *Escherichia coli* (*E. coli*), e.g. glpFKX, glpABC, glpTQ or glpD operons.

In a second aspect, the invention relates to a recombining cell, preferably a bacterial recombining cell, comprising a nucleic acid construct of the invention In a third aspect, the invention relates to an expression system comprising a construct of the invention or a recombining cell of the invention.

In a fourth aspect, the invention relates to a method for the production of one or more biological molecules, e.g. a protein, nucleic acid, oligosaccharide, etc, using a construct of the invention and/or recombining cell of the invention.

These and further aspects of the invention are described in detail below.

The data shows the level of activity of the expressed β-galactosidase in host cells. The activity was measured in Miller Units (U/OD/ml/min).

Figure 2A:
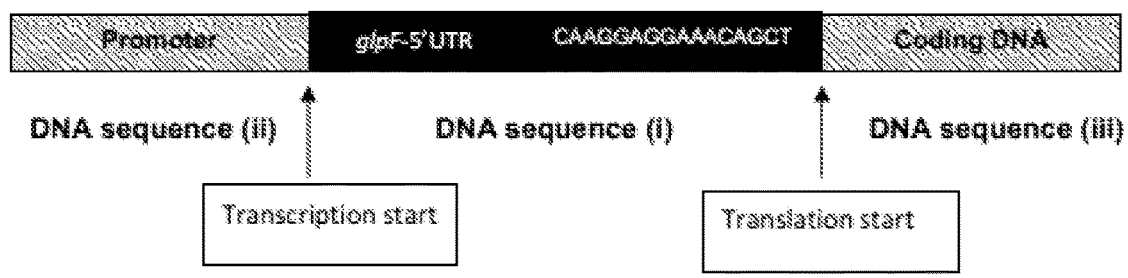
Figure 2B:
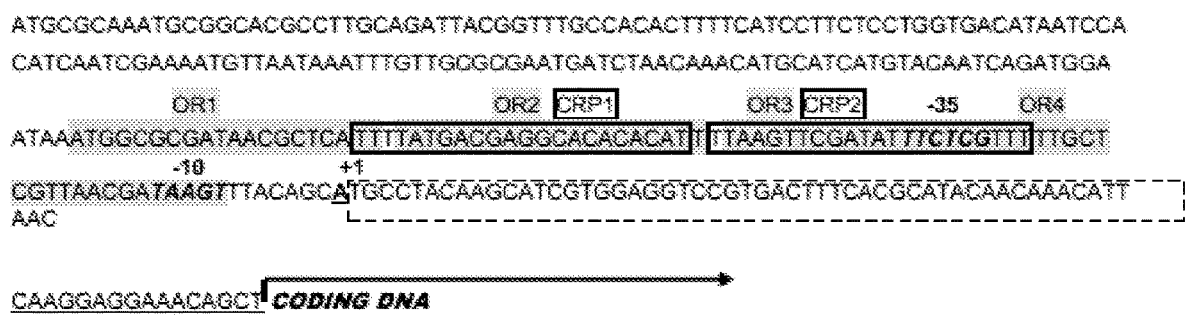

FIG. 2 presents (A) Schematic drawing of an embodiment of the nucleic acid construct of the invention;

(B) A nucleic acid construct of the invention comprising the glpF promoter DNA sequence (SEQ ID NO:54), the synthetic DNA (i) comprising SEQ ID NO:36 and SEQ ID:10. The following structural features are indicated the transcriptional start site at position +1 is shown in bold;

RNA polymerase binding site comprising the −10 and −35 boxes is shown in bold;

four operator sites, OR1, OR2, OR3 and OR4; for binding of the transcriptional repressor GlpR protein, are highlighted in grey;

two operator sites, CRP1 and CRP2, for binding of the transcriptional activator CRP protein, are shown in open boxes;

the synthetic DNA sequence including a 54-nucleotide fragment of the 5′UTR of the glpF gene (dash-line box) (SEQ ID NO:36) and SEQ ID NO:10 (underlined)

Figure 3:
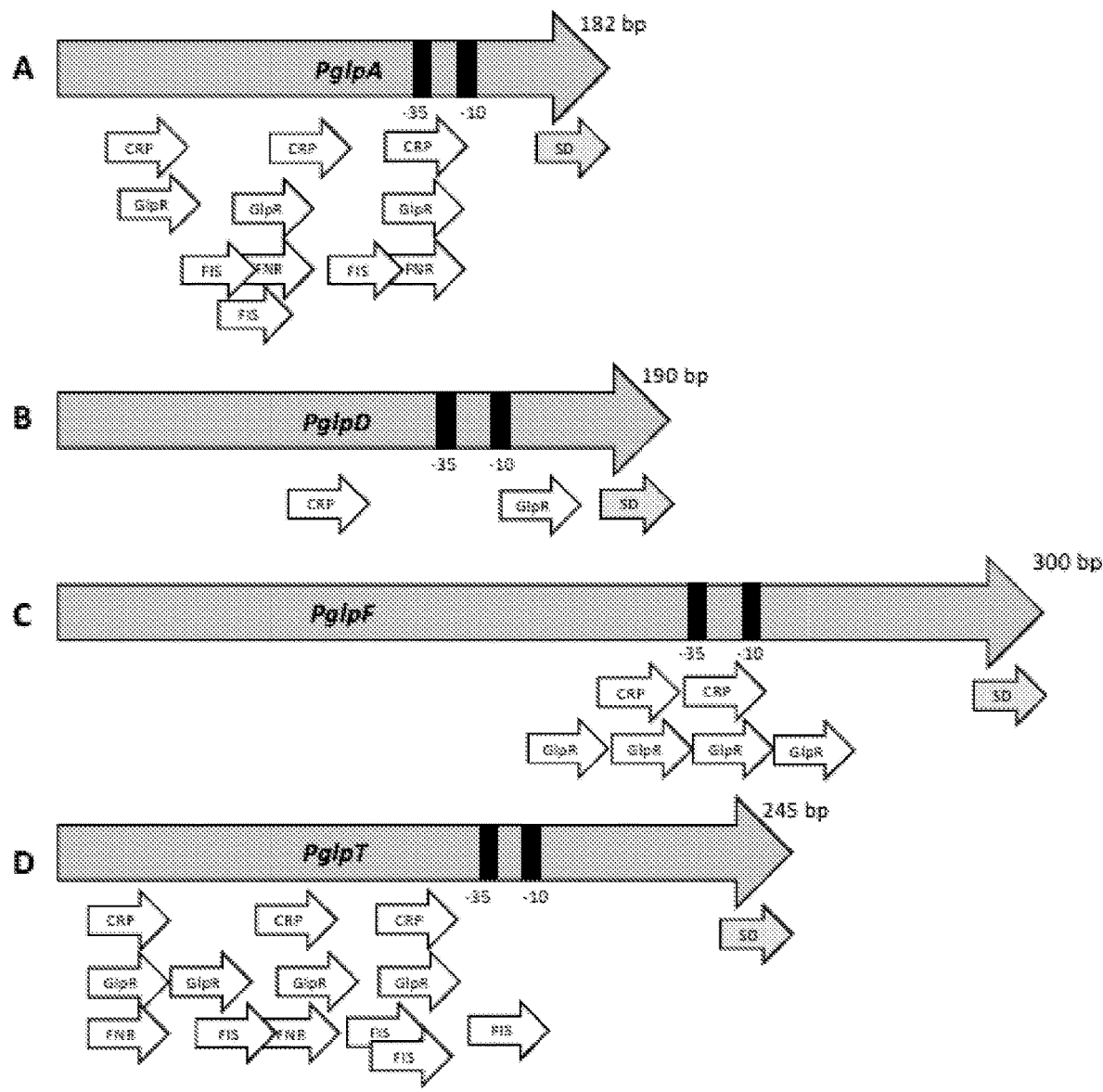

FIG. 3 schematically presents the structure of glp promoters:

(A) PglpA, (B) PglpD, (C) PglpF, and (D) PglpT.

The relative positions of the −35 and −10 regions recognized by the RNA polymerase are indicated with black boxes. The relative positions of the cAMP-CRP, GlpR, FNR, and FIS binding sites involved in transcriptional regulation of the promoter elements are indicated by small empty arrows; the relative positions of the 16-nucleotide fragment of the 5′UTR comprising a ribosomal binding site (SD) are indicated by small filled arrows.

Figure 4:
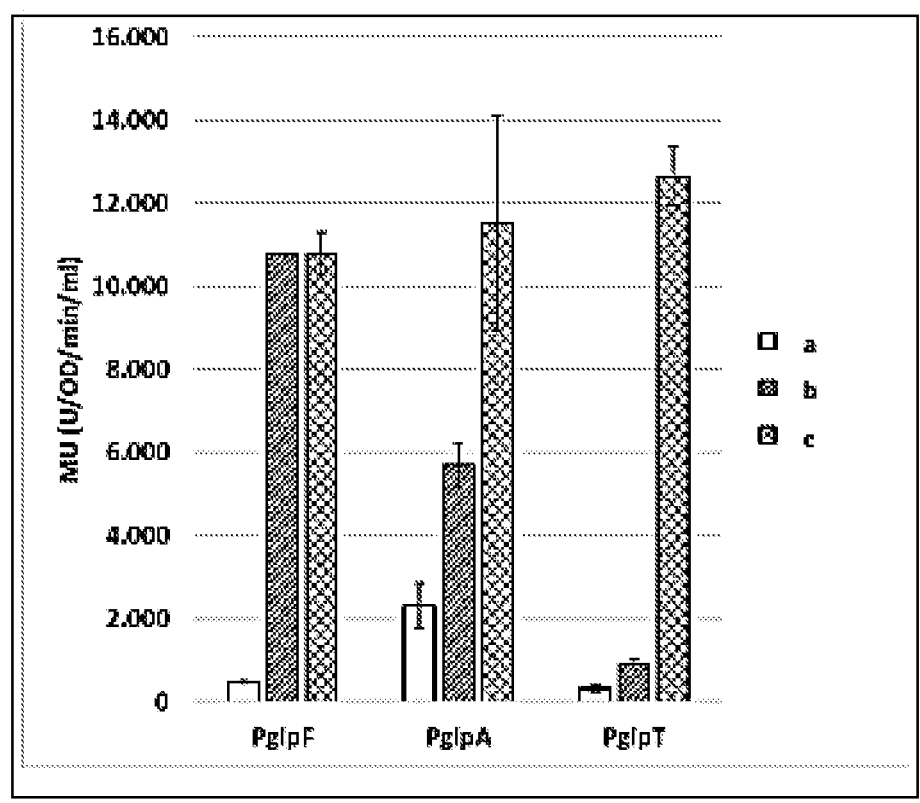

FIG. 4 presents data demonstrating the expression levels of the lacZgene expressed in *E. coli* from a single copy genome integrated expression cassette comprising (a) DNA fragments corresponding to the original glpF, glpA, or glpT promoter sequences and glpF, glpA, or glpT5′UTR DNA fragments comprising a (native) ribosomal binding site (RSB) (SEQ ID NOS: 57, 56 and 55, correspondingly) (open bars);

(b) DNA fragments comprising the original glpF, glpA, or glpT promoter sequences and fragments of the original glpF, glpA, or glpT 5′UTR DNA sequences that are lacking the native RBS (SEQ ID NOs: 1, 2 and 4, correspondingly) but are linked to SEQ ID NO:10 (hatched bars);

(c) DNA fragments comprising the original glpF, glpA, or glpT promoter sequences (SEQ ID NOs 54, 48, and 49, correspondingly) (each) operably linked to the 54-nucleotide DNA fragment of the glpF 5′UTR (SEQ ID NO: 36) and further linked to SEQ ID NO:10 (cross-hatched bars).

The data shows the level of activity of the expressed β-galactosidase in host cells. The activity is measured in Miller Units (U/OD/ml/min).

Figure 5:
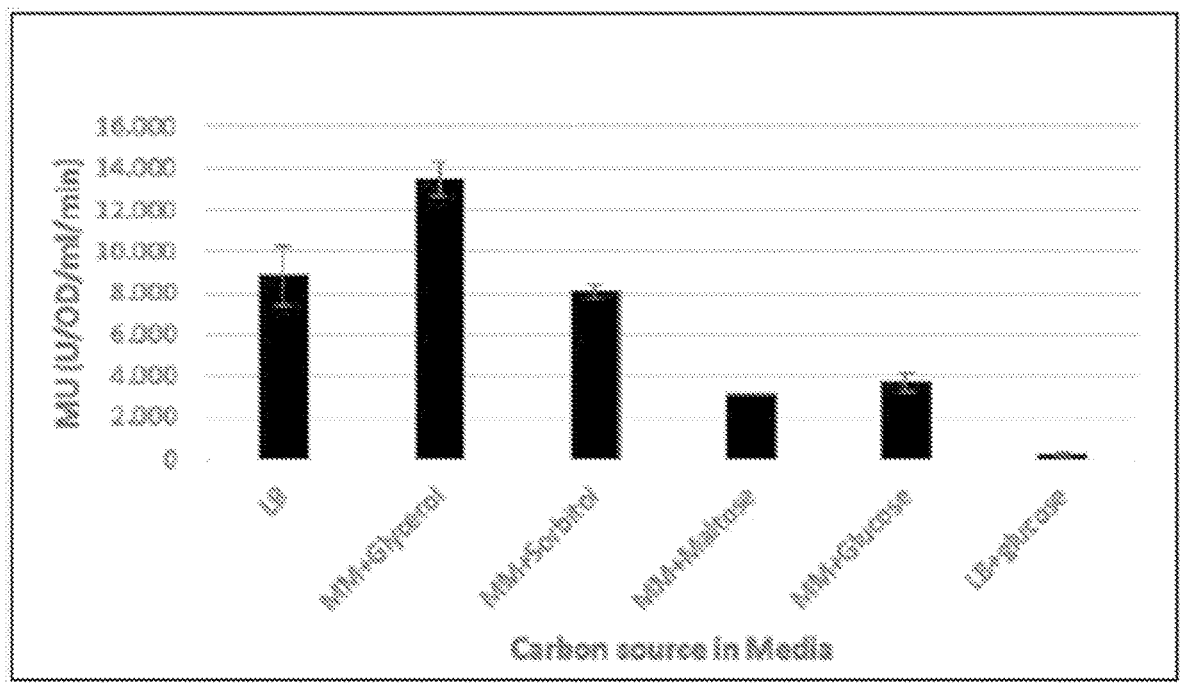

FIG. 5 presents data demonstrating catabolic repression of PglpF (SEQ ID NO: 12) when operably linked to the reporter gene lacZ integrated (in a single copy) into the genome of *E. coli*. The β-galactosidase activity was measured after growth in different media such as LB with or without glucose, Minimal Media containing glycerol, sorbitol, maltose or glucose. The β-galactosidase activity is measured in Miller Units (Units ONPG converted per OD600 per milliliter per minutes).

FIG. 6 demonstrates the expression level of lacZ from a single copy genome integrated expression cassette comprising either glpF or glpT promoter sequence (SEQ ID NO:54 or SEQ ID NO:50), the 54-nucleotide fragment of glpF-5′UTR (SEQ ID NO: 36) and SEQ ID NO: 10 or its variants: (A) variants of SEQ ID NO: 10; (B) β-galactosidase activity measurements (the reporter gene is expressed from constructs comprising 10 variants of SEQ ID NO:10 that have a modified RBS. The β-galactosidase activity is measured in Miller Units (Units ONPG converted per OD600 per milliliter per minutes).

FIG. 7 demonstrates the effect on the expression of lacZ (measured as the level of β-galactosidase activity) following modification of the −10 region of the glpF promoter. Seven different constructs comprising glpF promoter (SEQ ID NO:12) and its variants (PglpF_19, PglpF_20, PglpF_17, PglpF_11, PglpF_13, or PglpF_9) were operably linked to lacZand integrated (in a single copy) into the genome of *E. coli* and the activity of the reporter gene, lacZ, was evaluated as the level of β-galactosidase activity measured in Miller Units (Units ONPG converted per OD600 per milliliter per minutes). All constructs comprise SEQ ID NO: 10.

Figures 8A, 8B:
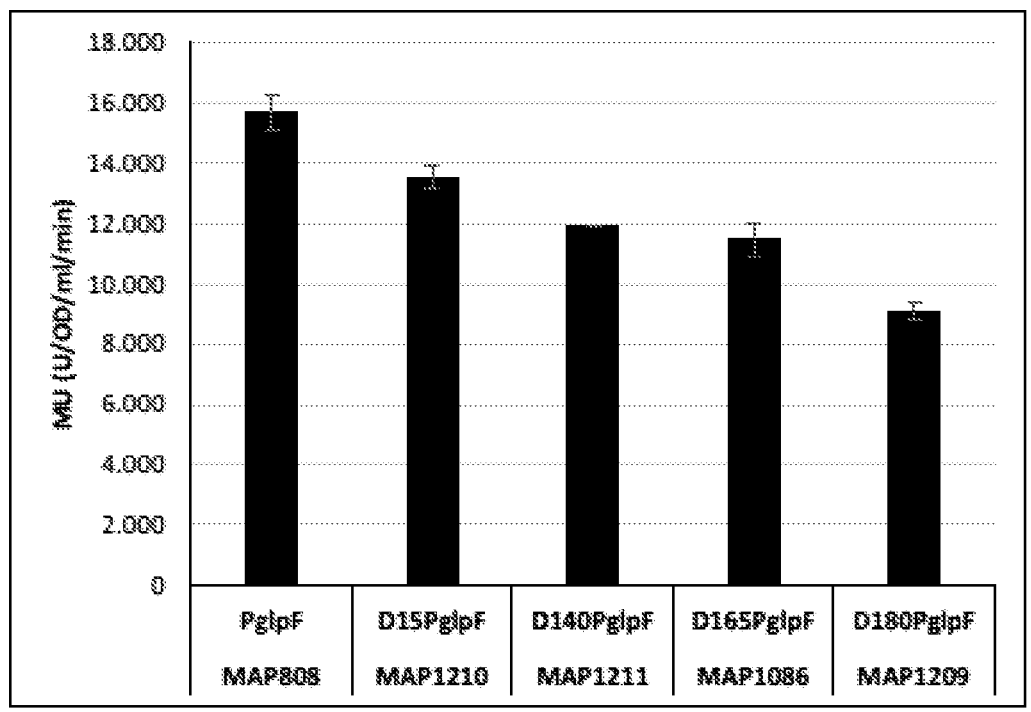

FIG. 8 demonstrates the effect of truncation of the 5′-end of the glpF sequence on the lacZ gene expression. The truncated variants of glpF promoter (SEQ ID NO:54) (the sequence of the promoter was truncated 15, 140, 165, or 180 base pairs from the 5′-end) are operably linked to lacZ and expressed from a single copy integrated into the genome of *E. coli*. All constructs comprise the 54-nucleotide fragment of glpF-5′UTR (SEQ ID NO: 36) and SEQ ID NO:10. The β-galactosidase activity is determined as Miller Units (Units ONPG converted per OD600 per milliliter per minutes).

Figure 9:
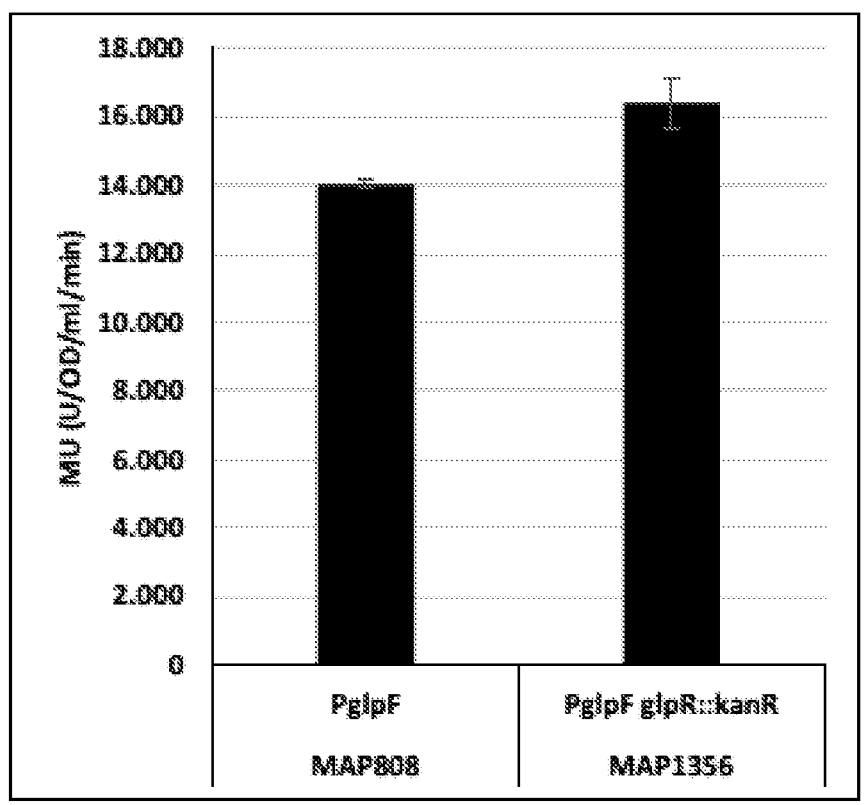

FIG. 9 demonstrates the effect on the level of β-galactosidase activity following disruption of the glpR gene in the host cell from a construct comprising lacZoperably linked to glpF promoter (SEQ ID NO: 54 linked to the 54-nucleotide fragment of glpF-5′UTR (SEQ ID NO: 36) and SEQ ID NO: 10. The β-galactosidase activity is measured in cells expressing the transcriptional repressor protein, GlpR, (i.e. comprising the native glpR gene) and in cells where the gene was disrupted by introducing kanR (i.e. in cells with low or no expression of GlpR). The β-galactosidase activity is determined as Miller Units (Units ONPG converted per OD600 per milliliter per minutes).

Figure 10A:
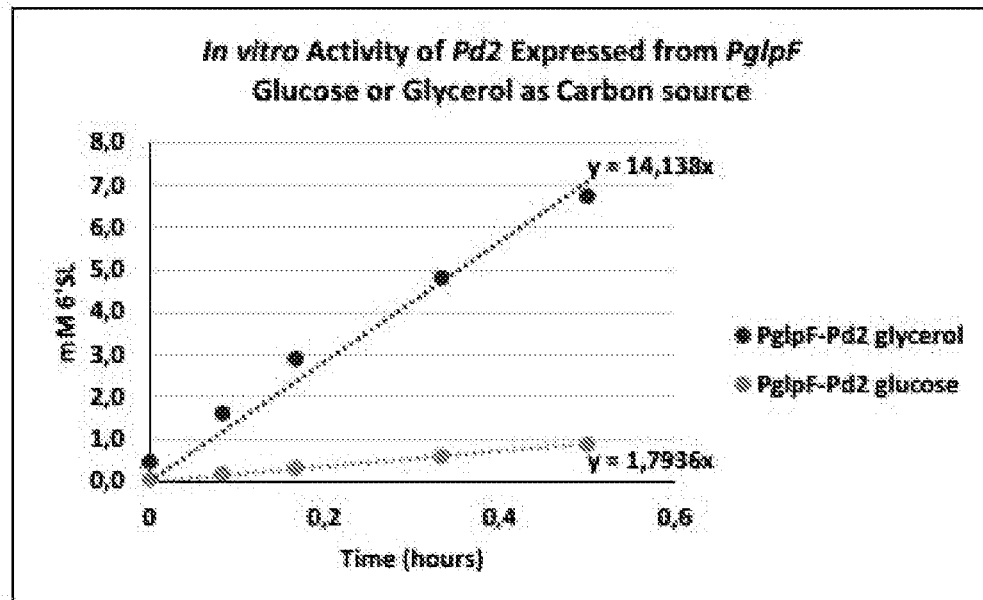
Figure 10B:
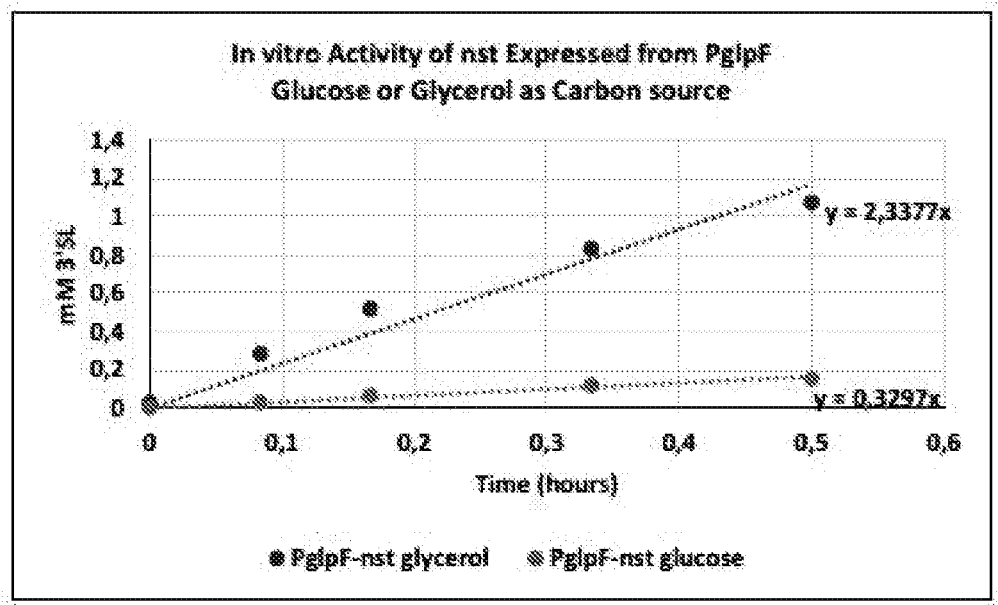

FIG. 10 demonstrate results of expression of heterologous genes in *E. coli* expressed from DNA constructs under either the lac promoter (Plac,; grey circles), or glpF promoter (PglpF; black circles), inserted as single copies into the genome of *E. coli*. All constructs comprise SEQ ID NO: 10 and the native RBS-lacking 5′UTR fragments of the corresponding genes.

(A) Production of 6′-sialyllactose (6′SL) evaluated from crude extracts of cells expressing α-2,6-sialyltransferase Pd2 (from *Photobacterium damselae* JT0160).

(B) Production of 3′-siallyllactose (3′SL) evaluated from crude extracts of cells expressing α-2,3-sialyltransferase NST (from *Neisseria meningitides* MC58).

The sialyltransferase activity is measured as production in mM per hour

Figure 11:
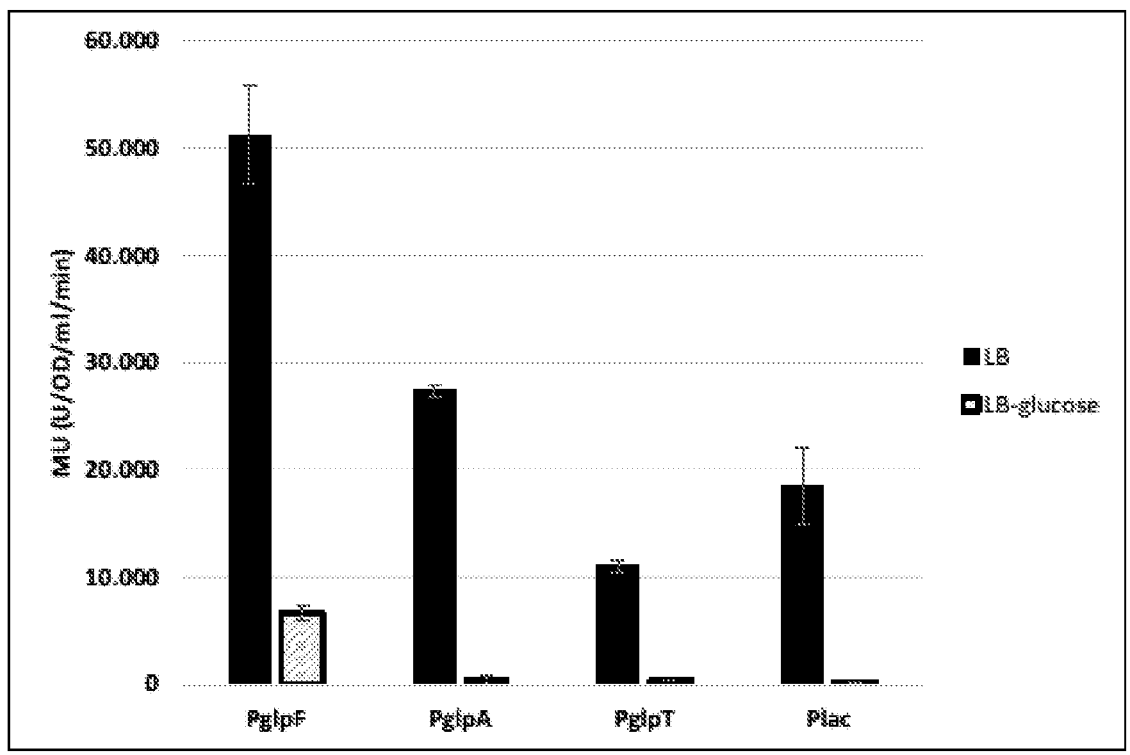

FIG. 11 demonstrates the levels of expression of lacZ under control of lac, glpF, glpA or glpT promoter from a multi-copy-number plasmid comprising a single copy of the corresponding expression cassette. The expression cassettes each comprises SEQ ID NO:10 and the native RBS-lacking 5′UTR fragments of the corresponding genes (i.e. glpF, glpA, glpT, or lacZ, respectively) The β-galactosidase activity is measured after growth in different media such as LB with or without glucose (shaded or filled bars, respectively) in Miller Units (Units ONPG converted per OD600 per milliliter per minutes).

FIG. 12 shows the results of production of LNnT in recombining *E. coli* expressing the heterologous genes galT and IgtA under the control of either the Plac or the PglpF promoter (both expression cassettes comprises SEQ ID NO:10 and the native RBS-lacking 5'UTR fragments of lacZ or glpF correspondingly). A) MDO1 expresses galT and IgtA from Plac of a high and medium copy number plasmid, respectively. MP1497 expresses IgtA from a single chromosomal gene copy using PglpF, and galT from a high number plasmid using Plac. MP1499 expresses galT from a single chromosomal gene copy using PglpF, and IgtA from a medium copy number plasmid using Plac. B) MP2622 and MP166 expresses IgtA and galT from a single or three chromosomally integrated gene copies, respectively, using Plac; MP1825 expresses IgtA and galT from single chromosomal copies using PglpF.

FIG. 13 shows the results of production of LNT in recombining *E. coli* expressing the heterologous genes galTK and IgtA under the control of either Plac or PglpF (both expression cassettes comprises SEQ ID NO:10 and the native RBS-lacking 5'UTR fragments of lacZ or glpF correspondingly). A) MDO15 expresses galTK and IgtA under the control of Plac of a high and medium copy number plasmid, respectively. MP1498 expresses IgtA from a single chromosomal integrated gene copy using PglpF, and galTK from a high copy number plasmid using Plac. MP1655 expresses galTK from two chromosomal gene copies using PglpF, and IgtA from a medium copy number plasmid using Plac. B) MP245 expresses 3 and 2 chromosomal integrated gene copies of IgtA and galTK, respectively, using Plac; MP1920 expresses IgtA and galTK from single chromosomal integrated gene copies using PglpF.

Figure 14:
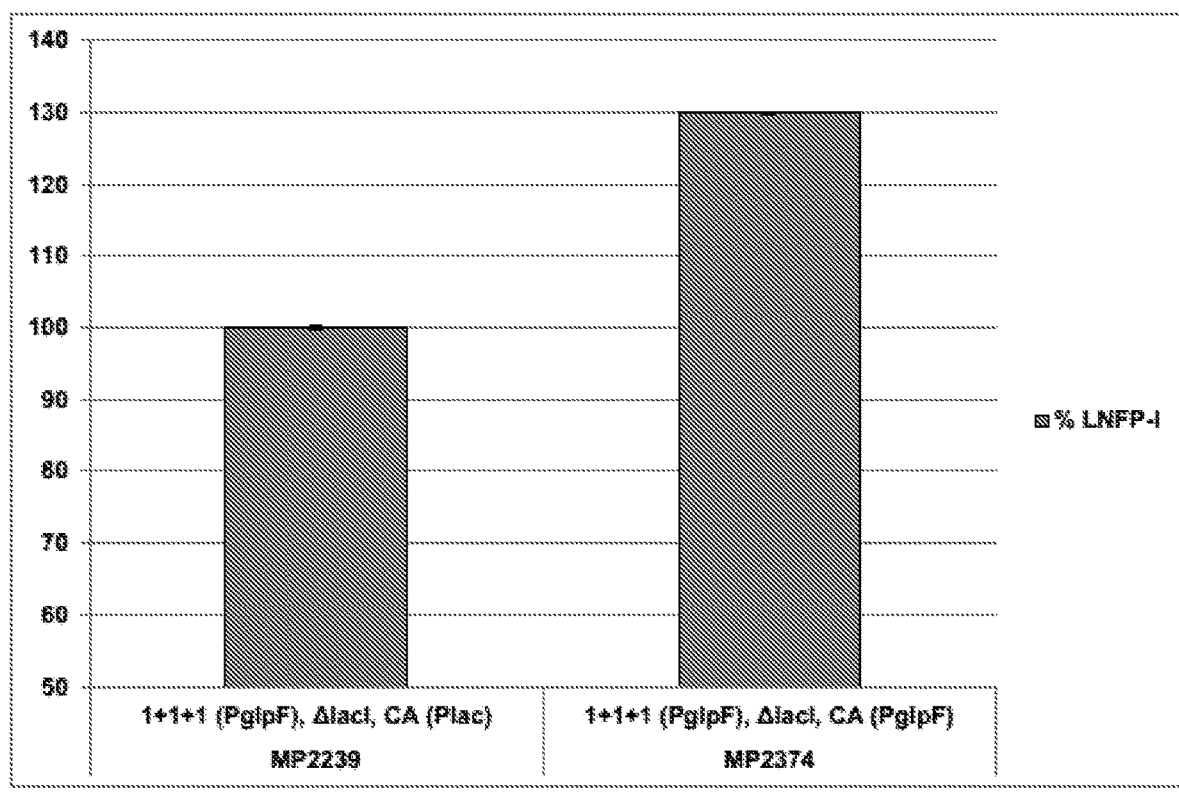

FIG. 14 shows the results of production of LNFP-I in recombining *E. coli* expressing the heterologous genes galTK, IgtA, and futC under the control of PglpF. MP2239 and MP2374 express IgtA, galTK, and futC, from single chromosomally integrated gene copies using PglpF. In addition, MP2374 contains an extra copy of the colonic acid genes gmd, wcaJ (fcl), wcaH (gmm), wcaI, cpsB (manC), and cpsG (manB), all expressed under the control of PglpF. The expression cassettes comprise SEQ ID NO:10 and the native RBS-lacking 5'UTR fragment glpF).

Figure 15:
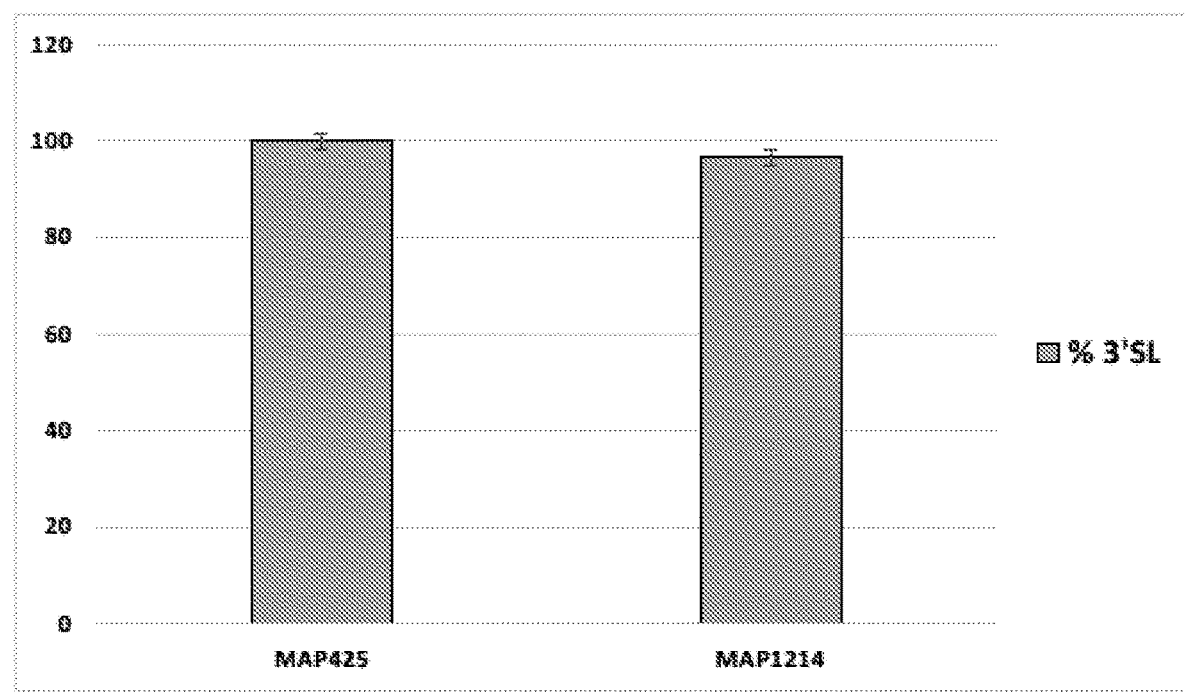

FIG. 15 shows the results of production of 3'SL in recombining *E. coli* expressing the heterologous genes nst, neuA, neuB, and neuC. MAP425 expresses 2 chromosomally integrated copies of nst as well as neuA, neuB, and neuC, from a high copy number plasmid using Plac. MAP1214 expresses nst, neuA, neuB, and neuC, from a single chromosomal gene copy using PglpF. The expression cassettes comprise SEQ ID NO:10 and the native RBS-lacking 5'UTR fragments of lacZ or glpF correspondingly.

Figure 16:
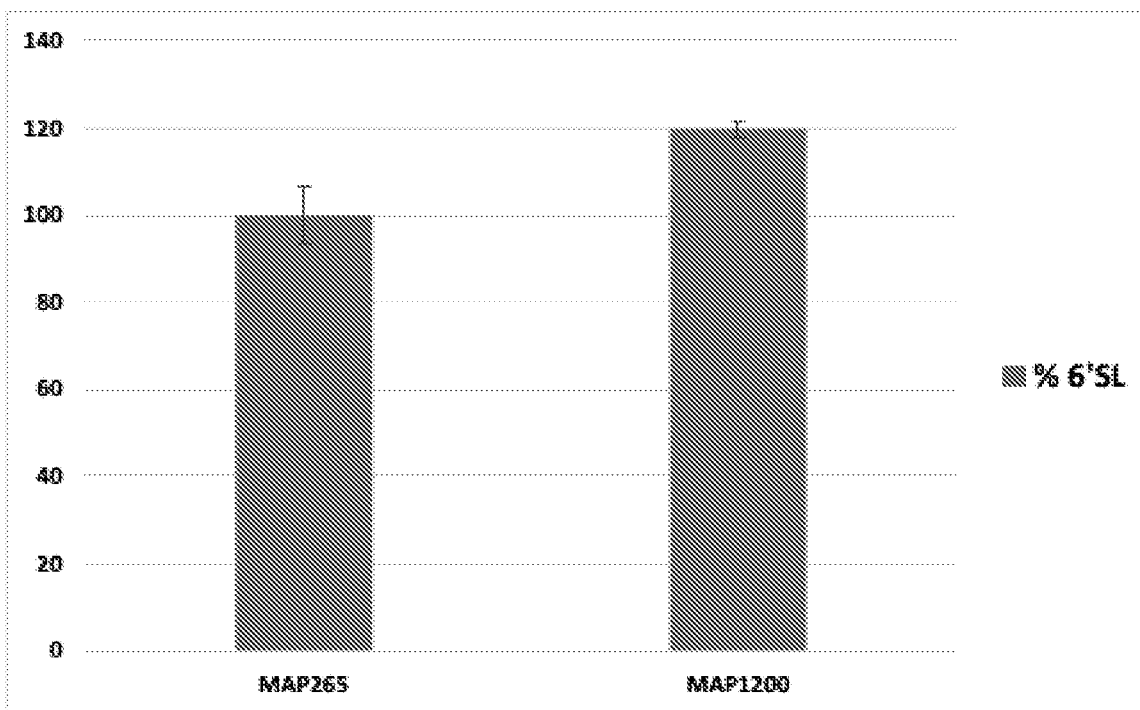

FIG. 16 shows the results of production of 6'SL in modified *E. coli* expressing the heterologous genes Pd2, neuA, neuB, and neuC. MAP265 expresses a single chromosomal copy of Pd2 as well as neuA, neuB, and neuC, from a high copy number plasmid using Plac. MAP1200 expresses Pd2, neuA, neuB, and neuC, from a single chromosomal gene copy using PglpF. The expression cassettes comprise SEQ ID NO:10 and the native RBS-lacking 5'UTR fragments of lacZ or glpF correspondingly.

Figure 17:
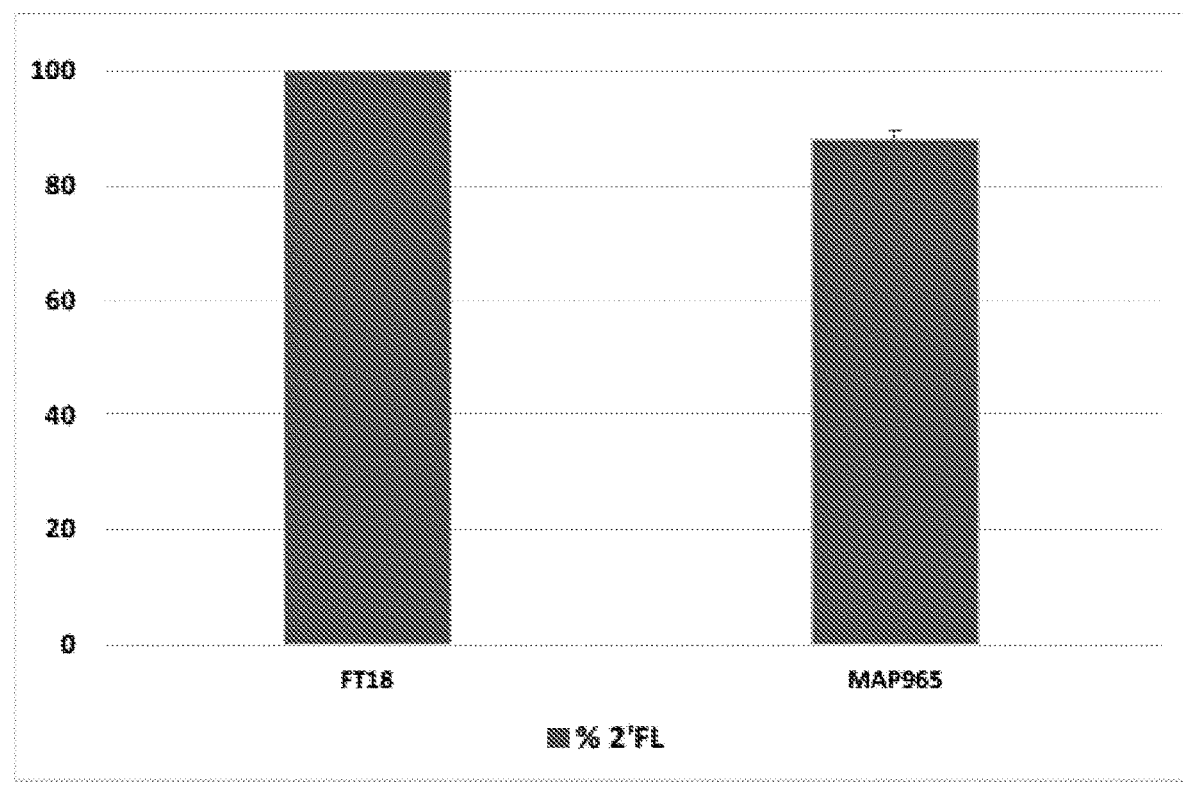

FIG. 17 shows the results production of 2'FL in recombining *E. coli* expressing the heterologous gene futC: strain FT18 contains two plasmids expressing futC and the colonic acid genes gmd, fcl, manC, and manB under control of Plac; strain MAP965 contains a single futC copy and the colonic acid genes: gmd, wcaJ (fcl), wcaH (gmm), wcaI, cpsB (manC), and cpsG (manB), which are expressed under the control of PglpF. The expression cassettes comprise SEQ ID NO:10 and the native RBS-lacking 5'UTR fragments of lacZ or glpF correspondingly.

DETAILED DESCRIPTION OF INVENTION

The present invention in general relates to DNA constructs and expression systems useful for recombining production of biological molecules. In particular, the present invention relates to recombining bacterial expression systems capable of providing stable and remarkably high expression of a gene that is operably linked to a promoter and a synthetic non-coding DNA sequence located upstream of the gene, wherein said synthetic DNA sequence (interchangeably termed herein "synthetic/artificial/recombining DNA sequence (i)") comprises a fragment of the 5'-untranslated leading DNA sequence (5'UTR DNA) of a glp gene of *Escherichia coli* (*E. coli*) and DNA sequence CAAGGAGGAAACAGCT (SEQ ID NO: 10), or a variant thereof. The sequence CAAGGAGGAAACAGCT (SEQ ID NO: 10) is an artificial DNA sequence that is originally derived from the 5'UTR of lacZ of *E. coli* and has been modified in the sequence of the ribosomal binding site (RBS). Previously, the sequence has been described for its capability to enhance expression of a reporter gene (lacZ) by about β-fold in a model gene expression system using a nucleic acid construct wherein this sequence was operably linked to an artificial promoter and to a 30-nucleotide DNA sequence that is capable of stabilizing mRNA. (Meynial-Salles I, et al (2005) *Appl Eviron Microbiol* 71:2140-2144; WO 03/089605). We surprisingly found that SEQ ID NO:10, or a variant thereof, when it is not linked to the described RNA stabilizing DNA sequence, is not capable of enhancing expression of the reporter gene (lacZ) from all randomly selected promoters tested, but only from a few of them. However, if SEQ ID NO:10 is linked to a fragment of the 5'UTR DNA of a glp gene, advantageously, the glpF, glpA, glpT, or glpD gene, expression of the reporter gene is greatly increased, and the level of expression of the gene is independent, or much less dependent, on the choice of the promoter, i.e. the strength of the promoter has less influence of the level of gene expression when the synthetic DNA sequence of invention is inserted between the promoter and the gene.

Accordingly, a first aspect of the invention relates to a synthetic non-coding DNA sequence (i) comprising a first DNA fragment and a second DNA fragment, wherein the first fragment is a fragment of the 5'UTR DNA of a glp gene, advantageously, the glpF, glpA, glpT, or glpD gene, and the second fragment is SEQ ID NO:10, or a variant thereof, and wherein the second fragment is located downstream of the first fragment (i.e. the second fragment is linked to the 3'-end of the first fragment). Advantageously, the synthetic non-coding DNA sequence (i) is a part of a nucleic acid construct wherein it is operably linked to a promoter DNA sequence (ii) and, optionally, to a coding DNA sequence (iii), and wherein said synthetic DNA sequence is located downstream of the promoter DNA sequence (ii) and, optionally, upstream of the coding DNA sequence (iii). The term "optionally" in the present context means that in some embodiments the invention relates to nucleic acid constructs that comprise a promoter DNA sequence (ii) and the synthetic DNA sequence (i), but not a coding DNA (iii). Still in other embodiments, the synthetic DNA sequence (i) may be operably linked to a coding DNA sequence (iii), and no promoter DNA is included in the construct. Yet in other embodiments, the construct may comprise the synthetic DNA sequence (i) and neither promoter DNA or coding DNA sequences. The nucleic acid constructs comprising the synthetic DNA sequence (i) can be integrated into the genome of a host cell upstream of a gene and downstream of the gene native promoter, e.g. replacing existing the native DNA sequence, or it can be inserted into the genomic DNA to substitute either/both promoter and/or the 5'UTR DNA sequences of a genomic gene of interest. The construct of the invention can also be used to modify expression of the gene of interest in a desired mode (i.e. to increase or decrease the gene expression) compared to natural expression of the gene controlled by native (not artificially modified) regulatory genomic DNA sequences. As mentioned, in one embodiment the construct, may comprise the artificial DNA sequence (i) only, i.e. no promoter or cording DNA sequences, as such construct can be inserted into the genome of a host cell downstream of a genomic promoter sequence and upstream of a gene/coding sequence (replacing an existing native sequence or an addition/extension to the existing sequence), and thereby to modify expression of the gene (increase or decrease) compared to its natural expression from the corresponding genomic promoter. Still in other embodiments, the construct of the invention may comprise operably linked a promoter DNA sequence (ii), the synthetic DNA sequence (i) and a coding DNA sequence (iii) encoding a heterologous or homologous (with respect to the host cell) biological molecule, wherein the synthetic DNA sequence is placed between the promoter DNA and the coding DNA sequences.

Unless otherwise specified, all technical and scientific terms used herein have the same meaning as commonly understood by one of ordinary skill in the art to which this invention belongs. Singleton et al. (1994) Dictionary of Microbiology and Molecular Biology, second edition, John Wiley and Sons (New York) provides one of skill with a general dictionary of many of the terms used in this invention. Although any methods and materials similar or equivalent to those described herein can be used in the practice or testing of the present invention, the preferred methods and materials are described. Most of the nomenclature and general laboratory procedures required in this application can be found in Sambrook et al., Molecular Cloning: A Laboratory Manual, Vol. 1-3, Cold Spring Harbor Laboratory, Cold Spring Harbor, N.Y. (2012); Wilson K. and Walker J., Principles and Techniques of Biochemistry and Molecular Biology (2010), Cambridge University Press; or in Maniatise et al., Molecular Cloning A laboratory Manual, Cold Spring Harbor Laboratory (2012); or in Ausubel et al., Current protocols in molecular biology, John Wiley and Sohns (2010). The manuals are hereinafter referred to as "Sambrook et al.", "*Wilson & Walker*", "Maniatise et al", "Ausubel et al", correspondingly.

If not otherwise specified, the terms defined throughout specification relate to all aspects and embodiments of the invention. All embodiments described in specification and working examples relate to all and any aspects of the invention.

As used herein, the term "nucleic acid" includes RNA, DNA and cDNA molecules. It is understood that, as a result of the degeneracy of the genetic code, a multitude of nucleotide sequences encoding a given protein may be produced. The term nucleic acid is used interchangeably with the term "polynucleotide". An "oligonucleotide" is a short chain nucleic acid molecule. "Primer" is an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification but is may alternatively be double stranded. If double stranded, the primer is first treated to separate its strands before being used to prepare extension products. Preferably, the primer is a deoxyribonucleotide. The primer must be sufficiently long to prime the synthesis of extension products in the presence of the inducing agent. The exact lengths of the primers will depend on many factors, including temperature, source of primer and the use of the method.

"Nucleic acid construct" means an artificially constructed segment of nucleic acid, in particular a DNA segment, which is intended to be 'transplanted' into a target cell, e.g. a bacterial cell, to modify expression of a gene of the genome or express a gene/coding DNA sequence which may be included in the construct In the context of the invention, the nucleic acid construct contains a recombining DNA sequence essentially consisting of, optionally, one, two, or three isolated DNA sequences: a synthetic non-coding DNA sequence(i) comprising a ribosomal binding site (RBS), a promoter DNA sequence (ii), and a coding DNA sequence (iii). In the embodiments relating to the construct comprising two or three of the latter sequence, the sequences are operably linked to each other in the construct. "Operably linked" is defined herein as a configuration in which control sequence, i.e. a promoter sequence, and/or a 5'UTR sequence, is appropriately placed at a position relative to a coding DNA sequence such that the control sequences direct the transcription of the coding sequence and translation of the mRNA into polypeptide sequence encoded by the coding DNA. In the embodiment where the construct comprises a coding DNA sequence, preferably, the coding DNA encodes at least one protein or RNA molecule that has an activity that is directly or indirectly involved in the production of one or more HMOs in the host cell ((i.e. the activity is essential or beneficial for the production of one or more HMOs). Non-limiting examples of such activities may be an enzymatic, gene expression regulatory, chaperone activity. Non-limiting examples of the coding DNA sequence (iii) are described below and in the working examples. The DNA construct of the invention is in some embodiments referred as expression cassette of the invention DNA constructs/expression cassettes of the invention in some embodiments may comprise more than one coding DNA sequence, which may encode different biological molecules. Preferably, the constructs (containing one or more coding DNA sequences (iii)) comprise a single copy of the promoter DNA sequence (ii) and a single copy of the synthetic DNA sequence (i). The DNA constructs of the invention may be inserted into a plasmid DNA/vector, transplanted into the target/host cell and expressed as plasmid- and/or chromosome-borne. The DNA constructs may be linear or circular. A linear or circular DNA construct integrated into the host bacterial genome or expression plasmid is interchangeably termed herein as "expression cassette", "expression cartridge" or "cartridge". In one embodiment, the cartridge is a linear DNA construct comprising three DMA sequences: a promoter (DNA sequence (ii)), a synthetic DNA sequence (i)) downstream the promoter, and a coding DNA sequence (sequence iii) encoding a biological molecule of interest. The construct may also comprise further sequences, e. g. a transcriptional terminator sequence, and two terminally flanking regions, which are homologous to a genomic region and which enable homologous recombination, and/or other sequences as described herein. The cartridge can be made by methods well-known known in the art, e.g. using standard methods described in Wilson & Walker. The use of a linear expression cartridge may provide the advantage that the genomic integration site can be freely chosen by the respective design of the flanking homologous regions of the cartridge. Thereby, integration of the linear expression cartridge allows for greater variability with regard to the genomic region. Linear cartridges are included in preferred embodiments of the invention.

By the term "ribosome binding site" (RBS) is meant a short nucleotide sequence usually comprising about 4-16 nucleobases that functions by positioning the ribosome on the mRNA molecule for translation of an encoded protein. A "modified ribosome binding" site is a ribosome binding site wherein one or more base pairs have been altered. According to the invention, the synthetic non-coding DNA sequence (i) comprises a RBS within the SEQ ID NO: 10, or a variant thereof. The variants of SEQ ID NO:12 in can be used in different embodiment e.g. for the purpose of modifying expression of a genomic DNA sequence of interest, as we show herein that some variants can enhance gene expression to a further extend compared to the expression achieved with use of SEQ ID NO:10, whereas other variants can decrease expression of a gene. Useful, but not limiting embodiments of DNA sequences that comprise an RBS can be found in Table 1 below and described through the specification of the invention.

For the purposes of this invention, a "promoter" or "promoter region" or "promoter element" is a nucleic acid sequence that is recognized and bound by a DNA dependent RNA polymerase during initiation of transcription. The promoter, together with other transcriptional and translational regulatory nucleic acid sequences (also termed "control sequences") is necessary to express a given gene or group of genes (an operon). In general, the transcriptional and translational regulatory sequences include, but are not limited to, promoter sequences, ribosomal binding sites, transcriptional start and stop sequences, translational start and stop sequences, and enhancer or activator sequences. The "transcription start site" means the first nucleotide to be transcribed and is designated +1. Nucleotides downstream of the start site are numbered +2, +3, +4 etc., and nucleotides in the 5' opposite (upstream) direction are numbered −1, −2, −3 etc. A promoter of the invention is an isolated DNA sequence. The term "isolated DNA sequence" means that the sequences is not an integrated fragment of the genomic DNA, but an artificial/cloned DNA fragment that is identical or homologous to a genomic DNA sequence; following this definition, the promoter DNA of the construct/expression cassette described herein is regarded as "derived" from the genomic DNA sequence comprised in the promoter region of a gene. The promoter DNA sequence of the construct of the invention can derive from a promoter region of any gene of the genome of a selected species, preferably, a promoter region of the genomic DNA of E. coli. According to the invention any promoter DNA sequence that is able to bind to an RNA polymerase and initiate transcription is suitable for practicing the invention. As mentioned, the nucleotide sequence of promoter DNA of the construct may be identical, or has a certain percent of identity, such as around 65-70% of identity, preferably at least 80% identity, preferably from around 90% to around 99,9% of identity with the nucleotide sequence of a fragment of the genomic DNA sequence, preferably, a bacterial genomic DNA sequence, that is regarded as the promoter region of a single gene or an operon, e. g. a glp operon or lac operon of E. coli. The terms "around","about" and "approximately" are used interchangeably and mean a 1-10% deviation of the indicated value, or a minor deviation that does not influence a relevant feature. By "operon" is meant a functioning unit of genomic DNA containing a cluster of genes under the control of a single promoter. By "glp operon" is meant a cluster of genes involved in the respiratory metabolism of glycerol of bacteria. The invention in preferred embodiments refers to four glp operons of E. coli, in particular, glpFKX, glpABC, glpTQ, and glpD. Promoters of said operons are identified herein as glpF, glpA, glpT and glpD promoters, and abbreviated herein as PglpF, PglpA, PglpT and PglpD, correspondingly. In some other embodiments, the invention refers to the lac operon of E. coli comprising genes Z, Y and A, and its promoter lac (abbreviated herein as Plac). Preferably, a glp operon promoter sequence comprised in the promoter DNA of the construct of the invention is identical to or has at least 80% identity, preferably 90-99.9% identity with the nucleotide sequence of a fragment of E. coli genomic DNA located upstream of the sequences of Genetic Bank IDs: EG10396 (glpF), EG10391 (glpA), EG10394 (glpD), EG10401 (glpT); EG10527 (lacZ). The E. coli genome is referred herein to the complete genomic DNA sequence of E coli K-12 MG1655 (GenBank ID:U00096.3). Selected, but not limited embodiments of the promoter DNA sequences of the invention can be found in Table 1 below and are described throughout the application.

The promoter DNA sequence (ii) may comprise several structural features/elements, such as regulatory regions capable of affecting (facilitating or inhibiting) the binding of RNA polymerase in the cell and initiating transcription of the downstream (the 3'-direction) coding sequence, such as e.g. binding sites for transcription regulator proteins such as e.g. the transcriptional repressor GlpR protein or the transcriptional activator CRP protein. The regulatory region comprises protein binding domains (consensus sequences) responsible for the binding of RNA polymerase such as the −35 box and the −10 box (Pribnow box). All mentioned regulatory sequences of promoter DNA of the construct may have certain percent of identity to the corresponding genomic sequences of the promoter, i.e. the invention contemplates the original (native/wild type) DNA sequences or variants thereof. Some non-limiting useful embodiments of variants of the promoter DNA sequences (ii) can be found in Table 1 below and described though specification of the invention.

A promoter sequence of the invention preferably comprises at least 50 nucleotides, more preferably at least 60 nucleotides, such as from around 65 to around 100, from around 75 to around 115 nucleotides, from around 85 to around 125, e.g. 90 to 115, 110-120, 120-130, 130-140, 140-150, or over 150 nucleotides, such as 155-165, 165-175, 175-185, 185-195, 195-205, 205-215, 215-225, 225-235, 235-245, 245-255, 255-265, 250-350. In some embodiment the promoter sequence may be up to 500-1000 nucleotide long. In some embodiments, the selected promoter sequence may also be shorter, i.e. comprising less than 50 nucleotides. The length of a promoter DNA sequence is not a general limiting factor of the invention, as the invention in different embodiment contemplates any promoter DNA sequence (i) that is capable of binding to an RNA polymerase and initiate transcription of a gene of the expression cassette or a gene of interest in the genome. In one preferred embodiment, the promoter DNA is derived from the genomic promoter region of a glp operon, e.g. from the glpF promoter (PglpF) region, glpA promoter (PglpA) region, glpT promoter (PglpT) region, glpD promoter (PglpD) oregion. In some preferred embodiments the promoter DNA sequence (i) may be selected from any DNA sequence identified herein as SEQ ID NOs:48, 49 or 54; in some embodiments, a variant said sequences may be preferred. Non-limiting useful examples of such variants are described throughout the specification and exemplified in Table 1. In one preferred embodiment, the promoter DNA sequence is derived from the genomic DNA of *E. coli* (GenBank ID EG10396), in particular from the area of the genomic DNA comprising the promoter element of the glpFXK operon (specifically, a DNA sequence of 50-350 nucleotides upstream of the transcription start of the glpFXK operon, or a variant thereof that has at least 90% of sequence identity). One preferred embodiment of the promoter DNA sequence (i) is SEQ ID NO: 54.

In different embodiments of the invention, the invention may relate to a promoter that is inducible/regulatable or constantly active. The term "inducible promoter" is meant that activity of the promoter, i.e. the capability of the promoter to initiate and maintain transcription of the operably linked gene on a certain level, is regulable by an external factor, e.g. a carbon source molecule. In some embodiments, the activity of a promoter of the invention can be controlled by the presence or absence of a carbon source molecule in the medium, e.g. glycerol, glucose, arabinose, etc. "Carbon source" refers in general to a carbohydrate, which can be taken up and metabolized by a bacterial cell. Preferably, an inducible promoter of the invention is a carbon-source inducible glp promoter *E. coli*, preferably glpF, glpA, glpD, glpT promoter, or a variant thereof that is inducible by the same carbon source as the corresponding original promoter. Preferably, the promoter comprises at least one binding site for cyclic AMP receptor protein (cAMP-CRP). In other embodiments, the invention relates to a promoter which is non-inducible, i.e. activity of the promoter which is not dependent on induction by, e.g. a carbon-source. Preferably, the latter promoter is a glp promoter of the invention which DNA structure was modified to make the promoter activity carbon-source independent or to become constitutively active, e.g. by deleting/modifying cites for GlpR binding in the promoter sequence.

As mentioned, the invention also relates to variants of the promoter DNA sequences that may be used in constructs of the invention. By "variant" in the present content is meant an artificial nucleic acid sequence that preferably has around 70-99% similarity to a nucleotide sequence of the concerned promoter DNA sequence. The percentage of similarity of compared nucleic acid sequences indicates the portion of the sequences that has identical structure i.e. identical nucleotide composition. The percentage of sequence similarity for the purposes of the invention can be determined by using any method well-known in the art e.g. BLAST. The scope of the term "variant" includes nucleotide sequences complementary to the DNA sequences described herein, mRNA sequences and synthetic nucleotide sequences, e.g. PCR primers, and other oligonucleotides which relate to the nucleic acid sequences of constructs of the invention.

According to the invention, the construct/expression cassette comprises a synthetic non-coding DNA sequence (i), that comprises a ribosomal binding site (RBS). The term "synthetic DNA sequence" in the present context means a manmade DNA sequence, i.e. the DNA sequence is constructed artificially and it is composed of at least two DNA fragments, wherein at least one of the fragments is derived from a genomic DNA (i.e. it corresponds to a DNA sequence of a genomic DNA) and another DNA fragment is an artificial DNA sequence comprising around 16-nucleobases that, preferably, does not match to a natural bacterial genomic DNA sequence comprising a RBS. In particular, the synthetic DNA sequence (i) is composed of two DNA fragments: a first DNA fragment and a second DNA fragment. The first DNA fragment has about 70-100% sequence identity to a fragment of a genomic DNA sequence derived from the non-translated DNA sequence located downstream of the transcription initiation and upstream of the translation start of a gene, e.g. a glp gene. Preferably, the first fragment comprises at least 5 to around 60 contiguous nucleotides, such as 5-10 nucleotides, 10-15 nucleotides, 15-20 nucleotides, 20-30 nucleotides, 30-40 nucleotides, 40-50 nucleotides, 50-60 nucleotides downstream the transcription start (starting from the +2 nucleotide) of a glp gene, preferably, glpF, glpA or glpD gene. The DNA sequence of the first fragment may be homologous or heterologous with regard to the promoter DNA (ii) and/or the sequence of coding DNA (iii). The "homologous" in the present context mean that the DNA sequence of the first fragment is derived from the 5'UTR region of a gene that is naturally (in the genome of species of origin) downstream of the promoter of the construct, or it is naturally a fragment of the 5'UTR of the gene of the construct, or it is naturally associated with both; "heterologous" means that the first fragment DNA does not correspond to a fragment of the natural (genomic) 5'UTR region associated with the gene or promoter of the construct. In one preferred embodiment, the first DNA fragment is derived from the genomic 5'UTR DNA sequence of a glp gene, preferably the glpF gene. Preferably, it is heterologous with respect to the coding DNA sequence (iii). In some embodiments, it may be preferred that the DNA sequence of the first DNA fragment is homologous with respect to the promoter DNA sequence (ii); in other embodiments, it may be preferred that said first sequence is heterologous with respect to the promoter DNA sequence (i). In one preferred embodiment the first DNA fragment is or comprises the nucleotide sequence set forth in SEQ ID NO:36.

The second fragment of the artificial DNA sequence (i) is the nucleotide sequence CAAGGAGGAAACAGCT (SEQ ID NO: 10), or a variant of said sequence. Some useful not-limiting embodiments of the variant of SEQ ID NO:10 are the nucleotide sequences of SEQ ID NOS: 38-47. In some embodiments of the construct of the invention, the first DNA fragment (the 5"-UTR DNA sequence) is located downstream of the promoter DNA sequence (DNA sequence (ii)) (and upstream of the second DNA fragment); and the second DNA fragment is located upstream of the coding DNA sequence (iii) (i.e. upstream of the translation initiation start), i.e. in the artificial DNA sequence (i) the first DNA fragment is preceding the second DNA fragment. One preferred embodiment of the synthetic DNA sequence (i) is SEQ ID NO:37.

Non-limiting embodiments of the DNA sequences (i) and (ii), fragments, variants, and combinations thereof, useful in different aspects of the invention are described in Table 1.

TABLE 1

| Name: | SEQ ID: | Sequence (5'->3') | Description |
|---|---|---|---|
| PglpF_5'UTR-glpF-d16nb | SEQ ID NO: 1 | GCGGCACGCCTTGCAGATTACGGTTTGCCACACTTTT CATCCTTCTCCTGGTGACATAATCCACATCAATCGAAA ATGTTAATAAATTTGTTGCGCGAATGATCTAACAAACAT GCATCATGTACAATCAGATGGAATAAATGGCGCGATAA CGCTCATTTTATGACGAGGCACACACATTTTAAGTTCG | 284-nucleotide DNA fragment derived from genomic DNA of *E. coli* (ref. seq ID U00096.3) located 16 bp upstream |

TABLE 1-continued

| Name: | SEQ ID: | Sequence (5'->3') | Description |
|---|---|---|---|
| | | ATATTTCTCGTTTTTGCTCGTTAACGATAAGTTTACAGC ATGCCTACAAGCATCGTGGAGGTCCGTGACTTTCACG CATACAACAAACATTAAC | the glpF translation initiation codon |
| PglpA_5'UTR-glpA- d16nb | SEQ ID NO: 2 | GAAAACATTCATAAATTAAATGTGAATTGCCGCACACA TTATTAAATAAGATTTACAAAATGTTCAAAATGACGCAT GAAATCACGTTTCACTTTCGAATTATGAGCGAATATGC GCGAAATCAAACAATTCATGTTTTTACTATGGCTAAATG GTAAAAAACGAA | 166-nucleotide DNA fragment derived from genomic DNA of E. coli (ref. seq ID U00096.3) located 16 bp upstream of the glpA translation initiation codon |
| PglpD_5'UTR-glpD-d16 nb | SEQ ID NO: 3 | TGCGTCTCTCTTTCTTTACAAACAAGTGGGCAAATTTA CCGCACAGTTTACGTCGAAGCGGCAGATAAACGCCAT AATGTTATACATATCACTCTAAAATGTTTTTTCAATGTTA CCTAAAGCGCGATTCTTTGCTAATATGTTCGATAACGA ACATTTATGAGCTTTAACGAA | 174 bp DNA fragment derived from genomic DNA of E. coli (ref. seq ID U00096.3). located 16 bp upstream of the glpD translation initiation codon |
| PglpT_5'UTR-glpT-d16nb | SEQ ID NO: 4 | CCATTTAGCCATAGTAAAAACATGAATTGTTTGATTTCG CGCATATTCGCTCATAATTCGAAAGTGAAACGTGATTT CATGCGTCATTTTGAACATTTTGTAAATCTTATTTAATA ATGTGTGCGGCAATTCACATTTAATTTATGAATGTTTTC TTAACATCGCGGCAACTCAAGAAACGGCAGGTTCTCT CACTGAATCAGGCTGTTAATCATAAATAAGACCACGG | 229 bp DNA fragment derived from genomic DNA of E. coli (ref. seq ID U00096.3). Located 60 bp upstream of the glpT translation initiation codon |
| 16nb-glpF | SEQ ID NO: 5 | TCTTCAGGATCCGATT | 16-nucleotide DNA fragment derived from genomic DNA of E. coli (ref. seq ID U00096.3) located directly upstream the translational initiation codon of glpF |
| 16nb-glpA | SEQ ID NO: 6 | CTTCAGAGGGATAACA | 16-nucleotide DNA fragment derived from genomic DNA of E. coli (ref. seq ID U00096.3) located directly upstream the translational initiation codon of glpA |
| 16nb-glpD | SEQ ID NO: 7 | AGTGAATGAGGGCAGC | 16-nucleotide DNA fragment derived from genomic DNA of E. coli (ref. seq ID U00096.3) located upstream the translational initiation codon of glpD |
| 16nb-glpT | SEQ ID NO: 8 | GCCACGGAGGCTATCA | 16-nucleotide DNA fragment derived from genomic DNA of E. coli (ref. seq ID U00096.3) located directly upstream the translational initiation codon of glpT |
| 16bnb-lacZ | SEQ ID NO: 9 | CACACAGGAAACAGCT | 16-nucleotide DNA fragment derived from genomic DNA of E. coli (ref. seq ID U00096.3). located upstream of lacZ |
| mut16bp-lacZ (recRBS) | SEQ ID NO: 10 | CAAGGAGGAAACAGCT | Variant of SEQ ID NO: 9) (CAC -> AGG) |

TABLE 1-continued

| Name: | SEQ ID: | Sequence (5'->3') | Description |
|---|---|---|---|
| Plac_org | SEQ ID NO: 11 | TGTGAGTTAGCTCACTCATTAGGCACCCCAGGCTTTAC ACTTTATGCTTCCGGCTCGTATGTTGTGTGGAATTGTG AGCGGATAACAATTTCACACAGGAAACAGCT | 107-nucleotide DNA fragment located upstream of lacZ derived from genomic DNA of *E. coli* (ref. seq ID U00096.3); lac operon promoter element |
| PglpF_54nb 5'URT-glpF_recRBS (PglpF_rec) | SEQ ID NO: 12 | GCGGCACGCCTTGCAGATTACGGTTTGCCACACTTTT CATCCTTCTCCTGGTGACATAATCCACATCAATCGAAA ATGTTAATAAATTTGTTGCGCGAATGATCTAACAAACAT GCATCATGTACAATCAGATGGAATAAATGGCGCGATAA CGCTCATTTTATGACGAGGCACACACATTTTAAGTTCG ATATTTCTCGTTTTTGCTCGTTAACGATAAGTTTACAGC ATGCCTACAAGCATCGTGGAGGTCCGTGACTTTCACG CATACAACAAACATTAACCAAGGAGGAAACAGCT | 300-nucleotide DNA fragment comprising SEQ ID NO: 1 and SEQ ID NO: 10 |
| PglpF_SD1 | SEQ ID NO: 13 | GCGGCACGCCTTGCAGATTACGGTTTGCCACACTTTT CATCCTTCTCCTGGTGACATAATCCACATCAATCGAAA ATGTTAATAAATTTGTTGCGCGAATGATCTAACAAACAT GCATCATGTACAATCAGATGGAATAAATGGCGCGATAA CGCTCATTTTATGACGAGGCACACACATTTTAAGTTCG ATATTTCTCGTTTTTGCTCGTTAACGATAAGTTTACAGC ATGCCTACAAGCATCGTGGAGGTCCGTGACTTTCACG CATACAACAAACATTAACCAAATTCGAAACAGCT | 300-nucleotide DNA fragment comprising SEQ ID NO: 1 and SEQ ID NO: 38 (See FIG. 6) |
| PglpF_SD2 | SEQ ID NO: 14 | GCGGCACGCCTTGCAGATTACGGTTTGCCACACTTTT CATCCTTCTCCTGGTGACATAATCCACATCAATCGAAA ATGTTAATAAATTTGTTGCGCGAATGATCTAACAAACAT GCATCATGTACAATCAGATGGAATAAATGGCGCGATAA CGCTCATTTTATGACGAGGCACACACATTTTAAGTTCG ATATTTCTCGTTTTTGCTCGTTAACGATAAGTTTACAGC ATGCCTACAAGCATCGTGGAGGTCCGTGACTTTCACG CATACAACAAACATTAACCAAGCGCAAACAGCT | 300-nucleotide DNA fragment comprising SEQ ID NO: 1 and SEQ ID NO: 39 (See FIG. 6) |
| PglpF_SD3 | SEQ ID NO: 15 | GCGGCACGCCTTGCAGATTACGGTTTGCCACACTTTT CATCCTTCTCCTGGTGACATAATCCACATCAATCGAAA ATGTTAATAAATTTGTTGCGCGAATGATCTAACAAACAT GCATCATGTACAATCAGATGGAATAAATGGCGCGATAA CGCTCATTTTATGACGAGGCACACACATTTTAAGTTCG ATATTTCTCGTTTTTGCTCGTTAACGATAAGTTTACAGC ATGCCTACAAGCATCGTGGAGGTCCGTGACTTTCACG CATACAACAAACATTAACCAAGAACAAAACAGCT | 300-nucleotide DNA fragment comprising SEQ ID NO: 1 and SEQ ID NO: 40 (See FIG. 6) |
| PglpF_SD4 | SEQ ID NO: 16 | GCGGCACGCCTTGCAGATTACGGTTTGCCACACTTTT CATCCTTCTCCTGGTGACATAATCCACATCAATCGAAA ATGTTAATAAATTTGTTGCGCGAATGATCTAACAAACAT GCATCATGTACAATCAGATGGAATAAATGGCGCGATAA CGCTCATTTTATGACGAGGCACACACATTTTAAGTTCG ATATTTCTCGTTTTTGCTCGTTAACGATAAGTTTACAGC ATGCCTACAAGCATCGTGGAGGTCCGTGACTTTCACG CATACAACAAACATTAACCAACTAGGAAACAGCT | 300-nucleotide DNA fragment comprising SEQ ID NO: 1 and SEQ ID NO: 41 (See FIG. 6) |
| PglpF_SD5 | SEQ ID NO: 17 | GCGGCACGCCTTGCAGATTACGGTTTGCCACACTTTT CATCCTTCTCCTGGTGACATAATCCACATCAATCGAAA ATGTTAATAAATTTGTTGCGCGAATGATCTAACAAACAT GCATCATGTACAATCAGATGGAATAAATGGCGCGATAA CGCTCATTTTATGACGAGGCACACACATTTTAAGTTCG ATATTTCTCGTTTTTGCTCGTTAACGATAAGTTTACAGC ATGCCTACAAGCATCGTGGAGGTCCGTGACTTTCACG CATACAACAAACATTAACCAACCGAGAAACAGCT | 300-nucleotide DNA fragment comprising SEQ ID NO: 1 and SEQ ID NO: 42 (See FIG. 6) |
| PglpF_SD6 | SEQ ID NO: 18 | GCGGCACGCCTTGCAGATTACGGTTTGCCACACTTTT CATCCTTCTCCTGGTGACATAATCCACATCAATCGAAA ATGTTAATAAATTTGTTGCGCGAATGATCTAACAAACAT GCATCATGTACAATCAGATGGAATAAATGGCGCGATAA CGCTCATTTTATGACGAGGCACACACATTTTAAGTTCG ATATTTCTCGTTTTTGCTCGTTAACGATAAGTTTACAGC ATGCCTACAAGCATCGTGGAGGTCCGTGACTTTCACG CATACAACAAACATTAACCAAGAGCTAAACAGCT | 300-nucleotide DNA fragment comprising SEQ ID NO: 1 and SEQ ID NO:43 (See FIG. 6) |
| PglpF_SD7 | SEQ ID NO: 19 | GCGGCACGCCTTGCAGATTACGGTTTGCCACACTTTT CATCCTTCTCCTGGTGACATAATCCACATCAATCGAAA ATGTTAATAAATTTGTTGCGCGAATGATCTAACAAACAT GCATCATGTACAATCAGATGGAATAAATGGCGCGATAA CGCTCATTTTATGACGAGGCACACACATTTTAAGTTCG | 300-nucleotide DNA fragment comprising SEQ ID NO: 1 and SEQ ID NO: 44 (See FIG. 7)4 |

TABLE 1-continued

| Name: | SEQ ID: | Sequence (5'->3') | Description |
|---|---|---|---|
| | | ATATTTCTCGTTTTTGCTCGTTAACGATAAGTTTACAGC ATGCCTACAAGCATCGTGGAGGTCCGTGACTTTCACG CATACAACAAACATTAACCAAGAGCAAAACAGCT | |
| PglpF_SD8 | SEQ ID NO: 20 | GCGGCACGCCTTGCAGATTACGGTTTGCCACACTTTT CATCCTTCTCCTGGTGACATAATCCACATCAATCGAAA ATGTTAATAAATTTGTTGCGCGAATGATCTAACAAACAT GCATCATGTACAATCAGATGGAATAAATGGCGCGATAA CGCTCATTTTATGACGAGGCACACACATTTTAAGTTCG ATATTTCTCGTTTTTGCTCGTTAACGATAAGTTTACAGC ATGCCTACAAGCATCGTGGAGGTCCGTGACTTTCACG CATACAACAAACATTAACCAAGAGAAAACAGCT | 300-nucleotide DNA fragment comprising SEQ ID NO: 1 and SEQ ID NO: 45 (See FIG. 7) |
| PglpF_SD9 | SEQ ID NO: 21 | GCGGCACGCCTTGCAGATTACGGTTTGCCACACTTTT CATCCTTCTCCTGGTGACATAATCCACATCAATCGAAA ATGTTAATAAATTTGTTGCGCGAATGATCTAACAAACAT GCATCATGTACAATCAGATGGAATAAATGGCGCGATAA CGCTCATTTTATGACGAGGCACACACATTTTAAGTTCG ATATTTCTCGTTTTTGCTCGTTAACGATAAGTTTACAGC ATGCCTACAAGCATCGTGGAGGTCCGTGACTTTCACG CATACAACAAACATTAACCAAAGGAAAAACAGCT | 300-nucleotide DNA fragment comprising SEQ ID NO: 1 and SEQ ID NO: 46 (See FIG. 7) |
| PglpF_SD10 | SEQ ID NO: 22 | GCGGCACGCCTTGCAGATTACGGTTTGCCACACTTTT CATCCTTCTCCTGGTGACATAATCCACATCAATCGAAA ATGTTAATAAATTTGTTGCGCGAATGATCTAACAAACAT GCATCATGTACAATCAGATGGAATAAATGGCGCGATAA CGCTCATTTTATGACGAGGCACACACATTTTAAGTTCG ATATTTCTCGTTTTTGCTCGTTAACGATAAGTTTACAGC ATGCCTACAAGCATCGTGGAGGTCCGTGACTTTCACG CATACAACAAACATTAACCAACTGAGAAACAGCT | 300-nucleotide DNA fragment comprising SEQ ID NO: 1 and SEQ ID NO: 47 (See FIG. 7) |
| PglpF_9 | SEQ ID NO: 23 | GCGGCACGCCTTGCAGATTACGGTTTGCCACACTTTT CATCCTTCTCCTGGTGACATAATCCACATCAATCGAAA ATGTTAATAAATTTGTTGCGCGAATGATCTAACAAACAT GCATCATGTACAATCAGATGGAATAAATGGCGCGATAA CGCTCATTTTATGACGAGGCACACACATTTTAAGTTCG ATATTTCTCGTTTTTGCTCGTTAACGATTTAATTACAGC ATGCCTACAAGCATCGTGGAGGTCCGTGACTTTCACG CATACAACAAACATTAACCAAGGAGGAAACAGCT | Variant of SEQ ID NO: 12 comprising a modification of the -10 region (See FIG. 7) |
| PglpF_11 | SEQ ID NO: 24 | GCGGCACGCCTTGCAGATTACGGTTTGCCACACTTTT CATCCTTCTCCTGGTGACATAATCCACATCAATCGAAA ATGTTAATAAATTTGTTGCGCGAATGATCTAACAAACAT GCATCATGTACAATCAGATGGAATAAATGGCGCGATAA CGCTCATTTTATGACGAGGCACACACATTTTAAGTTCG ATATTTCTCGTTTTTGCTCGTTAACGATCAGAATACAGC ATGCCTACAAGCATCGTGGAGGTCCGTGACTTTCACG CATACAACAAACATTAACCAAGGAGGAAACAGCT | Variant of SEQ ID NO: 12 comprising a modification of the -10 region (See FIG. 7) |
| PglpF_13 | SEQ ID NO: 25 | GCGGCACGCCTTGCAGATTACGGTTTGCCACACTTTT CATCCTTCTCCTGGTGACATAATCCACATCAATCGAAA ATGTTAATAAATTTGTTGCGCGAATGATCTAACAAACAT GCATCATGTACAATCAGATGGAATAAATGGCGCGATAA CGCTCATTTTATGACGAGGCACACACATTTTAAGTTCG ATATTTCTCGTTTTTGCTCGTTAACGATATCCTTCCTAC AGCATGCCTACAAGCATCGTGGAGGTCCGTGACTTTC ACGCATACAACAAACATTAACCAAGGAGGAAACAGCT | Variant of SEQ ID NO: 12 comprising a modification of the -10 region (See FIG. 7) |
| PglpF_17 | SEQ ID NO: 26 | GCGGCACGCCTTGCAGATTACGGTTTGCCACACTTTT CATCCTTCTCCTGGTGACATAATCCACATCAATCGAAA ATGTTAATAAATTTGTTGCGCGAATGATCTAACAAACAT GCATCATGTACAATCAGATGGAATAAATGGCGCGATAA CGCTCATTTTATGACGAGGCACACACATTTTAAGTTCG ATATTTCTCGTTTTTGCTCGTTAACGATAATGATACAGC ATGCCTACAAGCATCGTGGAGGTCCGTGACTTTCACG CATACAACAAACATTAACCAAGGAGGAAACAGCT | Variant of SEQ ID NO: 12 comprising a modification of the -10 region (See FIG. 7) |
| PglpF_19 | SEQ ID NO: 27 | GCGGCACGCCTTGCAGATTACGGTTTGCCACACTTTT CATCCTTCTCCTGGTGACATAATCCACATCAATCGAAA ATGTTAATAAATTTGTTGCGCGAATGATCTAACAAACAT GCATCATGTACAATCAGATGGAATAAATGGCGCGATAA CGCTCATTTTATGACGAGGCACACACATTTTAAGTTCG ATATTTCTCGTTTTTGCTCGTTAACGATGAAGCTACAG CATGCCTACAAGCATCGTGGAGGTCCGTGACTTTCAC GCATACAACAAACATTAACCAAGGAGGAAACAGCT | Variant of SEQ ID NO: 12 comprising a modification of the -10 region (See FIG. 7) |

TABLE 1-continued

| Name: | SEQ ID: | Sequence (5'->3') | Description |
|---|---|---|---|
| PglpF_20 | SEQ ID NO: 28 | GCGGCACGCCTTGCAGATTACGGTTTGCCACACTTTT CATCCTTCTCCTGGTGACATAATCCACATCAATCGAAA ATGTTAATAAATTTGTTGCGCGAATGATCTAACAAACAT GCATCATGTACAATCAGATGGAATAAATGGCGCGATAA CGCTCATTTTATGACGAGGCACACACATTTTAAGTTCG ATATTTCTCGTTTTTGCTCGTTAACGATCAGTATACAGC ATGCCTACAAGCATCGTGGAGGTCCGTGACTTTCACG CATACAACAAACATTAACCAAGGAGGAAACAGCT | Variant of SEQ ID NO: 12 comprising a modification of the -10 region (See FIG. 7) |
| D15PglpF | SEQ ID NO: 29 | GATTACGGTTTGCCACACTTTTCATCCTTCTCCTGGTG ACATAATCCACATCAATCGAAATGTTAATAAATTTGTT GCGCGAATGATCTAACAAACATGCATCATGTACAATCA GATGGAATAAATGGCGCGATAACGCTCATTTTATGACG AGGCACACACATTTTAAGTTCGATATTTCTCGTTTTTGC TCGTTAACGATAAGTTTACAGCATGCCTACAAGCATCG TGGAGGTCCGTGACTTTCACGCATACAACAAACATTAA CCAAGGAGGAAACAGCT | 285-nucleotide DNA fragment of SEQ ID NO: 12 |
| D140PglpF | SEQ ID NO: 30 | ATGGCGCGATAACGCTCATTTTATGACGAGGCACACA CATTTTAAGTTCGATATTTCTCGTTTTTGCTCGTTAACG ATAAGTTTACAGCATGCCTACAAGCATCGTGGAGGTCC GTGACTTTCACGCATACAACAAACATTAACCAAGGAGG AAACAGCT | 160-nucleotide DNA fragment of SEQ ID NO: 12 |
| D165PglpF | SEQ ID NO: 31 | ACGAGGCACACACATTTTAAGTTCGATATTTCTCGTTTT TGCTCGTTAACGATAAGTTTACAGCATGC CTACAAGCATCGTGGAGGTCCGTGACTTTCACGCATA CAACAAACATTAACCAAGGAGGAAACAGCT | 135-nucleotide DNA fragment of SEQ ID NO: 12 |
| D180PglpF | SEQ ID NO: 32 | TTTAAGTTCGATATTTCTCGTTTTTGCTCGTTAACGATA AGTTTACAGCATGCCTACAAGCATCG TGGAGGTCCGTGACTTTCACGCATACAACAAACATTAA CCAAGGAGGAAACAGCT | 120-nucleotide DNA fragment of SEQ ID NO: 12 |
| PglpA_-5'UTR-glpA_recRBS (rec PglpA) | SEQ ID NO: 33 | GAAAACATTCATAAATTAAATGTGAATTGCCGCACACA TTATTAAATAAGATTTACAAAATGTTCAAAATGACGCAT GAAATCACGTTTCACTTTCGAATTATGAGCGAATATGC GCGAAATCAAACAATTCATGTTTTTACTATGGCTAAATG GTAAAAAACGAACAAGGAGGAAACAGCT | 182-nucleotide DNA fragment comprising SEQ ID NO: 2 and SEQ ID NO: 10 |
| PglpD_5'UTR-glpD_recRBS (rec PglpD) | SEQ ID NO: 34 | TGCGTCTCTCTTTCTTTACAAACAAGTGGGCAAATTTA CCGCACAGTTTACGTCGAAGCGGCAGATAAACGCCAT AATGTTATACATATCACTCTAAAATGTTTTTTCAATGTTA CCTAAAGCGCGATTCTTTGCTAATATGTTCGATAACGA ACATTTATGAGCTTTAACGAACAAGGAGGAAACAGCT | 190-nucleotide DNA fragment comprising SEQ ID NO: 3 and SEQ ID NO: 10 |
| PglpT_5'UTR-glpT_recRBS (rec_PglpT | SEQ ID NO: 35 | CCATTTAGCCATAGTAAAAACATGAATTGTTTGATTTCG CGCATATTCGCTCATAATTCGAAAGTGAAACGTGATTT CATGCGTCATTTTGAACATTTTGTAAATCTTATTTAATA ATGTGTGCGGCAATTCACATTTAATTTATGAATGTTTTC TTAACATCGCGGCAACTCAAGAAACGGCAGGTTCTCT CACTGAATCAGGCTGTTAATCATAAATAAGACCACGGC AAGGAGGAAACAGCT | 245-nucleotide DNA fragment comprising SEQ ID NO: 4 and SEQ ID NO: 10 |
| 54nb 5'UTR-glpF | SEQ ID NO: 36 | TGCCTACAAGCATCGTGGAGGTCCGTGACTTTCACGC ATACAACAAACATTAAC | 54-nucleotide DNA fragment of the 5'UTR-glpF located downstream of the transcription initiation site and 16 nucleotides upstream the translation initiation codon |
| synDNA(i) (70UTR) | SEQ ID NO: 37 | TGCCTACAAGCATCGTGGAGGTCCGTGACTTTCACGC ATACAACAAACATTAACCAAGGAGGAAACAGCT | 70-nucleotide synthetic non-coding DNA sequence (ii) comprising SEQ ID NO: 36 and SEQ ID NO: 10 |
| recRBS_v1 (SD1) | SEQ ID NO: 38 | CAAATTCGAAACAGCT | Variant of SEQ ID NO: 10 (see FIG. 6, A) |
| recRBS_v2 (SD2) | SEQ ID NO: 39 | CAAGCGCAAACAGCT | Variant of SEQ ID NO: 10 (see FIG. 6, A) |

TABLE 1-continued

| Name: | SEQ ID: | Sequence (5'->3') | Description |
|---|---|---|---|
| recRBS_v3 (SD3) | SEQ ID NO: 40 | CAAGAACAAACAGCT | Variant of SEQ ID NO: 10 (see FIG. 6, A) |
| recRBS_v4 (SD4) | SEQ ID NO: 41 | CAACTAGGAAACAGCT | Variant of SEQ ID NO: 10 (see FIG. 6, A) |
| recRBS_v5 (SD5) | SEQ ID NO: 42 | CAACCGAGAAACAGCT | Variant of SEQ ID NO: 10 (see FIG. 6, A) |
| recRBS_v6 (SD6) | SEQ ID NO: 43 | CAAGAGCTAAACAGCT | Variant of SEQ ID NO: 10 (see FIG. 6, A) |
| recRBS_v7 (SD7) | SEQ ID NO: 44 | CAAGAGCAAACAGCT | Variant of SEQ ID NO: 10 (see FIG. 6, A) |
| recRBS_v8 (SD8) | SEQ ID NO: 45 | CAAGAGAAAACAGCT | Variant of SEQ ID NO: 10 (see FIG. 6, A) |
| recRBS_v9 (SD9) | SEQ ID NO: 46 | CAAAGGAAAACAGCT | Variant of SEQ ID NO: 10 (see FIG. 6, A) |
| recRBS_v10 (SD10) | SEQ ID NO: 47 | CAACTGAGAAACAGCT | Variant of SEQ ID NO: 10 (see FIG. 6, A) |
| PglpA_org | SEQ ID NO: 48 | GAAAACATTCATAAATTAAATGTGAATTGCCGCACACA TTATTAAATAAGATTTACAAAATGTTCAAAATGACGCAT GAAATCACGTTTCACTTTCGAATTATGAGCGAATATGC GCGA | 119-nucleotide DNA fragment derived from genomic DNA of E. coli (ref. seq ID U00096.3) located upstream of the glpA transcription initiation start; glpA promoter element |
| PglpT_org | SEQ ID NO: 49 | CCATTTAGCCATAGTAAAAACATGAATTGTTTGATTTCG CGCATATTCGCTCATAATTCGAAAGTGAAACGTGATTT CATGCGTCATTTTGAACATTTTGTAAATCTTATTTAATA ATGTGTGCGGCAATTCACATTTAATTTATGAATGTTTTC TTAACATCGCGGCA | 169-nucleotide DNA fragment derived from genomic DNA of E. coli (ref. seq ID U00096.3) located upstream of the glpT transcription initiation start; glpT promoter element |
| PglpA_70UTR | SEQ ID NO: 50 | GAAAACATTCATAAATTAAATGTGAATTGCCGCACACA TTATTAAATAAGATTTACAAAATGTTCAAAATGACGCAT GAAATCACGTTTCACTTTCGAATTATGAGCGAATATGC GCGATGCCTACAAGCATCGTGGAGGTCCGTGACTTTC ACGCATACAACAAACATTAACCAAGGAGGAAACAGCT | 189-nucleotide DNA fragment obtained by combining SEQ ID NO: 49 with SEQ ID NO 37 |
| PglpT_70UTR | SEQ ID NO: 51 | CCATTTAGCCATAGTAAAAACATGAATTGTTTGATTTCG CGCATATTCGCTCATAATTCGAAAGTGAAACGTGATTT CATGCGTCATTTTGAACATTTTGTAAATCTTATTTAATA ATGTGTGCGGCAATTCACATTTAATTTATGAATGTTTTC TTAACATCGCGGCA TGCCTACAAGCATCGTGGAGGTCCGTGACTTTCACGC ATACAACAAACATTAACCAAGGAGGAAACAGCT | 239-nucleotide DNA fragment obtained by combing SEQ ID NO: 50 with synthetic non-coding DNA sequence (ii) (SEQ ID NO 37) |
| PglpT_70UTR_SD4 | SEQ ID NO: 52 | CCATTTAGCCATAGTAAAAACATGAATTGTTTGATTTCG CGCATATTCGCTCATAATTCGAAAGTGAAACGTGATTT CATGCGTCATTTTGAACATTTTGTAAATCTTATTTAATA ATGTGTGCGGCAATTCACATTTAATTTATGAATGTTTTC TTAACATCGCGGCA TGCCTACAAGCATCGTGGAGGTCCGTGACTTTCACGC ATACAACAAACATTAACCAACTAGGAAACAGCT | 239-nucleotide DNA fragment SEQ ID NO: 50 where the 16 bp located upstream of the translation initiation site is identical to SEQ ID NO 41 |
| PglpT_70UTR_SD9 | SEQ ID NO: 53 | CCATTTAGCCATAGTAAAAACATGAATTGTTTGATTTCG CGCATATTCGCTCATAATTCGAAAGTGAAACGTGATTT CATGCGTCATTTTGAACATTTTGTAAATCTTATTTAATA ATGTGTGCGGCAATTCACATTTAATTTATGAATGTTTTC TTAACATCGCGGCA TGCCTACAAGCATCGTGGAGGTCCGTGACTTTCACGC ATACAACAAACATTAACCAAAGGAAAACAGCT | 239-nucleotide DNA fragment SEQ ID NO: 50 where the 16 bp located upstream of the translation initiation site is identical to SEQ ID NO 46 |

TABLE 1-continued

| Name: | SEQ ID: | Sequence (5'->3') | Description |
|---|---|---|---|
| PglpF_org | SEQ ID NO: 54 | GCGGCACGCCTTGCAGATTACGGTTTGCCACACTTTT CATCCTTCTCCTGGTGACATAATCCACATCAATCGAAA ATGTTAATAAATTTGTTGCGCGAATGATCTAACAAACAT GCATCATGTACAATCAGATGGAATAAATGGCGCGATAA CGCTCATTTTATGACGAGGCACACACATTTTAAGTTCG ATATTTCTCGTTTTTGCTCGTTAACGATAAGTTTACAGC A | 230-nucleotide DNA sequence derived from genomic DNA of E. coli (ref. seq ID U00096.3) located upstream the initiation of transcription of glpF; glpF promoter element |
| PglpT-5'UTR-glpT_org | SEQ ID NO: 55 | CCATTTAGCCATAGTAAAAACATGAATTGTTTGATTTCG CGCATATTCGCTCATAATTCGAAAGTGAAACGTGATTT CATGCGTCATTTTGAACATTTTGTAAATCTTATTTAATA ATGTGTGCGGCAATTCACATTTAATTTATGAATGTTTTC TTAACATCGCGGCAACTCAAGAAACGGCAGGTTCTCT CACTGAATCAGGCTGTTAATCATAAATAAGACCACGGG CCACGGAGGCTATCA | 245-nucleotide nucleotide DNA sequence derived from genomic DNA of E. coli (ref. seq ID U00096.3) located upstream the initiation of translation of glpT |
| PglpA-5'UTR-glpA_org | SEQ ID NO: 56 | GAAAACATTCATAAATTAAATGTGAATTGCCGCACACA TTATTAAATAAGATTTACAAAATGTTCAAAATGACGCAT GAAATCACGTTTCACTTTCGAATTATGAGCGAATATGC GCGAAATCAAACAATTCATGTTTTTACTATGGCTAAATG GTAAAAAACGAA CTTCAGAGGGATAACA | 182-nucleotide DNA sequence derived from genomic DNA of E. coli (ref. seq ID U00096.3) located upstream the initiation of translation of glpA |
| PglpF-5'UTR-glpF_org | SEQ ID NO: 57 | GCGGCACGCCTTGCAGATTACGGTTTGCCACACTTTT CATCCTTCTCCTGGTGACATAATCCACATCAATCGAAA ATGTTAATAAATTTGTTGCGCGAATGATCTAACAAACAT GCATCATGTACAATCAGATGGAATAAATGGCGCGATAA CGCTCATTTTATGACGAGGCACACACATTTTAAGTTCG ATATTTCTCGTTTTTGCTCGTTAACGATAAGTTTACAGC ATGCCTACAAGCATCGTGGAGGTCCGTGACTTTCACG CATACAACAAACATTAACTCTTCAGGATCCGATT | 300-nucleotide DNA sequence derived from genomic DNA of E. coli (ref. seq ID U00096.3) located upstream the initiation of translation of glpF |
| PglpD-5'UTR-glpD_org | SEQ ID NO: 104 | TGCGTCTCTCTTTCTTTACAAACAAGTGGGCAAATTTA CCGCACAGTTTACGTCGAAGCGGCAGATAAACGCCAT AATGTTATACATATCACTCTAAAATGTTTTTTCAATGTTA CCTAAAGCGCGATTCTTTGCTAATATGTTCGATAACGA ACATTTATGAGCTTTAACGAA AGTGAATGAGGGCAGC | 190-nucleotide DNA sequence derived from genomic DNA of E. coli (ref. seq ID U00096.3) located upstream of the initiation of translation of glpD |

As mentioned, in some preferred embodiments, the construct comprises three operably linked DNA sequences: the promoter DNA sequence (ii), the synthetic non-coding DNA sequence (i), and at least one coding DNA sequence (iii) (gene). The coding DNA sequence (iii) is an isolated DNA sequence that has approximately 70-100% sequence identity to a fragment of genomic DNA that comprise a gene encoding a biological molecule, e.g. protein or RNA. The coding DNA (iii) of the construct may be homologous or heterologous to the promoter DNA sequence (ii). "Heterologous" in the present context means that expression of the corresponding genomic coding DNA sequence t is normally controlled by another promoter than the promoter of the construct. Accordingly, "homologous" in the present context means that the corresponding genomic sequences of the promoter DNA sequence (ii) and the coding DNA sequence (iii) are naturally linked in the genome of species of origin.

By the term "coding nucleic acid sequence" is meant a nucleic acid sequence that comprises a set of consecutive, non-overlapping triplets (codons) which is transcribed into mRNA and translated into a polypeptide when placed under the control of the appropriate control sequences, i.e. promoter. The boundaries of the coding sequence are generally determined by a ribosome binding site located just upstream of the open reading frame at the 5' end of the mRNA, a transcriptional start codon (AUG, GUG or UUG), and a translational stop codon (UAA, UGA or UAG). A coding sequence can include, but is not limited to, genomic DNA, cDNA, synthetic, and recombining nucleic acid sequences.

In a preferred embodiment, the coding nucleic acid sequence of the construct of the invention is heterologous with respect to the promoter and, in some embodiments, also to the first DNA fragment of the non-coding DNA sequence (i) of the construct. Still, with respect to the host cell, in which the coding DNA is to be expressed, said DNA may be either heterologous (i.e. derived from another biological species or genus) or homologous (i.e. derived from the host cell). For example, in one embodiment, the coding DNA sequence of the construct may encode a biological molecule, e.g. a protein that is foreign to the host, i.e. the nucleic acid sequence of the coding DNA is heterologous to the host species as it is originating from a donor species which is different from the host organism, or the nucleic acid sequence of the coding DNA contains modification that results in expression of a polypeptide that is not identical to a polypeptide expressed from the corresponding non-modified DNA sequence of the host, i.e. an artificially modified coding DNA sequence originally derived from the host is regarded in the present context as heterologous. In case the host is a particular prokaryotic species, the heterologous nucleic acid sequence may originate from a different genus of family, a different order or class, a different phylum (division), or a different domain (empire) of organisms. The heterologous nucleic acid sequence originating from a donor different from the host can be modified, before it is introduced into the host cell, by mutations, insertions, deletions or substitutions of single nucleic acids or a part of the heterologous nucleic acid sequence as long as such modified sequences exhibit the same function (functionally equivalent) as a reference sequence. A heterologous nucleic acid sequence, as referred herein, encompasses as well nucleic sequences originating from a different domain (empire) of organisms such as from eukaryotes (of eukaryotic origin), such as e.g. enzymes involved in synthesis or degradation of human milk oligosaccharides (HMOs). Still, in other embodiments of the invention, the coding nucleic acid may be homologous with respect to the host cell. The term "homologous nucleic acid sequence" (synonymously used herein as "nucleic acid sequence native to a host" or "nucleic acid sequence derived from the host") in this context means that the nucleic acid sequence originates (or derives) from the same organism, or same genus of family, or same order or class, the same phylum (division), or same domain (empire) of organisms as the host organism. In one embodiment, the coding DNA of the construct described herein may encode an enzyme or a sugar transporter protein which are normally expressed by the host bacterial cell that naturally comprises in its genome genes encoding said enzyme or sugar transporter protein.

Generally, any coding DNA is contemplated by the invention as any coding DNA can be included in a construct of the invention and transcribed from a promoter included in the construct. In some preferred embodiments the coding DNA encodes a protein, e.g. an enzyme, transport protein, regulatory protein, chaperone, etc. The term "protein" is interchangeably termed herein as "polypeptide". In other preferred embodiments, the coding DNA might encode a regulatory (non-coding) RNA molecule (ncRNA), e.g. such as functionally important types of non-coding RNAs as transfer RNAs (tRNAs) and ribosomal RNAs (rRNAs), as well as small RNAs such as microRNAs, siRNAs, and the long ncRNAs. In a preferred embodiment, at least one coding DNA of the construct of the invention encodes a protein or an RNA related to the synthesis, degradation or transport of human milk oligosaccharides, precursors or derivatives thereof. "At least one coding DNA sequence" means that the construct in different embodiments may comprise more than one coding DNA sequence, e.g. two coding sequences, such as a first and a second coding sequence; three coding sequences, such as a first, a second and a third coding sequence etc. Preferably, multiple coding DNA sequence are in these embodiments are expressed as tandem, and the transcription is controlled by a single copy of the promoter DNA (ii) of the construct. The first, second, third, etc. coding DNA sequences may in different embodiments encode for different enzymes or other proteins that function is essential or beneficial for the HMO production by a host cell, e.g. enzymes, transporter proteins, regulatory proteins, chaperones, etc. By "essential" in the present context is meant that the protein is involved in the HMO synthesis directly, e.g. it is an enzyme that assists the process of making an HMO from the HMO precursor, e.g. an enzyme with glucosyltransferase activity. By "beneficial" in the present context is meant that the protein is not involved in the HMO synthesis directly, but it assists a process that is beneficial for the HMO production by a host cell, e.g. it a protein that assists transport (into or out of the host cell) of an HMO or an HMO precursor. Some not-limiting embodiments of proteins, which are regarded herein essential for the production of one or more HMOs by a host cell can be found in Table 2, and proteins that are regarded as beneficial for the production of one or more HMOs by a host cell can be found in Table 3, below.

TABLE 2

| Gene | Sequence ID (Gen Bank) | Description | HMO example |
|---|---|---|---|
| lgtA | WP_002248149.1 | β-1,3-N-acetylglucosaminyltransferase | LNT, LNnT, LNFP-I, LNFP-II, LNFP-III, LN FP-V, LNFP-VI, LNDFH-I, LNDFH-II, pLNH, F-pLNH I, pLNnH |
| galT | NP_207619.1 | β-1,4-galactosyltransferase | LNnT, LNFP-III, LNFP-VI, pLNH, F-pLNH I, pLNnH |
| cpsIBJ | AB050723 | β-1,3-galactosyltransferase | LNT, LNFP-I, LNFP-II, LNFP-V, LNDFH-I, LNDFH-II, pLNH, F-pLNH I |
| MAMA_R764 | AGC02224.1 | α-1,3-fucosyl-transferase | 2'FL, 3'FL, DFL, LNFP-I, LNFP-III, LNFP-V, LNFP-VI, LNDFH-II, F-pLNH I |
| Mg791 | AEQ33441.1 | α-1,3-fucosyl-transferase | 2'FL, 3'FL, DFL, LNFP-I, LNFP-III, LNFP-V, LNFP-VI, LNDFH-II, F-pLNH I |
| Moumou_00703 | AGC02224.1 | α-1,3-fucosyl-transferase | 2'FL, 3'FL, DFL, LNFP-I, LNFP-III, LNFP-V, LNFP-VI, LNDFH-II, F-pLNH I |
| futA | NP_207177.1 | α-1,3-fucosyl-transferase | 2'FL, 3'FL, DFL, LNFP-I, LNFP-III, LNFP-V, LNFP-VI, LNDFH-II, F-pLNH I |
| futC | CP003904 | α-1,2-fucosyl-transferase | 2'FL, DFL, LNFP-I, LNDFH-I |
| fucT | AAB81031.1 | α-1,3-fucosyl-transferase | 2'FL, 3'FL, DFL, LNFP-I, LNFP-III, LNFP-V, LNFP-VI, LNDFH-II, F-pLNH I |
| fucTIII | AY450598 | α-1,4-fucosyl-transferase | LNDFH-1,LNDFH-II |
| fucTa | AF194963 | α-1,3/4-fucosyl-transferase | LNFP-II, LNDFH-I, LNDFH-II |
| Pd2,6ST | BAA25316.1 | α-2,6-sialyltransferase | 6'SL |
| PspST6 | BAF92026.1 | α-2,6-sialyltransferase | 6'SL |
| PiST6_145 | BAF91416.1 | α-2,6-sialyltransferase | 6'SL |
| PiST6_119 | BA149484.1 | α-2,6-sialyltransferase | 6'SL |
| NST | AAC44541.1 | α-2,3-sialyltransferase | 3'SL |

TABLE 2-continued

| Gene | Sequence ID (Gen Bank) | Description | HMO example |
| --- | --- | --- | --- |
| neuA | AF400048 | CMP-Neu5Ac synthetase | 3'SL, 6'SL |
| neuB | AF400048 | Sialic acid synthase | 3'SL, 6'SL, Sialic acid |
| neuC | AF400048 | GlcNAc-6-phosphate 2 epimerase | 3'SL, 6'SL, Sialic acid |

TABLE 3

| Gene | Sequence ID (UniProt) | Description | HMO products, examples |
| --- | --- | --- | --- |
| gmd | P0AC88 | GDP-mannose 4,6-dehydratase | 2'FL, 3'FL, DFL, LNFP-I, LNFP-II, LNFP-III, LNFP-V, LNFP-VI, LNDFH-I, LNDFH-II, F-pLNH I |
| wcaG | P32055 | GDP-fucose synthase | 2'FL, 3'FL, DFL, LNFP-I, LNFP-II, LNFP-III, LNFP-V, LNFP-VI, LNDFH-I, LNDFH-II, F-pLNH I |
| wcaH | P32056 | GDP-mannose mannosyl hydrolase | 2'FL, 3'FL, DFL, LNFP-I, LNFP-II, LNFP-III, LNFP-V, LNFP-VI, LNDFH-I, LNDFH-II, F-pLNH I |
| cpsB | P24174 | mannose-1-phosphate guanylyltransferase | 2'FL, 3'FL, DFL, LNFP-I, LNFP-II, LNFP-III, LNFP-V, LNFP-VI, LNDFH-I, LNDFH-II, F-pLNH I |
| cpsG | P24175 | phosphomannomutase | 2'FL, 3'FL, DFL, LNFP-I, LNFP-II, LNFP-III, LNFP-V, LNFP-VI, LNDFH-I, LNDFH-II, F-pLNH I |
| glmS | P17169 | L-glutamine-D-fructose-6-phosphate aminotransferase | LNT, LNnT, LNFP-I, LNFP-II, LNFP-III, LNFP-V, LNFP-VI, LNDFH-I, LNDFH-II, pLNH, F-pLNH I, pLNnH, 3'SL, 6'SL |
| glmU | P0ACC7 | fused N-acetylglucosamine-1-phosphate uridyltransferase and glucosamine-1-phosphate acetyltransferase | LNT, LNnT, LNFP-I, LNFP-II, LNFP-III, LNFP-V, LNFP-VI, LNDFH-I, LNDFH-II, pLNH, F-pLNH I, pLNnH, 3'SL, 6'SL |
| glmM | P31120 | phosphoglucosamine mutase | LNT, LNnT, LNFP-I, LNFP-II, LNFP-III, LNFP-V, LNFP-VI, LNDFH-I, LNDFH-II, pLNH, F-pLNH I, pLNnH, 3'SL, 6'SL |
| ampG | P0AE16 | muropeptide:H$_+$ symporter | LNT, LNnT, LNFP-I, LNFP-II, LNFP-III, LNFP-V, LNFP-VI, LNDFH-I, LNDFH-II, pLNH, F-pLNH I, pLNnH, 3'SL, 6'SL |
| nagA | P0AF18 | N-acetylglucosamine-6-phosphate deacetylase | LNT, LNnT, LNFP-I, LNFP-II, LNFP-III, LNFP-V, LNFP-VI, LNDFH-I, LNDFH-II, pLNH, F-pLNH I, pLNnH, 3'SL, 6'SL |
| nagK | P75959 | N-acetyl-D-glucosamine kinase | LNT, LNnT, LNFP-I, LNFP-II, LNFP-III, LNFP-V, LNFP-VI, LNDFH-I, LNDFH-II, pLNH, F-pLNH I, pLNnH, 3'SL, 6'SL |
| nagZ | P75949 | β-N-acetylhexosaminidase | LNT, LNnT, LNFP-I, LNFP-II, LNFP-III, LNFP-V, LNFP-VI, LNDFH-I, LNDFH-II, pLNH, F-pLNH I, pLNnH, 3'SL, 6'SL |
| phop | P23836 | DNA-binding transcriptional dual regulator PhoP | LNT, LNnT, LNFP-I, LNFP-II, LNFP-III, LNFP-V, LNFP-VI, LNDFH-I, LNDFH-II, pLNH, F-pLNH I, pLNnH, 3'SL, 6'SL |
| glnA | P0A9C5 | glutamine synthetase | LNT, LNnT, LNFP-I, LNFP-II, LNFP-III, LNFP-V, LNFP-VI, LNDFH-I, LNDFH-II, pLNH, F-pLNH I, pLNnH, 3'SL, 6'SL |
| ppk | P0A7B1 | polyphosphate kinase | LNT, LNnT, LNFP-I, LNFP-II, LNFP-III, LNFP-V, LNFP-VI, LNDFH-I, LNDFH-II, pLNH, F-pLNH I, pLNnH, 3'SL, 6'SL |
| pykA | P21599 | pyruvate kinase II | LNT, LNnT, LNFP-I, LNFP-II, LNFP-III, LNFP-V, LNFP-VI, LNDFH-I, LNDFH-II, pLNH, F-pLNH I, pLNnH, 3'SL, 6'SL |

TABLE 3-continued

| Gene | Sequence ID (UniProt) | Description | HMO products, examples |
|---|---|---|---|
| pgm | P36938 | phosphoglucomutase | LNT, LNnT, LNFP-I, LNFP-II, LNFP-III, LNFP-V, LNFP-VI, LNDFH-I, LNDFH-II, pLNH, F-pLNH I, pLNnH |
| galU | P0AEP3 | UTP-glucose-1-phosphate uridylyltransferase | LNT, LNnT, LNFP-I, LNFP-II, LNFP-III, LN FP-V, LN FP-VI, LNDFH-I, LNDFH-II, pLNH, F-pLNH I, pLNnH |
| galE | P09147 | UDP-glucose 4-epimerase | LNT, LNnT, LNFP-I, LNFP-II, LNFP-III, LNFP-V, LNFP-VI, LNDFH-I, LNDFH-II, pLNH, F-pLNH I, pLNnH |
| nagC | P0AF20 | DNA-binding transcriptional dual regulator NagC | LNT, LNnT, LNFP-I, LNFP-II, LNFP-III, LNFP-V, LNFP-VI, LNDFH-I, LNDFH-II, pLNH, F-pLNH I, pLNnH, 3'SL, 6'SL |
| glK | P0A6V8 | glucokinase | 2'FL, 3'FL, DFL, LNFP-I, LNFP-II, LNFP-III, LNFP-V, LNFP-VI, LNDFH-I, LNDFH-II, F-pLNH I |
| pfkB | P06999 | 6-phosphofructokinase II | 2'FL, 3'FL, DFL, LNFP-I, LNFP-II, LNFP-III, LNFP-V, LNFP-VI, LNDFH-I, LNDFH-II, F-pLNH I |
| gpt | P0A9M5 | xanthine-guanine phosphoribosyltransferase | 2'FL, 3'FL, DFL, LNFP-I, LNFP-II, LNFP-III, LNFP-V, LNFP-VI, LNDFH-I, LNDFH-II, F-pLNH I |
| gmk | P60546 | guanylate kinase | 2'FL, 3'FL, DFL, LNFP-I, LNFP-II, LNFP-III, LNFP-V, LNFP-VI, LNDFH-I, LNDFH-II, F-pLNH I |
| ndk | P0A763 | nucleoside diphosphate kinase | 2'FL, 3'FL, DFL, LNFP-I, LNFP-II, LNFP-III, LNFP-V, LNFP-VI, LNDFH-I, LNDFH-II, F-pLNH I |
| zwf | P0AC53 | $NADP_+$-dependent glucose-6-phosphate dehydrogenase | 2'FL, 3'FL, DFL, LNFP-I, LNFP-II, LNFP-III, LNFP-V, LNFP-VI, LNDFH-I, LNDFH-II, F-pLNH I |
| galF | P0AAB6 | UTP:glucose-1-phosphate uridylyltransferase | LNT, LNnT, LNFP-I, LNFP-II, LNFP-III, LNFP-V, LNFP-VI, LNDFH-I, LNDFH-II, pLNH, F-pLNH I, pLNnH |

The term "human milk oligosaccharide" or "HMO" in the present context means a complex carbohydrate found in human breast milk (for ref see Urashima et al.: *Milk Oligosaccharides*. Nova Science Publisher (2011); or Chen, *Adv. Carbohydr. Chem. Biochem.* 72, 113 (2015)). The HMOs have a core structure comprising a lactose unit at the reducing end that can be elongated by one or more β-N-acetyl-lactosaminyl and/or one or more β-lacto-N-biosyl units, and this core structure can be substituted by an α L-fucopyranosyl and/or an α-N-acetyl-neuraminyl (sialyl) moiety. In this regard, the non-acidic (or neutral) HMOs are devoid of a sialyl residue, and the acidic HMOs have at least one sialyl residue in their structure. The non-acidic (or neutral) HMOs can be fucosylated or non-fucosylated. Examples of such neutral non-fucosylated HMOs include lacto-N-tetraose (LNT), lacto-N-neotetraose (LNnT), lacto-N-neohexaose (LNnH), para-lacto-N-neohexaose (pLNnH), para-lacto-N-hexaose (pLNH) and lacto-N-hexaose (LNH). Examples of neutral fucosylated HMOs include 2'-fucosyllactose (2'-FL), lacto-N-fucopentaose I (LNFP-I), lacto-N-difucohexaose I (LNDFH-I), 3-fucosyllactose (3-FL), difucosyllactose (DFL), lacto-N-fucopentaose II (LNFP-II), lacto-N-fucopentaose III (LNFP-III), lacto-N-difucohexaose III (LNDFH-III), fucosyl-lacto-N-hexaose II (FLNH-II), lacto-N-fucopentaose V (LNFP-V), lacto-N-difucohexaose II (LNDFH-II), fucosyl-lacto-N-hexasoe I (FLNH-I), fucosyl-para-lacto-N-hexaose I (FpLNH-I), fucosyl-para-lacto-N-neohexaose II (F-pLNnH II) and fucosyl-lacto-N-neohexaose (FLNnH). Examples of acidic HMOs include 3'-sialyllactose (3'-SL), 6'-sialyllactose (6'-SL), 3-fucosyl-3'-sialyllactose (FSL), 3'-O-sialyllacto-N-tetraose a (LST a), fucosyl-LST a (FLST a), 6'-O-sialyllacto-N-tetraose b (LST b), fucosyl-LST b (FLST b), 6'-O-sialyllacto-N-neotetraose (LST c), fucosyl-LST c (FLST c), 3'-O-sialyllacto-N-neotetraose (LST d), fucosyl-LST d (FLST d), sialyl-lacto-N-hexaose (SLNH), sialyl-lacto-N-neohexaose I (SLNH-I), sialyl-lacto-N-neohexaose II (SLNH-II) and disialyl-lacto-N-tetraose (DSLNT). In the context of the present invention lactose is regarded as an HMO species.

The term "HMO precursor" in the present context refers to a compound being involved in the biosynthetic pathway of one or more HMOs according to the invention, which are produced and naturally present in the host cell or imported into the cell from the extracellular medium. Some non-limiting examples of HMO precursors are listed below:

| Precursor: | Product: |
|---|---|
| UDP-GlcNAc | LNT, LNnT, LNFP-I, LNFP-II, LNFP-III, LNFP-V, LNFP-VI, LNDFH-I, LNDFH-II, pLNH, F-pLNH I, 3'SL, 6'SL, pLNnH, (F)LSTa, (F)LSTb, (F)LSTc, (F)LSTd |
| UDP-Gal | LNT, LNnT, LNFP-I, LNFP-II, LNFP-III, LNFP-V, LNFP-VI, LNDFH-I, LNDFH-II, pLNH, F-pLNH I, pLNnH, LSTa, LSTb, LSTc, LSTd |
| GDP-fucose | LNT, LNnT, LNFP-I, LNFP-II, LNFP-III, LNFP-V, LNFP-VI, LNDFH-I, LNDFH-II, F-pLNH I, 2'FL, 3'FL, DFL, FLSTa, FLSTb, FLSTc, FLSTd |

The term "HMO transporter" means a biological molecule, e.g. protein, that facilitates transport/export an HMO synthesized by the host cell through a cellular membrane, e.g. into the cell medium, or transport/import of an HMO from the cell medium into the cell cytosol.

The term "HMO derivative" means a molecule that is derived from an HMO molecule or comprise an HMO moiety, e.g. a ganglioside molecule, an artificial carbohydrate/protein structure comprising an HMO moiety.

An expression cassette of the invention may be utilized for recombining production of one or more HMOs either as genome integrated or plasmid-borne, or, in some embodiments, the host cell may comprise both a genome integrated and a plasmid-borne expression cassette, wherein at least one or both of the expression cassettes comprise one or more genes that are essential and/or beneficial for the production of one or more HMOs and wherein the expression of at least one of said genes is under the control of a glp promoter of the invention (i.e. PglpF, PglpA. PglpD or PglpT, preferably, PglpF). Preferably, a genome integrated cassette comprises at least one (or a first set of) coding DNA sequences, and the plasmid-borne cassette comprises at least one second coding DNA (or a second set of coding DNA sequences), wherein the at least one first and/or at least one second coding DNA sequences are operably linked to a glp promoter of the invention. In some preferred embodiments, at least one of the expression cassettes is expressed under control of a Pglp, e.g. a coding sequence of the genome integrated cassette is operably linked to a glp promoter of the invention, e.g. PglpF, and the plasmid-borne coding sequence is operably linked to another promoter, e.g. lac promoter or another promoter. In some embodiments, both genome integrated, and plasmid-borne cassettes may be expressed under the control of the same or different glp promoter of the invention, e.g. the promoter of a genome integrated cassette is PglpF and the plasmid-borne promoter is PglpA. In other embodiments, all expression cassettes comprised in the host cell may comprise the same glp promoter. In one preferred embodiment, the host cell comprises at least one copy of a genome-integrated expression cassette of the invention comprising PglpF. Preferably, the host cell genome comprises a single or low number of copies of the genome integrated expression cassette, such as two or three copies. Still, in some embodiments, the host may comprise multiple copies of an expression plasmid, wherein each plasmid comprises a single copy of an expression cassette of the invention. In some embodiments, the host cell may comprise several different nucleic acid constructs of the invention, both/either genome integrated and/or plasmid-borne. Each of the several different nucleic acid constructs may be integrated in the genome of the host cell or into a plasmid in a single or multiple copy. In some embodiments, it is preferred that the constructs are integrated in a single copy or a low copy number.

According to the invention, a single copy of the expression cassette of invention comprised in a host cell either as genome integrated or plasmid-borne can provide an amount of a biological molecule encoded by the coding DNA sequence (ii) (preferably, under control of a glp promoter, e.g. PglpF), that is sufficient to secure high production levels of one or more HMOs by the host cell. Surprisingly, a single genome-integrated copy of an expression cassette of the invention can provide the production levels of an HMO that are comparable to or higher (such as 2-10-fold higher) than the production levels achieved using a high number plasmid-borne expression (100-500 copies) of the same cassette. In some embodiments, it may be advantageous to express two or more genes related to the HMO production in in the host cell. The HMO-related genes may be included in one construct and expressed as tandem from a single (or multiple) copy as genome- or plasmid-borne; or the genes may be included in different constructs of the invention and one gene is expressed from the genome integrated cassette and another gene from the plasmid-borne. In other embodiments, other mode of expression, composition, or number of copies of the expression cassettes may be contemplated. Preferably, at least one gene included in later expression cassettes encodes for a protein with an enzymatic activity that is essential for the synthesis of an HMO in the host cell. Non-limiting embodiments of genes that may advantageously be expressed under the control of a glp promoter are described in Tables 2 and 3 and in working examples.

According with the above, a second aspect of the invention relates to a recombining cell comprising a nucleic acid construct of the invention. The recombining cell is interchangeably termed herein as host cell. Preferably, the host cell is a bacterial cell. The terms "host bacteria species", "host bacterial cell" are used interchangeably to designate a bacterial cell that has been transformed to contain a DNA construct of the invention and is capable to express the heterologous polypeptide encoded by corresponding heterologous coding DNA sequence of the construct. The terms "transformation", "transformed", and "transplanted" are synonymous and denote a process wherein an extracellular nucleic acid, like a vector comprising a construct of the invention, with or without accompanying material, enters a host cell. Transformation of appropriate host cells with, for example, an expression vector can be accomplished by well-known methods such as, electroporation, conjugation, or by chemical methods such as Calcium phosphate-mediated transformation and by natural transformation systems, described, for example, in Maniatis et al., or in Ausubel et al.

Regarding the bacterial host cells, there are, in principle, no limitations; they may be eubacteria (gram-positive or gram-negative) or archaebacteria, as long as they allow genetic manipulation for insertion of a gene of interest and can be cultivated on a manufacturing scale. Preferably, the host cell has the property to allow cultivation to high cell densities. Non-limiting examples of bacterial host cells that are suitable for recombining industrial production of an HMO(s) according to the invention could be *Erwinia herbicola* (*Pantoea agglomerans*), *Citrobacter freundii*, *Pantoea citrea*, *Pectobacterium carotovorum*, or *Xanthomonas campestris*. Bacteria of the genus *Bacillus* may also be used, including *Bacillus subtilis*, *Bacillus licheniformis*, *Bacillus coagulans*, *Bacillus thermophilus*, *Bacillus laterosporus*, *Bacillus megaterium*, *Bacillus mycoides*, *Bacillus pumilus*, *Bacillus lentus*, *Bacillus cereus*, and *Bacillus circulans*. Similarly, bacteria of the genera *Lactobacillus* and *Lactococcus* may be modified using the methods of this invention, including but not limited to *Lactobacillus acidophilus*, *Lactobacillus salivarius*, *Lactobacillus plantarum*, *Lactobacillus helveticus*, *Lactobacillus delbrueckii*, *Lactobacillus rhamnosus*, *Lactobacillus bulgaricus*, *Lactobacillus crispatus*, *Lactobacillus gasseri*, *Lactobacillus casei*, *Lactobacillus reuteri*, *Lactobacillus jensenii*, and *Lactococcus lactis*. *Streptococcus thermophiles* and *Proprionibacterium freudenreichii* are also suitable bacterial species for the invention described herein. Also included as part of this invention are strains, modified as described here, from the genera *Enterococcus* (e.g., *Enterococcus faecium* and *Enterococcus thermophiles*), *Bifidobacterium* (e.g., *Bifidobacterium longum*, *Bifidobacterium infantis*, and *Bifidobacterium bifidum*), *Sporolactobacillus* spp., *Micromomospora* spp., *Micrococcus* spp., *Rhodococcus* spp., and *Pseudomonas* (e.g., *Pseudomonas fluorescens* and *Pseudomonas aeruginosa*). Bacteria comprising the characteristics described herein are cultured in the presence of lactose, and an HMO produced by the cell is retrieved, either from the bacterium itself or from a culture supernatant of the bacterium. The HMO is purified using a suitable procedure available in the art (e.g. such as described in WO2015188834, WO2017182965 or WO2017152918).

In a preferred embodiment, the host cell is *E. coli*. However, as mentioned, a variety of host cells can be used for the purposes of the invention.

One requirement to the host cell is that it contains a functional DNA-dependent RNA polymerase that can bind to the promoter and initiate transcription of the DNA of the construct. The RNA polymerase may be endogenous (native), homologous (recombining) or foreign/heterologous (recombining) to the host cell.

The construct of the invention transformed into a selected bacterial host can be expressed as a genome integrated expression cassette or cloned into a suitable expression vector and expressed as plasmid-borne. In different embodiments it may be preferred to utilize the genome-based expression system, in other embodiments, the plasmid-born expression may be preferred. However, it is an advantage to use the construct of the invention in the genome-based expression system, as, surprisingly, a single copy of the construct integrated into and expressed from the genome can provide a high and stable level of expression of the integrated gene product. In additional advantage is that the genomic expression is sustainable for long periods of time. For the purposes of the invention there can be used standard methods for integration of the constructs of invention into the host cell genome or into expression plasmids which are e.g. described in Sambrook et al., Wilson & Walker, "Maniatise et al, and *Ausubel* et al.

The terms "transformation", "transformed", and "transplanted" are synonymous and denote a process wherein an extracellular nucleic acid, like a vector comprising a construct of the invention, with or without accompanying material, enters a host cell. Transformation of appropriate host cells with, for example, an expression vector can be accomplished by well-known methods such as, electroporation, conjugation, or by chemical methods such as Calcium phosphate—mediated transformation and by natural transformation systems, described, for example, in Maniatis et al., or in Ausubel et al.

For the genome-based expression, there is a requirement to a host cell—the cell should be able to carry out homologous recombination (which is relevant for integration of the expression cartridge into the genome). Therefore, the host cell preferably carries the function of the recombination protein RecA. However, since RecA may cause undesirable recombination events during cultivation, the host cell preferably has a genomic mutation in its genomic recA site (rendering it dysfunctional), but has instead the RecA function provided by a recA sequence present on a helper plasmid, which can be removed (cured) after recombination by utilizing the helper plasmid's temperature-sensitive replicon (Datsenko K. A. and Wanner B. L., (2000) *Proc Natl Acad Sci USA*. 97(12):6640-5). In view of recombination, in addition to RecA, the host cell preferably contains, DNA sequences encoding recombination proteins (e.g. Exo, Beta and Gam). In this case, a host cell may be selected that already has this feature, or a host cell is generated de novo by genetic engineering to insert these sequences.

With regard to the integration locus, the expression system used in the invention allows for a wide variability. In principle, any locus with known sequence may be chosen, with the proviso that the function of the sequence is either dispensable or, if essential, can be complemented (as e.g. in the case of an auxotrophy). Many integration loci suitable for the purposes of the invention are described in the prior art (see e.g. Francia V M & Lobo J M G (1996), *J. Bacteriol* v 178 p. 894-898: Juhas M et al (2014) doi.org/10.1371/journal.pone.0111451; Juhas M & Aijoka F W (2015) *Microbal Biothechnol* v. 8:617-748; Sabi A et al (2013) *Microbial Cell Factories* 12:60).

The DNA construct may also be inserted sited-specific. In view of site-specific gene insertion, another requirement to the host cell is that it contains at least one genomic region (either a coding or any non-coding functional or non-functional region or a region with unknown function) that is known by its sequence and that can be disrupted or otherwise manipulated to allow insertion of a heterologous sequence, without being detrimental to the cell.

In certain embodiments, the host cell carries, in its genome, a marker gene in view of selection.

When choosing the integration locus, it needs to be considered that the mutation frequency of DNA caused by the so-called "adaptive evolution" varies across the genome of *E. coli* and that the metabolic load triggered by chromosomally encoded recombining gene expression may cause an enhanced mutation frequency at the integration site. In order to obtain an expression host cell that is robust and stable, a highly conserved genomic region that results in a lowered mutation frequency is preferably selected as integration site. Such highly conserved regions of the *E. coli* genome are for instance the genes encoding components of the ribosome or genes involved in peptidoglycan biosynthesis, and those regions may be preferably selected for integration of the expression cartridge. The exact integration locus is thereby selected in such a way that functional genes are neither destroyed nor impaired, and the integration site should rather be located in non-functional regions.

The genomic region with known sequence that can be chosen for integration of the cartridge may be selected from the coding region of a non-essential gene or a part thereof;

from a dispensable non-coding functional region (i.e. promoter, transposon, etc.), from genes the deletion of which may have advantageous effects in view of production of a specific protein of interest, e.g. certain proteases, outer membrane proteins, potential contaminants of the product, genes encoding proteins of metabolism (e.g. relevant for the metabolism of a sugar molecule that is undesirable or dispensable for a given host strain and/or fermentation process) or stress signaling pathways, e.g. those occurring in stringent response, a translational control mechanism of prokaryotes that represses tRNA and rRNA synthesis during amino acid starvation. Alternatively, the site of integration may be a marker gene which allows selection for disappearance of said marker phenotype after integration. Alternatively, the site useful to select for integration is a function which, when deleted, provides an auxotrophy, i.e. the inability of an organism to synthesize a particular organic compound required for its growth. In this case, the integration site may be an enzyme involved in biosynthesis or metabolic pathways, the deletion of such enzyme resulting in an auxotrophic strain. Positive clones, i.e. those carrying the expression cassette, may be selected for auxotrophy for the substrate or precursor molecules of said enzymes. Alternatively, the site of integration may be an auxotrophic marker (a non-functional, i.e. defective gene) which is replaced/complemented by the corresponding prototrophic marker (i.e. a sequence that complements or replaces the defective sequence) present on the expression cassette, thus allowing for prototrophic selection.

In one aspect, the region is a non-essential gene. According to one aspect, this may be a gene that is per se non-essential for the cell. Non-essential bacterial genes are known from the literature, e.g. from the PEC (Profiling the E. coli Chromosome) database http://www.shigen.nig.ac.jp/ecoli/pec/genes.jsp) or from the so-called "Keio collection" (Baba et al., *Molecular Systems Biology* (2006) 2, 2006.0008). One example for a non-essential gene is RecA. Integrating the expression cassette at this site provides the genomic mutation described above in the context with the requirements on the host cells.

Suitable integration sites, e.g. sites that are easily accessible and/or are expected to yield higher expression rates, can be determined in preliminary screens. Such screens can be performed by generating a series of single mutant deletions according to the Keio collection (Baba et al., 2006) whereby the integration cartridge features, as variable elements, various recombination sequences that have been pre-selected in view of specific integration sites, and, as constant elements, the basic sequences for integration and selection, including, as a surrogate "gene of interest", a DNA sequence encoding an easily detectable protein under the control of an inducible promoter, e.g. the Green Fluorescent Protein. The expression level of the thus created single knockout mutants can be easily quantified by fluorescence measurement. Based on the results of this procedure, a customized expression level of a desired target protein can be achieved by variation of the integration site and/or number of integrated cartridges.

In the embodiments in which the host cell contains DNA sequences encoding recombination proteins (e.g. Exo, Beta and Gam—either as a feature of the starting cell or obtained by genetic engineering—integration can occur at the genomic site where these recombination protein sequences are located. By integration of the expression cartridge, the sequences coding for the recombination proteins are destroyed or removed and consequently need not, as in the case of plasmid-encoded helper proteins, be removed in a separate step.

Integration of the gene of interest into the bacterial genome can be achieved by conventional methods, e.g. by using linear cartridges that contain flanking sequences homologous to a specific site on the chromosome, as described for the attTn7-site (Waddell C. S. and Craig N. L., *Genes Dev.* (1988) February; 2(2):137-49.); methods for genomic integration of nucleic acid sequences in which recombination is mediated by the Red recombinase function of the phage λ or the RecE/RecT recombinase function of the Rac prophage (Murphy, *J Bacteriol.* (1998); 180(8): 2063-7; Zhang et al., *Nature Genetics* (1998) 20: 123-128 Muyrers et al., *EMBO Rep*. (2000) 1(3): 239-243); methods based on Red/ET recombination (Wenzel et al., *Chem Biol*. (2005), 12(3):349-56.; Vetcher et al., *Appl Environ Microbiol*. (2005); 71(4):1829-35).

Positive clones, i.e. clones that carry the expression cassette, can be selected e.g. by means of a marker gene, or loss or gain of gene function.

In some embodiments, host cells are used that already contain a marker gene integrated in their genome, e.g. an antibiotic resistance gene or a gene encoding a fluorescent protein, e.g. GFP. In this case, the expression cartridge which does not contain a selection marker, is integrated at the locus of the chromosomal marker gene, and positive clones are selected for loss/disappearance of the respective phenotype, e.g. they are selected for antibiotic sensitivity or disappearance of fluorescence, which can be directly visualized on the cultivation plates. These embodiments have the advantage that the marker is either interrupted or completely replaced by the expression cassette, and thus no functional marker sequence is present after integration and does not need to be removed, if undesirable, as in the case of antibiotic resistance genes.

Alternatively, the marker gene is part of the expression cartridge. In the case that the marker used for selection is a gene conferring antibiotic resistance (e.g. for kanamycin or chloramphenicol), positive clones are selected for antibiotic resistance (i.e. growth in the presence of the respective antibiotic). The marker gene (irrespective of whether it is present on the host cell's genome or has been introduced by means of the expression cartridge) can be eliminated upon integration of the cassette.

In certain embodiments, the expression cell may be engineered to carry a defective selectable marker gene, e.g. an antibiotic resistance gene like chloramphenicol or kanamycin, a fluorescent marker or a gene involved in a metabolic pathway of a sugar or an amino acid. In this case, the cartridge with the gene of interest carries the missing part of the marker gene, and by integration the marker gene restores its functionality. By way of example, the cartridge carries the missing part of the marker gene at one of its ends and is integrated directly adjacent to the defective marker gene integrated in the genome, such that the fusion of the two fragments renders the marker gene complete and allows its functional expression. In the case of an antibiotic resistance gene, the cells carrying the expression cassette are resistant against the specific antibiotic, in the case of a fluorescent marker cells can be visualized by fluorescence, and in the case of a metabolic pathway gene, cells obtain the ability to metabolize the respective component. The advantage of this embodiment is that only a short proportion of the marker gene of the cartridge needs to be synthesized, enabling shorter or smaller insertion cartridges compared to prior art.

In certain embodiments, selection of positive clones (i.e. clones that carry the expression cassette) may be carried out by correction (i.e. complementation) of an auxotrophy of the host cell. In such embodiments, a host cell is used that has a mutation that has been chosen to allow selection of positive transformant colonies in an easy way, e.g. a strain that has a deletion or mutation that renders it unable to synthesize a compound that is essential for its growth (such mutation being termed as "auxotrophic marker"). For example, a bacterial mutant in which a gene of the proline synthesis pathway is inactivated, is a proline auxotroph. Such a strain is unable to synthesize proline and will therefore only be able to grow if proline can be taken up from the environment, as opposed to a proline prototroph which can grow in the absence of proline.

Any host cell having an auxotrophic marker may be used. Preferably, mutations in genes required for amino acid synthesis are used as auxotrophic markers, for instance mutations in genes relevant for the synthesis of proline, leucine or threonine, or for co-factors like thiamine. According to the invention, the auxotrophy of host cells is corrected by integration of the missing/defective gene as a component of the expression cartridge into the genome along with integration of the gene of interest. The thus obtained prototrophic cells can be easily selected by growing them on a so-called "minimal medium" (prototrophic selection), which does not contain the compound for which the original host cell is auxotroph, thus allowing only positive clones to grow.

Prototrophic selection is independent of the integration locus. The integration locus for prototrophic selection may be any gene in the genome or at the locus carrying the auxotrohic marker. The particular advantage of prototrophic selection is that no antibiotic resistance marker nor any other marker that is foreign to the host remains in the genome after successful integration. Consequently, there is no need for removal of said marker genes, providing a fast and simple cloning and selection procedure. Another advantage is that restoring the gene function is beneficial to the cell and provides a higher stability of the system.

Alternatively, the marker gene that is inserted into the genome together with the expression cartridge, may be a metabolic gene that allows a particular selection mode. Such a metabolic gene may enable the cell to grow on particular (unusual) sugar or other carbon sources, and selection of positive clones can be achieved by growing cells on said sugar as the only carbon source.

As described above, during long term cultivation of bacteria, adaptive evolution may cause an enhanced mutation frequency at the integration site during expression of the chromosomally encoded recombining protein. The use of an auxotrophic knockout mutant strain in combination with an expression cartridge complementing the lacking function of the mutant strain (thereby generating a prototroph strain from an auxotroph mutant) has the additional advantage that the restored gene provides benefits to the cell by which the cell gains a competitive advantage such that cells in which adaptive evolution has occurred are repressed. Thereby, a means of negative selection for mutated clones is provided.

In some embodiments (in the case that the protein of interest allows for detection on a single-cell or single-colony basis, e.g. by FACS analysis or immunologically (ELISA)), no marker gene is required, since positive clones can be determined by direct detection of the protein of interest.

The integration methods for obtaining the expression host cell are not limited to integration of one gene of interest at one site in the genome; they allow for variability with regard to both the integration site and the expression cassettes. By way of example, more than one genes of interest may be inserted, i.e. two or more identical or different sequences under the control of identical or different promoters can be integrated into one or more different loci on the genome. By way of example, it allows expression of two different proteins that form a heterodimeric complex. Heterodimeric proteins consist of two individually expressed protein subunits. One example of such protein is an antibody molecule, e.g. the heavy and the light chain of a monoclonal antibody or an antibody fragment; other examples of heterodimeric proteins are CapZ, Ras human DNA helicase II, etc. These two sequences encoding the monomers may be present on one expression cartridge which is inserted into one integration locus. Alternatively, these two sequences may also be present on two different expression cartridges, which are inserted independently from each other at two different integration loci. In any case, the promoters and the induction modes may be either the same or different.

Although the invention allows and can advantageously be practiced for plasmid-free production of biological molecules of interest encoded by the gene of the construct of the invention, it does not exclude that in the expression system of the invention comprises a plasmid that carries sequences to be expressed other than the gene of interest, e.g. the helper proteins and/or the recombination proteins described above. Naturally, care should be taken that in such embodiments the advantages of the invention should not be overruled by the presence of the plasmid, i.e. preferably, such plasmid should be present at a low copy number and should not exert a metabolic burden onto the cell.

The expression system useful in the method of the invention may be designed such that it is essentially or completely free of phage functions.

Summarizing the above embodiments, genome-based expression of the expression cassette of the invention provides the following major advantages:

With respect to the construction procedure of the expression host, the advantages are (i) a simple method for synthesis and amplification of the linear insertion cartridge, (ii) a high degree of flexibility (i.e. no limitation) with respect to the integration locus, (iii) a high degree of flexibility with respect to selection marker and selection principle, (iv) the option of subsequent removal of the selection marker, (v) the discrete and defined number of inserted expression cartridges (usually one or two).

Integration of one or more recombining genes into the genome results in a discrete and pre-defined number of genes of interest per cell. In the embodiment of the invention that inserts one copy of the gene, this number is usually one (except in the case that a cell contains more than one genomes, as it occurs transiently during cell division), as compared to plasmid-based expression which is accompanied by copy numbers up to several hundred. In the expression system used in the method of the present invention, by relieving the host metabolism from plasmid replication, an increased fraction of the cell's synthesis capacity is utilized for recombining protein production. A strong expression element of the construct, e.g. Pglp, such as PglpF, PglpA, PglpD or PglpT, can be applied without adverse effects on host metabolism by reduction of the gene dosage.

As mentioned above, plasmid-based expression systems have the drawback that, during cell division, cells may lose the plasmid and thus the gene of interest. Such loss of plasmid depends on several external factors and increases with the number of cell divisions (generations). This means that plasmid-based fermentations are limited with regard to the number of generations (in conventional fermentations, this number is approximately between 20 and 50). In contrast, the genome-based expression system used in the method of the invention ensures a stable, pre-defined gene dosage for a practically infinite number of generations and thus theoretically infinite cultivation time under controlled conditions (without the disadvantage of the occurrence of cells that do not produce the protein of interest and with the only limitation of potentially occurring natural mutations as they may occur in any gene).

In the case of chemically-inducible promoters, the invention provides the particular advantage that the amount of inducer molecule, when e.g. added in a continuous mode, is directly proportional to the gene dosage per cell, either constant over the entire cultivation, or changing over cultivation time at pre-defined values. Thereby control of the recombining expression rate can be achieved, which is of major interest to adjust the gene expression rate.

Since the genome-based expression system allows exact control of protein expression, it is particularly advantageous in combination with expression targeting pathways that depend or rely on well-controlled expression.

As described above, the invention allows to design simplified processes, improved process predictability and high reproducibility from fermentation to fermentation. The process of the invention, employing the expression system described above, may be conducted in the fed-batch or in the semi-continuous or continuous mode, whereby the advantages of the genome-encoded expression system are optimally exploited. There are no limitations with respect to process parameters such as growth rate, temperature and culture medium components, except as defined by the host cell's requirements and as pre-defined by the selected promoter.

Another advantage relates to the choice of the inducer molecule: Most of the available systems for high-level expression of recombining genes in E. coli are lac-based promoter-operator systems inducible by IPTG. The expression system used in the invention allows a carbon-limited cultivation, with continuous or pulse supply of the carbon-source, e.g. lactose, and enables a tight expression rate control with a wide range of unexpansive carbon-source inducers, such as glycerol, fucose, lactose, glucose.

Importantly, the expression system used in the invention has the advantage of providing a high yield of recombinantly produced biological molecules, both regarding the molecule concentration per volume culture medium (i.e. the titer) and regarding the molecule content in the obtained biomass. This feature makes the expression system used in the invention superior compared to prior art expression systems.

Furthermore, the invention offers the advantage that selection of the expression host cell and/or the optimal design of the expression cartridge, can be easily achieved in preliminary screening tests. By way of example, in such preliminary screens a series of linear expression cartridges that vary with respect to at least one element that has an impact on expression properties of the protein of interest (expression level or qualitative features like biological activity), i.e. control elements (e.g. promoter and/or polymerase binding site) and/or sequence of the gene of interest (i.e. different codon usage variants) and/or targeting sequences for recombination and/or any other elements on the cartridge, like secretion leaders, is constructed. The cartridge variants are integrated into the genome of a pre-selected host cell and the resulting expression host variants are cultivated, including induction of protein expression, under controlled conditions. By comparing protein expression, the host cell variant showing the most favorable results in view of an industrial manufacturing process is selected. In a variation of this pre-screening approach, instead of determining the optimal expression cartridge, the optimal bacterial strain may be identified by integrating identical cartridges into a panel of different host cells. Since the integration strategy has the advantage of allowing integration of a discrete number of gene copies (e.g. only one) into the genome, pre-screening of various parameters may be done without interference by plasmid replication or changes in plasmid copy number.

According to the invention, the term "cultivating" (or "cultivation", also termed "fermentation") relates to the propagation of bacterial expression cells in a controlled bioreactor according to methods known in the industry.

Manufacturing of recombining proteins is typically accomplished by performing cultivation in larger volumes. The term "manufacturing" and "manufacturing scale" in the meaning of the invention defines a fermentation with a minimum volume of 5 L culture broth. Usually, a "manufacturing scale" process is defined by being capable of processing large volumes of a preparation containing the recombining protein of interest and yielding amounts of the protein of interest that meet, e.g. in the case of a therapeutic protein, the demands for clinical trials as well as for market supply. In addition to the large volume, a manufacturing scale method, as opposed to simple lab scale methods like shake flask cultivation, is characterized by the use of the technical system of a bioreactor (fermenter) which is equipped with devices for agitation, aeration, nutrient feeding, monitoring and control of process parameters (pH, temperature, dissolved oxygen tension, back pressure, etc.). The behavior of an expression system in a lab scale method does not allow to predict the behavior of that system in the complex environment of a bioreactor.

The expression systems of the invention may be advantageously used for recombining production on a manufacturing scale (with respect to both the volume and the technical system) in combination with a cultivation mode that is based on feeding of nutrients, in particular a fed-batch process or a continuous or semi-continuous process.

In certain embodiments, the method of the invention is a fed-batch process.

Whereas a batch process is a cultivation mode in which all the nutrients necessary for cultivation of the cells are contained in the initial culture medium, without additional supply of further nutrients during fermentation, in a fed-batch process, after a batch phase, a feeding phase takes place in which one or more nutrients are supplied to the culture by feeding. The purpose of nutrient feeding is to increase the amount of biomass (so-called "High-cell-density-cultivation process" or "HCDC") in order to increase the amount of recombining protein as well. Although in most cultivation processes the mode of feeding is critical and important, the present invention is not restricted with regard to a certain mode of feeding.

Feeding of nutrients may be done in a continuous or discontinuous mode according to methods known in the art. The feeding mode may be pre-defined (i.e. the feed is added independently from actual process parameters), e.g. linear constant, linear increasing, step-wise increasing or following a mathematical function, e.g. exponential feeding.

In a preferred embodiment, the method of the invention is a fed-batch process, wherein the feeding mode is predefined according to an exponential function. By applying an exponential feeding mode, the specific growth rate p of the cell population can be pre-defined at a constant level and optimized with respect to maximum recombining protein expression. Control of the feeding rate is based on a desired specific growth rate μ. When a defined medium, as described below, is used, growth can be exactly predicted and pre-defined by the calculation of a biomass aliquot to be formed based on the substrate unit provided.

In another preferred embodiment, an exponential feeding mode may be followed, in the final stages of cultivation, by linear constant feeding.

In another embodiment of the fed-batch process, linear constant feeding is applied. Linear constant feeding is characterized by the feeding rate (volume of feed medium per time unit) that is constant (i.e. unchanged) throughout certain cultivation phases.

In another embodiment of the fed-batch process, linear increasing feeding is applied. Linear increasing feeding is characterized by a feeding rate of feed medium following a linear function. Feeding according to a linear increasing function is characterized by a defined increase of feeding rate per a defined time increment.

In another embodiment of the fed-batch process of the invention, a feedback control algorithm is applied for feeding (as opposed to a pre-defined feeding mode). In a feedback-controlled fed-batch process, the feeding rate depends on the actual level of a certain cultivation parameter. Cultivation parameters suitable for feedback-controlled feeding are for instance biomass (and chemical or physical parameters derived thereof), dissolved oxygen, respiratory coefficient, pH, or temperature. Another example for a feedback-controlled feeding mode is based on the actual glucose concentration in the bioreactor In another embodiment, bacterial cells carrying a genome-based expression cassette according to the present invention are cultivated in continuous mode. A continuous fermentation process is characterized by a defined, constant and continuous rate of feeding of fresh culture medium into the bioreactor, whereby culture broth is at the same time removed from the bioreactor at the same defined, constant and continuous removal rate. By keeping culture medium, feeding rate and removal rate at the same constant level, the cultivation parameters and conditions in the bioreactor remain constant (so-called "steady state"). The specific growth rate p can be pre-defined and is exclusively a result of the feeding rate and the culture medium volume in the bioreactor. Since cells having one or more genome-based expression cassettes are genetically very stable (as opposed to structurally and segregationally instable plasmid-based expression systems, or expression systems which genome-inserted cassette relies on genomic amplification), the number of generations (cell doublings) of cells according to the invention is theoretically unlimited, as well as, consequently, cultivation time. The advantage of cultivating a genetically stable genome-based expression system in a continuous mode is that a higher total amount of recombining protein per time period can be obtained, as compared to genetically unstable prior art systems. In addition, due to the theoretically unlimited time of cultivation, continuous cultivation of cells according to the invention may lead to a higher total protein amount per time period even compared to fed-batch cultivation processes. Non-limiting working examples below show the high stability and productivity of a genome-based expression construct.

Another preferred embodiment refers to semi-continuous cultivation of cells. A semi-continuous cultivation process in the meaning of the invention is a process which is operated in its first phase as a fed-batch process (i.e. a batch phase followed by a feeding phase). After a certain volume or biomass has been obtained (i.e. usually when the upper limit of fermenter volume is obtained), a significant part of cell broth containing the recombining protein of interest is removed from the bioreactor. Subsequently, feeding is initiated again until the biomass or volume of culture broth has again reached a certain value. This method (draining of culture broth and re-filling by feeding) can be proceeded at least once, and theoretically indefinite times.

With regard to the type of the culture medium used in the fermentation process, there are no limitations. The culture medium may be semi-defined, i.e. containing complex media compounds (e.g. yeast extract, soy peptone, casamino acids, etc.), or it may be chemically defined, without any complex compounds.

Preferably, a "defined medium" is used. "Defined" media (also termed "minimal" or "synthetic" media) are exclusively composed of chemically defined substances, i.e. carbon sources such as glucose or glycerol, salts, vitamins, and, in view of a possible strain auxotrophy, specific amino acids or other substances such as thiamine. Most preferably, glucose is used as a carbon source. Usually, the carbon source of the feed medium serves as the growth-limiting component which controls the specific growth rate.

In the methods of the invention, significantly higher yields are obtained, because growth of bacteria and a high, but physiologically tolerable recombining gene expression rate can be maintained during the whole production process.

As described above, in a most preferred embodiment of the invention, the protein of interest is under control of an "inducible" or "controllable" promoter.

There is no limitation as regards the mode by which induction of protein expression is performed. By way of example, the inductor can be added as a singular or multiple bolus or by continuous feeding, the latter being also known as "inductor feed(ing)". There are no limitations as regards the time point at which the induction takes place. The inductor may be added at the beginning of the cultivation or at the point of starting continuous nutrient feeding or after (beyond) the start of feeding. Inductor feeding may be accomplished by either having the inductor contained in the culture medium or by separately feeding it.

The advantage of inductor feeding is that it allows to control inductor dosage, i.e. it allows to maintain the dosage of a defined or constant amount of inductor per constant number of genes of interest in the production system. For instance, inductor feeding allows an inductor dosage which is proportional to the biomass, resulting in a constant ratio of inductor to biomass. Biomass units on which the inductor dosage can be based, may be for instance cell dry weight (CDW), wet cell weight (WCW), optical density, total cell number (TCN; cells per volume) or colony forming units (CFU per volume) or on-line monitored signals which are proportional to the biomass (e.g. fluorescence, turbidity, dielectric capacity, etc.). Essentially, the method of the invention allows the precise dosage of inductor per any parameter or signal which is proportional to biomass, irrespective of whether the signal is measured off-line or on-line. Since the number of genes of interest is defined and constant per biomass unit (one or more genes per cell), the consequence of this induction mode is a constant dosage of inductor per gene of interest. As a further advantage, the exact and optimum dosage of the amount of inductor relative to the amount of biomass can be experimentally determined and optimized.

It may not be necessary to determine the actual biomass level by analytical methods. For instance, it may be sufficient to add the inductor in an amount that is based on previous cultivations (historical biomass data). In another embodiment, it may be preferable to add the amount of inductor per one biomass unit as theoretically calculated or predicted. For instance, it is well known for feeding-based cultivations (like fed-batch or continuous) that one unit of the growth-limiting component in the feed medium, usually the carbon source, will result in a certain amount of biomass. As an example, 1 g glucose as growth-limiting substrate will result in approximately 0.33 g cell dry weight (also expressed by the substrate yield coefficient $Y_{x/s}$=0.33). Consequently, a defined dosage of inductor per gene of interest may also be achieved by the defined dosage of inductor per unit growth limiting-component, since a certain unit of growth limiting component results in a defined unit of biomass, and a defined unit of biomass contains a defined number of molecules of proteins of interest according to the method of the invention.

As an essential advantage, feeding limiting amounts of inductor prevents metabolic load and reduces stress in favor of maximizing the capacity of protein synthesis.

The ratio of inductor per biomass (or per gene or per unit growth-limiting substrate) may not necessarily be constant. It may also be linear increasing, linear decreasing, increasing or decreasing according to exponential or other mathematical functions, etc. The essential feature according to the invention is that the value of inductor dosage per gene of interest is defined.

In certain embodiments, the method of the invention is a fed-batch process, wherein the inductor is present in the batch medium from start of cultivation.

The mode of induction of expression can also be constitutive, which means that induction is not triggered chemically or by other stimuli, but that it is permanent from start of cultivation. Constitutive induction is the preferred induction mode for continuous cultivation, but also useful for fed-batch cultivation.

Recombinant bacteria and methods for producing HMOs are well known (see e.g. Priem B et al, (2002) Glycobiology; 12(4):235-40; Drouillard S et al, (2006) Angew. Chem. Int. Ed. 45:1778-1780; Fierfort N & Samain E (2008) J Biotechnol 134:261-265; Drouillard S. et al. (2010) Carbohydrate Research 345 1394-1399; Gebus C et al (2012) Carbohydrate Research 363 83-90).

Following the methods described in the art and according to the invention, a bacterial host may utilize an endogenous or exogenous guanosine diphosphate (GDP)-fucose synthesis pathway to produce a fucosylated HMO. By "GDP-fucose synthesis pathway" is meant a sequence of reactions, usually controlled and catalyzed by enzymes, which results in the synthesis of GDP-fucose. An exemplary GDP-fucose synthesis pathway in E. coli is set forth below. In this synthesis pathway, the enzymes for GDP-fucose synthesis include: 1) rnanA=phosphomannose isomerase (PMI), 2) manB=phosphomannomutase (PMM), 3) manC=mannose-1-phosphate guanylyltransferase (GMP), 4) gmd=GDP-mannose-4,6-dehydratase (GMD), 5) fcl=GDP-fucose synthase (GFS), and 6) ΔwcaJ=mutated UDP-glucose lipid carrier transferase.

Glucose→Glc-6-P→Fru-6-P→$^1$Man-6-P→$^2$MAN-1-P→$^3$GDP-Man-→$^{4,5}$GDP-Fuc$^6$Colanic acid.

The synthetic pathway from fructose-6-phosphate, a common metabolic intermediate of all organisms, to GDP-fucose consists of 5 enzymatic steps: 1) PMI (phosphomannose isomerase), 2) PMM (phosphomannomutase), 3) GMP (mannose-1-phosphate guanylyltransferase), 4) GMD (GDP-mannose-4,6-dehydratase), and 5) GFS (GDP-fucose synthase). In the context of the present invention, enzymes of the GDP-synthesis pathway that contribute to increasing the intracellular pool of GDP-fucose are included in the group of beneficial proteins that are indirectly involved in the HMO synthesis. Individual bacterial species possess different inherent capabilities with respect to GDP-fucose synthesis. E. coli, for example, can synthesize enzymes that are competent to perform all five steps, whereas Bacillus licheniformis is missing enzymes capable of performing steps 4 and 5 (i.e., GMD and GFS). Any enzymes in the GDP-synthesis pathway that are inherently missing in any particular bacterial species may be introduced to the host by molecular engineering involving recombining DNA constructs of the invention. Genes encoding for the missing enzymes can be supplied either on a plasmid expression vector or as exogenous genes integrated into the host chromosome (the enzymes of the GDP-synthesis pathway are, in the context of the invention, enzymes that are indirectly involved in the HMO production, i.e. enzymes essential for the HMO production).

A bacterium suitable for the HMO production, e.g. E. coli, may comprise an endogenous β-galactosidase gene or an exogenous β-galactosidase gene, e.g. E. coli comprises an endogenous lacZ gene (e.g., GenBank Accession Number V00296 (GI:41901)). For the purposes of the invention, an HMO-producing bacterial cell is genetically manipulated to either comprise any β-galactosidase gene or to comprise the gene that is inactivated. The gene may be inactivated by a complete or partial deletion of the corresponding nucleic acid sequence from the bacterial genome, or the gene sequence is mutated in the way that it is transcribed et al, or, if transcribed, the transcript is not translated or if translated to a protein (i.e. β-galactosidase), the protein does not have the corresponding enzymatic activity. In this way the HMO-producing bacterium accumulates an increased intracellular lactose pool which is beneficial for the production of HMOs.

A functional lactose permease gene is preferably present in the HMO-producing bacterium of the invention. The lactose permease gene is an endogenous lactose permease gene or an exogenous lactose permease gene. For example, the lactose permease gene comprises an E. coli lacY gene (e.g., GenBank Accession Number V00295 (GI:4:1897)). Many bacteria possess the inherent ability to transport lactose from the growth medium into the cell, by utilizing a transport protein that is either a homolog of the E. coli lactose permease (e.g., as found in Bacillus licheniformis), or a transporter that is a member of the ubiquitous PTS sugar transport family (e.g., as found in Lactobacillus casei and Lactobacillus rhamnosus). For bacteria lacking an inherent ability to transport extracellular lactose into the cell cytoplasm, this ability is conferred by an exogenous lactose transporter gene (e.g., E. coli lacY) provided on recombining DNA constructs, and supplied either on a plasmid expression vector or as exogenous genes integrated into the host chromosome.

To produce a fucosylated oligosaccharide by biosynthesis, the bacterium preferably comprises a mutation in an endogenous colanic acid (a fucose-containing exopolysaccharide) synthesis gene. By "colanic acid synthesis gene" is meant a gene involved in a sequence of reactions, usually controlled and catalyzed by enzymes that result in the synthesis of colanic acid. Exemplary colanic acid synthesis genes include an rcsA gene (e.g., GenBank Accession Number M58003 (GI:1103316)), an rcsB gene, (e.g., GenBank Accession Number E04821 (GI:2173017)), a wcaJ gene, (e.g., GenBank Accession Number (amino acid) BAA15900 (GI:1736749), a wzxC gene, (e.g., GenBank Accession Number (amino acid) BAA15899 (GI:1736748)), a wcaD gene, (e.g., GenBank Accession Number (amino acid)

BAE76573 (GI:85675202)), a wza gene, (e.g., GenBank Accession Number (amino acid) BAE76576 (GI: 85675205)), a wzb gene, and (e.g., GenBank Accession Number (amino acid) BAE76575 (GI:85675204)), and a wzc gene (e.g., GenBank Accession Number (amino acid) BAA15913 (GI:1736763)).

This is achieved through a number of genetic modifications of endogenous *E. coli* genes involved either directly in colanic acid precursor biosynthesis, or in overall control of the colanic acid synthetic regulon. Specifically, the ability of the *E. coli* host strain to synthesize colanic acid, an extracellular capsular polysaccharide, is eliminated by the deletion of the wcaJ gene, encoding the UDP-glucose lipid carrier transferase. In a wcaJ null background, GDP-fucose accumulates in the *E. coli* cytoplasm. Over-expression of a positive regulator protein, RcsA, in the colanic acid synthesis pathway results in an increase in intracellular GDP-fucose levels. Over-expression of an additional positive regulator of colanic acid biosynthesis, namely RcsB, is also utilized, either instead of or in addition to the over-expression of RcsA, to increase intracellular GDP-fucose levels. Alternatively, colanic acid biosynthesis is increased following the introduction of a null mutation into the *E. coli* ion gene (e.g., GenBank Accession Number L20572 (GI: 304907), incorporated herein by reference). Lon is an adenosine-5'-triphosphate (ATP)-dependant intracellular protease that is responsible for degrading RcsA, which was mentioned above as a positive transcriptional regulator of colanic acid biosynthesis in *E. coli*. In a ion null background, RcsA is stabilized, RcsA levels increase, the genes responsible for GDP-fucose synthesis in *E. coli* are up-regulated (i.e. over-expressed), and intracellular GDP-fucose concentrations are increased. RcsA and RcsB proteins are contemplated as beneficial for the purposes of the invention and in some embodiment their levels in the host cells are up-regulated with the use of constructs of the invention, where the corresponding genes are operably linked to a glp promoter, preferably PglpF.

Preferably, a fucosylated HMO producing bacterium comprises an exogenous fucosyltransferase gene. For example, the exogenous fucosyltransferase gene encodes α(1,2) fucosyltransferase and/or α(1,3) fucosyltransferase. An exemplary α(1,2) fucosyltransferase gene is the wcfW gene from *Bacteroides fragilis* NCTC 9343. An exemplary α(1,3) fucosyltransferase gene is the *Helicobacter pylori* 26695 *futA* gene, One example of the *Helicobacter pylori futA* gene is presented in GenBank Accession Number HV532291 (GI:365791177). In the context of the invention, enzymes with fucosyltrasferase activity (such as e.g. fucosyltransferases encoded by the latter genes) are referred herein as protein that are essential for the fucosylated HMO production and directly involved in the production of one or more fucosylated HMOs.

A method for producing a fucosylated HMO by biosynthesis according to the invention may comprise the following steps: providing a bacterium that comprises a dysfunctional β-galactodsidase gene, an exogenous fucosyltransferase gene, wherein the exogenous fucosyltransferase gene is part of an expression cassette where the gene is operably linked to a glp promoter, e.g. PglpF, a mutation in a colanic acid gene cluster, and a functional lactose permease gene; culturing the bacterium in the presence of a carbon source, e.g. glycerol, glucose, sucrose, lactose, etc; and retrieving a fucosylated HMO from the bacterium or from a culture supernatant of the bacterium. The HMO producing bacteria used herein are genetically engineered to an increased intracellular lactose pool (as compared to wild type), to comprise an increase level of fucosyltransferase activity and, optionally, to comprise an increased intracellular guanosine diphosphate (GDP)-fucose pool. According to the invention the later bacteria comprise at least one nucleic acid construct that comprises a nucleic acid sequence encoding for an enzyme that is directly or indirectly involved in HMO production, and a glp promoter of the invention, preferably PglpF, which is operably linked to this nucleic acid sequence. The bacterium may also contain a mutation in a colanic acid (a fucose-containing exopolysaccharide) synthesis pathway gene, such as a wcaJ gene, resulting in an enhanced intracellular GDP-fucose pool. The endogenous lacZ gene of the *E. coli* is preferably deleted or functionally inactivated, but in such a way that expression of the downstream lactose permease (lacY) gene remains intact. The organism manipulated as described above maintains the ability to transport lactose from the growth medium and develops an intracellular lactose pool for use as an acceptor sugar in oligosaccharide synthesis. The bacterium may further comprise an exogenous rcsA and/or rcsB gene (e.g., in an ectopic nucleic acid construct such as a plasmid), and the bacterium optionally further comprises a mutation in a lacA gene.

Bacteria possessing fucosultransfease activity may comprise one or both of an exogenous fucosyltransferase gene encoding an α(1,2) fucosyltransferase and an exogenous fucosyltransferase gene encoding an α(1,3) fucosyltransferase. An exemplary α(1,2) fucosyltransferase gene is the wcfW gene from *Bacteroides fragilis* NCTC 9343. Other α(1,2) fucosyltransferase genes that use lactose as an acceptor sugar (e.g., the *Helicobacter pylori* 26695 MC gene or the *E. coli* O128:B12 wbsJ gene) may readily be substituted for *Bacteroides fragilis* wcfW. One example of the *Helicobacter pylori* futC gene is presented in GenBank Accession Number EF452503 (GI:134142866). An exemplary α(1,3) fucosyltransferase gene is the Heficobacterpyiori 26695 futA gene, although other α(1,3) fucosyltransferase genes known in the art may be substituted (e.g., α(1,3) fucosyltransferase genes from *Helicobacter hepaticaus* Hh0072, *Helicobacter bilis, Campylobacter jejuni*, or from *Bacteroides species*). Some examples of α(1,3) fucosyltransferases and other enzymes that are involved in the production of different fucosylated HMOs are shown in Table 4 below.

TABLE 4

| Gene | Species origin | Accession number | Enzyme | HMO example |
|---|---|---|---|---|
| MAMA_R764 | *Acanthamoeba polyphaga moumouvirus* | AGC02224.1 | α-1,3-fucosyl-transferase | 2'FL, 3'FL, DFL, LNFP-I, LNFP-III, LNFP-V, LNFP-VI, LNDFH-II, F-pLNH I |
| Mg791 | *Megavirus chiliensis* | AEQ33441.1 | α-1,3-fucosyl-transferase | 2'FL, 3'FL, DFL, LNFP-I, LNFP-III, LNFP-V, LNFP-VI, LNDFH-II, F-pLNH I |

TABLE 4-continued

| Gene | Species origin | Accession number | Enzyme | HMO example |
|---|---|---|---|---|
| Moumou_00703 | *Acanthamoeba polyphaga moumouvirus M10A* | AGC02224.1 | α-1,3-fucosyl-transferase | 2'FL, 3'FL, DFL, LNFP-I, LNFP-III, LNFP-V, LNFP-VI, LNDFH-II, F-pLNH I |
| futA | *Helicobacter pylori ATCC 26695* | NP_207177.1 | α-1,3-fucosyl-transferase | 2'FL, 3'FL, DFL, LNFP-I, LNFP-III, LNFP-V, LNFP-VI, LNDFH-II, F-pLNH I |
| fucT | *Helicobacter pylori NCTC 11639* (truncated) | AAB81031.1 | α-1,3-fucosyl-transferase | 2'FL, 3'FL, DFL, LNFP-I, LNFP-III, LNFP-V, LNFP-VI, LNDFH-II, F-pLNH I |
| fucTIII | *Helicobacter pylori ATCC 43504* | AY450598.1 | α-1,4-fucosyl-transferase | LNDFH-I, LNDFH-II |
| fucTa | *Helicobacter pylori UA948* | AF194963.2 | α-1,3/4-fucosyl-transferase | LNFP-II, LNDFH-I, LNDFH-II |

The bacterium may comprise the expression cassette of the invention providing expression or overexpression of one or more of the above fucosyltransferases and, correspondingly, a higher production of one or more fucosylated HMO, e.g., 2'-FL, 3FL, DFL, LNFP-I, -II, -III, -V, VI, LNDFH-I, -II or -III.

The invention in further embodiments relates to HMO-producing host cells that comprise one or more nucleic acid constructs comprising one, two, three or more of any of the genes described herein (i.e. the genes encoding essential or beneficial proteins for the HMO production), wherein preferably at least one of the constructs is comprising Pglp promoter operably linked to at least one of the genes, wherein at least one of the constructs is genomically integrated, wherein preferably, the at least one the genome integrated constructs comprises Pglp promoter operably linked to at least one of the genes encoding a protein that is essential for the synthesis of an HMO and said construct is present in the genome at a low copy number. In some embodiments, the host cells of invention may produce fucosylated HMOs, in other embodiments, the cells may produce sialylated HMOs, in other embodiments, the cells may produce non-fucosylated neutral HMOs.

To produce sialylated HMOs described herein general principles and methods previously described in the art may be used (see e.g. Drouillard S et al, (2010) Carbohydrate Research 345:1394-1399, or Fierfort N & Samain E (2008) J Biotechnol 134:261-265).

In general, a engineered bacterial cell that is enabled to produce a sialylated human milk oligosaccharide, e.g. 6'-SL (6'-sialyllactose), comprises an exogenous sialyl-transferase gene encoding for an α(2,6)sialyl-transferase. The bacterial cell could be *E. coli*. The exogenous sialyl-transferase gene utilized for 6'-SL production may be obtained from any available sources, e.g., those described from a number of organisms of the genus *Photobacterium*. Yet another sialylated HMO, e.g. is 3'-SL (3'-sialyllactose), may be produced by an engineered bacteria comprising an exogenous nucleic acid molecule encoding for an α(2,3) sialyltransferase. The exogenous sialyltransferase gene utilized for 3'-SL production may be obtained from any available source, e.g., those described from *Neisseria meningitidis* and *Neisseria gonorrhoeae*. Some examples of suitable sialyltransferases are listed in Table 5 below.

TABLE 5

| Gene | Species origin | Assetion number | Enzyme | HMO |
|---|---|---|---|---|
| Pd2,6ST | *Photobacterium damselae JT0160* | BAA25316.1 | α-2,6-sialyltransferase | 6'SL |
| PspST6 | *Photobacterium sp. JT-ISH-224* | BAF92026.1 | α-2,6-sialyltransferase | 6'SL |
| PiST6_145 | *Photobacterium leiognathi JT-SHIZ-145* | BAF91416.1 | α-2,6-sialyltransferase | 6'SL |
| PiST6_119 | *Photobacterium leiognathi JT-SHIZ-119* | BAI49484.1 | α-2,6-sialyltransferase | 6'SL |
| NST | *Neisseria meningitidis MC58* | AAC44541.1 | α-2,3-sialyltransf erase | 3'SL |
| NGO_1081 | *Neisseria gonorrhoeae* (strain ATCC 700825/FA 1090) | YP_208160.1 | α-2,3-sialyltransferase | 3'SL |

Preferably, the engendered bacterium contains a deficient sialic acid catabolic pathway. By "sialic acid catabolic pathway" is meant a sequence of reactions, usually controlled and catalyzed by enzymes, which results in the degradation of sialic acid. An exemplary sialic acid catabolic pathway described herein is the *E. coli* pathway. In this pathway, sialic acid (Neu5Ac; N-acetylneuraminic acid) is degraded by the enzymes NanA (N-acetylneuraminic acid lyase) and NanK (N-acetylmannosamine kinase) and NanE (N-acetylmannosamine-6-phosphate epimerase), all encoded from the nanATEK-yhcH operon, and repressed by NanR (http://ecocyc.org/ECOLI). A deficient sialic acid catabolic pathway is rendered in the *E. coli* host by introducing a mutation in the endogenous nanA (N-acetylneuraminate lyase) (e.g., GenBank Accession Number D00067.1(GL216588)) and/or nanK (N-acetylmannosamine kinase) genes (e.g., GenBank Accession Number (amino acid) BAE77265.1 (GL85676015)), and/or nanE (N-acetylmannosamine-6-phosphate epimerase, GI: 947745, incorporated herein by reference). Optionally, the nanT (N-acetylneuraminate transporter) gene is also inactivated or mutated. Other intermediates of sialic acid metabolism include: (ManNAc-6-P) N-acetylmannosamine-6-phosphate; (GlcNAc-6-P) N-acetylglucosamine-6-phosphate; (GlcN-6-P) Glucosamine-6-phosphate, and (Fruc-6-P) Fructose-6-phosphate. In some preferred embodiments, nanA is mutated. In other preferred embodiments, nanA and nanK are mutated, while nanE remains functional. In another preferred embodiment, nanA and nanE are mutated, while nanK has not been mutated, inactivated or deleted. A mutation is one or more changes in the nucleic acid sequence coding the gene product of nanA, nanK, nanE, and/or nanT. For example, the mutation may be 1, 2, up to 5, up to 10, up to 25, up to 50 or up to 100 changes in the nucleic acid sequence. For example, the nanA, nanK, nanE, and/or nanT genes are mutated by a null mutation. Null mutations as described herein encompass amino acid substitutions, additions, deletions, or insertions, which either cause a loss of function of the enzyme (i.e. reduced or no activity) or loss of the enzyme (i.e. no gene product). By "deleted" is meant that the coding region is removed completely or in part such that no (functional) gene product is produced. By inactivated is meant that the coding sequence has been altered such that the resulting gene product is functionally inactive or encodes for a gene product with less than 100%, e.g. 90%, 80%, 70%, 60%, 50%, 40%, 30% or 20% of the activity of the native, naturally occurring, endogenous gene product. A "not mutated" gene or protein does not differ from a native, naturally-occurring, or endogenous coding sequence by 1, 2, up to 5, up to 10, up to 20, up to 50, up to 100, up to 200 or up to 500 or more codons, or to the corresponding encoded amino acid sequence.

Furthermore, the bacterium (e.g., *E. coli*) also comprises a sialic acid synthetic capability. For example, the bacterium comprises a sialic acid synthetic capability through provision of an exogenous UDP-GlcNAc 2-epimerase (e.g., neuC of *Campylobacter jejuni* (GenBank AAK91727.1; GL15193223) or equivalent (e.g. neuC of *E.coli* S88 (GenBank YP_002392936.1; GI: 218560023), a Neu5Ac synthase (e.g., neuB of *C. jejuni* (GenBank AAK91726.1; GI:15193222) or equivalent, (e.g. *Flavobacterium limnosediminis* sialic acid synthase, GenBank GL559220424), and/or a CMP-Neu5Ac synthetase (e.g., neuA of *C. jejuni* (GenBank AAK91728.1; GI:15193224) or equivalent, (e.g. *Vibrio brasiliensis* CMP-sialic acid synthase, GenBank GI: 493937153).

Bacteria producing sialylated HMO's comprise one or more exogeneous sialyltransferases, which are encoded by the coding DNA of an expression cassette of the invention that is present in the host cells either as plasmid-borne or genome-integrated. Preferably, at least one of the one or more sialyltransferase-coding DNA sequences is operably linked to a glp promoter described herein, preferably PglpF. Non-limited examples of useful sialyltranferases are listed in Table 5.

The bacterium comprising the capability of sialic acid synthesis, may advantageously be engineered to have an increased production of UDP-GlcNAc. An exemplary means to achieve this is by over-expression of a positive endogenous regulator of UDP-GlcNAc synthesis, for example, simultaneous overexpression of the nagC and glmS genes of *E. coli*. This nagC and glmS over-expression is preferably achieved by operably linking the genes to a glp promoter of the invention and expressing the cassette as genome integrated, or, alternatively, it may be achieved by providing additional copies of the nagC and glmS genes linked to a glp or another promoter on a plasmid vector.

Production of neutral N-acetylglucoseamine-containing HMOs in engineered bacteria is also known in the art (see e.g. Gebus C et al (2012) Carbohydrate Research 363 83-90).

For the production of N-acetylglucosamine-containing HMOs, such as Lacto-N-triose 2 (LNT2), Lacto-N-tetraose (LNT), Lacto-N-neotetraose (LNnT), Lacto-N-fucopentaose I (LNFP-I), Lacto-N-fucopentaose II (LNFP-II), Lacto-N-fucopentaose III (LNFP-III), Lacto-N-fucopentaose V (LNFP-V), Lacto-N-difucohexaose 1 (LDFH-I), Lacto-N-difucohexaose II (LDFH-II), and Lacto-N-neodifucohexaose II (LNDFH-III), the bacterium comprises a functional lacY and a dysfunctional lacZ gene, as described above, and it is engineered to comprise an exogenous UDP-GlcNAc:Galα/β-R β 3-N-acetylglucosaminyltransferase gene, or a functional variant or fragment thereof. This exogenous UDP-GlcNAc:Galα/β-R β 3-N-acetylglucosaminyltransferase gene may be obtained from any one of a number of sources, e.g., the IgtA gene described from *N. meningitides* (Genbank protein Accession AAF42258.1) or *N. gonorrhoeae* (Genbank protein Accession ACF31229.1). Optionally, an additional exogenous glycosyltransferase gene may be co-expressed in the bacterium comprising an exogenous UDP-GlcNAc:Galα/β-R β 3-N-acetylglucosaminyltransferase. For example, a β-1,4-galactosyltransferase gene is co-expressed with the UDP-GlcNAc:Galα/β-R β 3-N-acetylglucosaminyltransferase gene. This exogenous β-1,4-galactosyltransferase gene can be obtained from any one of a number of sources, e.g., the one described from *N. meningitidis*, the IgtB gene (Genbank protein Accession AAF42257.1), or from *H. pylori*, the HP0826/galT gene (Genbank protein Accession NP_207619.1). Optionally, the additional exogenous glycosyltransferase gene co-expressed in the bacterium comprising an exogenous UDP-GlcNAc:Galα/β-R β 3-N-acetylglucosaminyltransferase gene is a P-l,3-galactosyltransferase gene, e.g., that described from *E. coli* 055:H7, the wbgO gene (Genbank protein Accession YP_003500090.1), or from *H. pylori*, the jhp0563 gene (Genbank protein Accession AEZ55696.1), or from *Streptococcus agalactiae* type lb OI2 the cpslBJ gene Genbank protein Accession AB050723). Functional variants and fragments of any of the enzymes described above are also encompassed by the present invention.

Preferably, at least one gene encoding for the enzyme as any of the above, i.e. both/either an N-acetylglucosaminyltransferase gene and/or a galactosyltransferase gene, are operably linked to a Pglp of the invention and expressed from the corresponding genome-integrated cassette. In one embodiment, the gene that is genome integrated is a gene encoding for a galactosyltransferase, e.g. HP0826 gene encoding for the GaIT enzyme from *H. pylori* (Genbank protein Accession NP_207619.1); in another embodiment, the gene that is genome integrated is a gene encoding a β-1,3-N-acetylglucosaminyltransferase, e.g. IgtA gene from *N. meningitides* (Genbank protein Accession AAF42258.1). In these embodiments, the second gene, i.e. a gene β-1,3-N-acetylglucosaminyltransferase or galactosyltransferase, correspondingly, may either be expressed from a genome-integrated or plasmid borne cassette. The second gene may optionally be expressed either under the control of a glp promoter or under the control of any other promoter suitable for the expression system, e.g. Plac.

Advantageously, a bacterium producing N-acetylglucosamine-containing HMOs may be engineered to have an increased intracellular UDP-GlcNAc pool. An exemplary means to achieve this trait is by the over-expression of a positive endogenous regulator of the UDP-GlcNAc synthesis, e.g. the simultaneous overexpression of the nagC and glmS genes of *E. coli*. This nagC and glmS over-expression is preferably achieved by operably linking the genes to a glp promoter of the invention and integrating the cassette in the host genome, or, alternatively, it may be achieved by providing additional copies of the nagC and glmS genes linked to a glp or another promoter on a plasmid vector.

To produce HMOs, the HMO-producing bacteria as described herein are cultivated according to the procedures known in the art in the presence of a suitable carbon source, e.g. glucose, glycerol, lactose, etc., and the produced HMO is harvested from the cultivation media and the microbial biomass formed during the cultivation process. Thereafter, the HMOs are purified according to the procedures known in the art, e.g. such as described in WO2015188834, WO2017182965 or WO2017152918, and the purified HMOs are used as nutraceuticals, pharmaceuticals, or for any other purpose, e.g. for research.

Other features and advantages of the invention will be apparent from the description of working examples below, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and therefore not limiting the scope of the invention.

EXAMPLES

Materials and Methods

Unless otherwise noted, standard techniques, vectors, control sequence elements, and other expression system elements known in the field of molecular biology are used for nucleic acid manipulation, transformation, and expression. Such standard techniques, vectors, and elements can be found, for example, in: Ausubel et al. (eds.), *Current Protocols in Molecular Biology* (1995) (John Wiley & Sons); Sambrook, Fritsch, & Maniatis (eds.), *Molecular Cloning* (1989) (Cold Spring Harbor Laboratory Press, NY); Berger & Kimmel, *Methods in Enzymology* 152: Guide to Molecular Cloning Techniques (1987) (Academic Press); Bukhari et al. (eds.), *DNA Insertion Elements, Plasmids and Episomes* (1977) (Cold Spring Harbor Laboratory Press, NY); Miller, J. H. Experiments in molecular genetics (1972.) (Cold spring Harbor Laboratory Press, NY).

Strains and Plasmids

The bacterial strain used, MDO, was constructed from *Escherichia coli* K12 DH1. The *E. coli* K12 DH1 genotype is: $F^-$, $\lambda^-$, gyrA96, recA1, relA1, endA1, thi-1, hsdR17, supE44. In addition to the *E. coli* K12 DH1 genotype MDO has the following modifications: lacZ: deletion of 1.5 kbp, lacA: deletion of 0.5 kbp, nanKETA: deletion of 3.3 kbp, melA: deletion of 0.9 kbp, wcaJ: deletion of 0.5 kbp, mdoH: deletion of 0.5 kbp, and insertion of Plac promoter upstream of the gmd gene.

Strains utilized in the present Examples are described in Table 6. Donor and helper plasmids used for the construction of these strains are enlisted in Table 7 along with multi-copy plasmids introduced in some of the engineered strains.

TABLE 6

| Strain IDs | Genomic Description | Plasmid Description |
|---|---|---|
| Background Strains | | |
| DH1 | $F^- \lambda^-$ endA1 recA1 relAl gyrA96 thi-1 glnV44 hsdR17($r_K^- m_K^-$) | |
| MDO | *E coli* DH1 ΔlacZ , ΔlacA, ΔnanKETA, ΔmelA, ΔwcaJ, ΔmdoH | |
| Strains expressing reporter genes | | |
| MAP808 | MDO galK::PglpF-lacZ-T1 | — |
| MAP1010-9 | MDO galK::PglpF400-9-lacZ-T1 | — |
| MAP1010-11 | MDO galK::PglpF400-11-lacZ-T1 | — |
| MAP1010-13 | MDO galK::PglpF400-13-lacZ-T1 | — |
| MAP1010-17 | MDO galK::PglpF400-17-lacZ-T1 | — |
| MAP1010-19 | MDO galK::PglpF400-19-lacZ-T1 | — |
| MAP1010-20 | MDO galK::PglpF400-20-lacZ-T1 | — |
| MAP1025 | MDO galK::PglpA-lacZ-T1 | — |
| MAP1026 | MDO galK::PglpD-lacZ-T1 | — |
| MAP1027 | MDO galK::PglpT-lacZ-T1 | — |
| MAP1086 | MDO galK::Δ175PglpF-lacZ-T1 | — |
| MAP1176 | MDO galK::PglpF_SD1-lacZ-T1 | — |
| MAP1178 | MDO galK::PglpF_SD3-lacZ-T1 | — |
| MAP1179 | MDO galK::PglpF_SD4-lacZ-T1 | — |
| MAP1180 | MDO galK::PglpF_SD5-lacZ-T1 | — |
| MAP1181 | MDO galK::PglpF_SD6-lacZ-T1 | — |
| MAP1182 | MDO galK::PglpF_SD7-lacZ-T1 | — |
| MAP1183 | MDO galK::PglpF_SD8-lacZ-T1 | — |
| MAP1184 | MDO galK::PglpF_SD9-lacZ-T1 | — |
| MAP1185 | MDO galK::PglpF_SD10-lacZ-T1 | — |
| MAP1206 | MDO galK::PglpF_SD2-lacZ-T1 | — |
| MAP1209 | MDO galK::Δ190PglpF-lacZ-T1 | — |
| MAP1210 | MDO galK:Δ25PglpF-lacZ-T1 | — |
| MAP1211 | MDO galK::Δ150PglpF-lacZ-T1 | — |
| MAP1356 | MDO galK::PglpF-lacZ-T1-galK glpR::kanR | — |
| MAP1365 | MDO galK::PglpA_org-lacZ-T1-galK | — |
| MAP1366 | MDO galK::PglpD_org-lacZ-T1-galK | — |
| MAP1367 | MDO galK::PglpT_org-lacZ-T1-galK | — |
| MAP1368 | MDO galK::PglpF_org-lacZ-T1-galK | — |
| MAP1370 | MDO galK::Plac_org-lacZ-T1-galK | — |

TABLE 6-continued

| Strain IDs | Genomic Description | Plasmid Description |
|---|---|---|
| Strains expressing recombinant genes | | |
| MAP219 | MDO Plac-Pd2 | — |
| MAP700 | MDO Plac-nst | — |
| MAP710 | MDO PglpF-nst | — |
| MAP986 | MDO PglpF-Pd2 | — |
| MDO1 | MDO | pBBR3-Plac-IgtA-tet, pBS-Plac-galT-amp |
| MDO15 | MDO | pBBR3-Plac-IgtA-tet, pBS-Plac-galTK-amp |
| MP166 | MDO 3xPlac-IgtA 3xPlac-galT lacI::CP6-galK | — |
| MP245 | MDO 3xPlac-IgtA 2xPlac-galTK ΔlacI | — |
| MP1497 | MDO PglpF-IgtA | pBS-Plac-galT-amp |
| MP1498 | MDO PglpF-IgtA | pBS-Plac-galTK-amp |
| MP1499 | MDO PglpF-galT | pBBR3-Plac-IgtA-tet |
| MP1655 | MDO 2xPglpF-galTK | pBBR3-Plac-IgtA-tet |
| MP1825 | MDO PglpF-galT PglpF-IgtA lack:CP6-galK | — |
| MP1920 | MDO PglpF-galTK PglpF-IgtA lack:CP6-galK | — |
| MP2239 | MDO PglpF-galTK PglpF-IgtA PglpF-futC ΔlacI | — |
| MP2374 | MDO PglpF-galTK PglpF-IgtA PglpF-futC PglpF-CA ΔlacI | — |
| MP2622 | MDO Plac-IgtA Plac-galT | — |
| MAP265 | MDO Plac-Pd2 nadC::galK | pBS-Plac-neuBCA-nadC |
| MAP425 | MDO 2xPlac-nst Plac-neuBCA A5OlacI | pBS-Plac-neuBCA-nadC |
| MAP1200 | MDO PglpF-neuA PglpF-neuB PglpF-neuC PglpF-Pd2 | — |
| MAP1214 | MDO PglpF-neuA PglpF-neuB PglpF-neuC PglpF-nst | — |
| FT18 | MDO | pBP-Plac-futC-kan pBBR3-Plac-gmd-fcl-cpsB-cpsG |
| MAP965 | MDO PglpF-gmd-fcl-gmm-wcaI-cpsB-cpsG PglpF-futC_op | — |

TABLE 7

| Plasmid ID | Description |
|---|---|
| pACBSR | Para-I-SceI-A Red, p15A or cam* |
| pUC57 | pMB1, bla |
| pUC57::gal | pUC57::galTK'/T-1-galKM' |
| pMAP99 | pUC57-galTK'-Plac-Pd2_op-T1-galKM' |
| pMAP205 | pUC57::galTK'-PglpF-lacZ-T1-galKM' |
| pMAP216 | pUC57-galTK'-Plac-A29nst_op-T1-galKM' |
| pMAP228 | pUC57-galTK'-PglpF-A29nst_op-T1-galKM' |
| pMAP391 | pUC57-galTK'-PglpF-Pd2-T1-galKM' |
| pMAP431 | pUC57-galTK'-PgIpA-lacZ-T1-galKM' |
| pMAP432 | pUC57-galTK'-PgIpD-lacZ-T1-galKM' |
| pMAP433 | pUC57-galTK'-PgIpT-lacZ-T1-galKM' |
| pMAP457 | pUC57-galTK'-D25PglpF-lacZ-T1-galKM' |
| pMAP462 | pUC57-galTK'-D150PglpF-lacZ-T1-galKM' |
| pMAP463 | pUC57-galTK'-D175PglpF-lacZ-T1-galKM' |
| pMAP486 | pUC57-galTK'-PglpF_SD1-lacZ-T1-galKM' |
| pMAP487 | pUC57-galTK'-PglpF_SD2-lacZ-T1-galKM' |
| pMAP488 | pUC57-galTK'-PglpF_SD3-lacZ-T1-galKM' |
| pMAP489 | pUC57-galTK'-PglpF_SD4-lacZ-T1-galKM' |
| pMAP490 | pUC57-galTK'-PglpF_SD5-lacZ-T1-galKM' |
| pMAP491 | pUC57-galTK'-PglpF_SD6-lacZ-T1-galKM' |
| pMAP492 | pUC57-galTK'-PglpF_SD7-lacZ-T1-galKM' |
| pMAP493 | pUC57-galTK'-PglpF_SD8-lacZ-T1-galKM' |
| pMAP494 | pUC57-galTK'-PglpF_SD9-lacZ-T1-galKM' |
| pMAP495 | pUC57-galTK'-PglpF_SD10-lacZ-T1-galKM' |
| pMAP537 | pUC57-galTK'-D190PglpF-lacZ-T1-galKM' |
| pMAP689 | pUC57-galTK'-PgIpA_org-lacZ-T1-galKM' |
| pMAP690 | pUC57-galTK'-PgIpD_org-lacZ-T1-galKM' |
| pMAP691 | pUC57-galTK'-PgIpT_org-lacZ-T1-galKM' |
| pMAP693 | pUC57-galTK'-PglpF_org-lacZ-T1-galKM' |
| pMAP695 | pUC57-galTK'-Plac_org-lacZ-T1-galKM' |
| MP55 | pBBR3-Plac-IgtA-tet, |
| MP46 | pBS-Plac-galT-amp |
| MP139 | pBS-Plac-galTK-amp |
| pMAP101 | pBS-Plac-neuBCA-nadC |
| MP415 | pBP-Plac-futC-kan |
| MP416 | pBBR3-Plac-gmd-fcl-cpsB-cpsG |

Media

The Luria Broth (LB) medium was made using LB Broth Powder, Millers (Fisher Scientific) and LB agar plates were made using LB Agar Powder, Millers (Fisher Scientific). Screening of strains on LB plates containing 5-Bromo-4-chloro-3-indolyl-β-D-galactopyranoside (X-gal) was done using an X-gal concentration of 40 μg/ml. When appropriated ampicillin (100 μg/ml) and/or chloramphenicol (20 μg/ml) was added.

Basal Minimal medium had the following composition: NaOH (1 g/L), KOH (2.5 g/L), $KH_2PO_4$ (7 g/L), $NH_4H_2PO_4$ (7 g/L), Citric acid (0.5 g/l), Trace mineral solution (5 ml/L). The trace mineral stock solution contained: $ZnSO_4*7H_2O$ 0.82 g/L, Citric acid 20 g/L, $MnSO_4$ $H_2O$ 0.98 g/L, $FeSO_4$ $7H_2O$ 3.925 g/L, $CuSO_4$ $5H_2O$ 0.2 g/L. The pH of the Basal Minimal Medium was adjusted to 7.0 with 5 N NaOH and autoclaved. Before inoculation the Basal Minimal medium was supplied with 1 mM $MgSO_4$, 4 μg/ml thiamin, 0.5% of a given carbon source (glucose, glycerol, sorbitol, xylose, lactose, maltose (Carbosynth)), and when appropriated Iso-propyl-β-D-Thiogalactoside (IPTG) (0.2 mM), ampicillin (100 μg/ml) and/or chloramphenicol (20 μg/ml) was added. Thiamin, antibiotics, and IPTG were sterilized by filtration. All percentage concentrations for glycerol are expressed as v/v and those for glucose, sorbitol, xylose, lactose, and maltose as w/v.

M9 plates containing 2-deoxy-galactose had the following composition: 15 g/L agar (Fisher Scientific), 2.26 g/L 5× M9 Minimal Salt (Sigma-Aldrich), 2 mM MgSO4, 4 μg/ml thiamine, 0.2% glycerol, and 0.2% 2-deoxy-D-galactose (Carbosynth).

MacConkey indicator plates containing galactose had the following composition: 40 g/L MacConkey agar Base (BD Difco™). After autoclaving and cooling to 50° C., D-galactose (Carbosynth) was added to a final concentration of 1%.

Cultivation

Unless otherwise noted, *E. coli* strains were propagated in Luria-Bertani (LB) medium containing 0.2% glucose at 37° C. with agitation.

Cultures harvested for β-galactosidase assays were made in the following way: A single colony from an LB-plate was pre-cultured in 1 ml Basal Minimum media containing glucose (0.5%) in a 10 ml 24 Deep well plate (Axygen). The plate was sealed before culturing with a Hydrophobic Gas Permeable Adhesive Seal (Axygen) and incubated for 24 hours at 34° C. with shaking at 700 rpm in an orbital shaker (Edmund Bühler GmbH). Cell density of the culture was monitored at 600 nm using an S-20 spectrophotometer (Boeco, Germany). 20 µl of the overnight culture was used for inoculation in 2 ml LB or Basal Minimum media containing glucose or another carbon source (0.5%) in a 24 Deep well plate. Antibiotics and/or IPTG were added if appropriated. The Deep well plates were covered with sealing foil and incubated for 24 hours at 28° C. with orbital shaking at 700 rpm. After incubation, OD600 was measured and 0.5 ml cell culture was harvested by centrifugation for preforming β-galactosidase assay.

Chemical Competent Cells and Transformations

*E. coli* was inoculated from LB plates in 5 ml LB containing 0.2% glucose at 37° C. with shaking until OD600 ~0.4. 2 ml culture was harvested by centrifugation for 25 seconds at 13.000 g. The supernatant was removed, and the cell pellet resuspended in 600 ul cold TB solutions (10 mM PIPES, 15 mM $CaCl_2$, 250 mM KCl). The cells were incubated on ice for 20 minutes followed by pelleting for 15 seconds at 13.000 g. The supernatant was removed, and the cell pellet resuspended in 100 µl cold TB solution. Transformation of plasmids were done using 100 µl competent cells and 1-10 ng plasmid DNA. Cells and DNA were incubated on ice for 20 minutes before heat shocking at 42° C. for 45 seconds. After 2 min incubation on ice 400 µl SOC (20 g/L tryptone, 5 g/L Yeast extract, 0.5 g/L NaCl, 0.186 g/L KCl, 10 mM $MgCl_2$, 10 mM $MgSO_4$ and 20 mM glucose) was added and the cell culture was incubated at 37° C. with shaking for 1 hour before plating on selective plates. Plasmid ligations were transformed into TOP10 chemical competent cells at conditions recommended by the supplier (ThermoFisher Scientific).

DNA techniques

Plasmid DNA from *E. coli* was isolated using the QIAprep Spin Miniprep kit (Qiagen). Chromosomal DNA from *E. coli* was isolated using the QIAmp DNA Mini Kit (Qiagen). PCR products were purified using the QIAquick PCR Purification Kit (Qiagen). DreamTaq PCR Master Mix (Thermofisher), Phusion U hot start PCR master mix (Thermofisher), USER Enzym (New England Biolab) were used as recommended by the supplier. Primers were supplied by Eurofins Genomics, Germany. PCR fragments and plasmids were sequenced by Eurofins Genomics.

Colony PCR was done using DreamTaq PCR Master Mix, at conditions recommended by the supplier (Thermofisher) in a T100™ Thermal Cycler (Bio-Rad). For instance, during the construction of strains expressing a reporter or recombining gene from the galK locus, primers O48 (5'-CCCAGCGAGACCTGACCGCAGAAC-3') (SEQ ID NO: 58) and O49 (5'-CCCCAGTCCATCAGCGTGACTACC-3') (SEQ ID NO: 59) were used in a colony PCR reaction aiming to confirm the validity of the intended modification.

TABLE 8

The primers used to construct the backbones used for the preparation of donor plasmids.

| Name | Oligonucleotide Sequence 5'-3' | Description | SEQ ID NO |
|---|---|---|---|
| O40 | ATTAACCCUCCAGGCATCAAA TAAAACGAAAGGC | Backbone.for | 100 |
| O79 | ATTTGCGCAUCACCAATCAAA TTCACGCGGCC | Backbone.rev | 101 |
| O261 | ATGCGCAAAUGCGGCACGCCT TGCAGATTACG | PglpF.for | 102 |
| O262 | AGCTGTTCCTCCTTGGTTAA TGTTTGTTGTATGCG | PglpF.rev | 103 |
| O68 | ATGCGCAAAUTGTGAGTTAGC TCACTCATTAG | Plac.for | 84 |
| O113 | AGCTGTTUCCTCCTTAGGTAC CCAGCTTTTGTTCCC | Plac.rev | 117 |

TABLE 9

The heterologous genes included in the expression cassettes comprising a promoter sequence and the artificial DNA sequence (i) (SEQ ID NO: 70) to enable microbial production of HMOs

| Gene | Origin of Genes | Accession Number | Function |
|---|---|---|---|
| futC | Helicobacter pylori 26695 | EF452503 | α-1,2-fucosyl-transferase |
| lgtA | Neisseria meningitidis 053442 | CP000381 | β-1,3-N-acetylglucosaminyftransferase |
| galT | Helicobacter pylon 26695 | AE000511 | β-1,4-galactosyltransferase |
| galTK | Helicobacter pylori 43504 | homologous to BD182026 | β-1,3-galactosyltransferase |
| neuA | Campylobacter jejuni ATCC43438 | AF400048 | CMP-Neu5A synthetase |
| neuB | Campylobacter jejuni ATCC43438 | AF400048 | Sialic acid synthetase |
| neuC | Campylobacter jejuni ATCC43438 | AF400048 | GlcNAc-6-phosphate 2-epeimerase |
| nst | Neisseria meningitides L3 MC58 | U60660 | α-2,3-sialyltransferase |
| Pd2 | Photobacterim damsela JT0160 | BAA25316.1 | α-2,6-sialyltransferase |

TABLE 10

The primers that were used to amplify the heterologous genes of interest and make the resulting PCR products compatible with plasmid backbones to enable the construction of donor

| Oligo ID | Oligo sequence | Description | SEQ ID NO |
|---|---|---|---|
| MP452 | AAACAGCUAUGAUCUCUGUCUAC ATCATCAGTCTG | galTK_opt for | 105 |
| MP453 | AGGGUUAAUUGCGCGUUAGACUU CTTTCGGGGTTTTCA | galTK_opt rev | 106 |
| O123 | AAACAGCUAUGGCGUUCAAAGUG GTCCAAATC | futC_opt for | 107 |
| O124 | AGGGUUAAUUGCGCGUUAGCCCA GCGCGTTATATTTCTG | futC_opt rev | 108 |
| O142 | AAACAGCUAUGCAACCGCUGGUC TCCGTGC | lgtA_opt for | 109 |
| O143 | AGGGUUAAUUGCGCGUUAACGGU TTTTCAGCAGGCGG | lgtA_opt rev | 110 |
| O342 | AAACAGCUAUGUCAAAAGUCGCU CTCATCACCGG | CA for | 111 |
| O126 | AGGGUUAAUUGCGCGUUACUCGU TCAGCAACGTCAGC | CA rev | 112 |
| O144 | AAACAGCUAUGCGUGUCUUCGCC ATTTCT | galT_opt for | 113 |
| O145 | AGGGUUAAUUGCGCGUUAGACGA ATTGCCAGTATTTCAGG | galT_opt rev | 114 |
| O95 | AAACAGCUAUGGAACGUAACGCC GTGAGCCTGC | nst_opt for | 115 |
| O93 | AGGGUUAAUUGCGGCUUAGUTTTT TATCGTCAAAGGTCAG | nst_opt rev | 116 |
| O26 | AAACAGCUAUGUGCAAUAGCGAU AACACC | Pd2_opt for | 98 |
| O27 | AGGGUUAAUUGCGCGUUAGGCC CAGAACAGAACATC | Pd2_opt rev | 99 |

Construction of Plasmids

A plasmid containing two I-SceI endonuclease sites, separated by two DNA fragments of the gal operon (required for homologous recombination in galK), and a T1 transcriptional terminator sequence (pUC57::gal) was synthesized (GeneScript). The DNA sequences used for homologous recombination in the gal operon covered base pairs 3.628.621-3.628.720 and 3.627.572-3.627.671 in sequence Escherichia coli K12 MG155 complete genome GenBank: ID: CP014225.1. Insertion by homologous recombination would result in a deletion of 949 base pairs of galK and a galK-phenotype.

Standard techniques well-known in the field of molecular biology were used for designing of primers and amplification of specific DNA sequences of the Escherichia coli K-12 DH1 chromosomal DNA. Such standard techniques, vectors, and elements can be found, for example, in: Ausubel et al. (eds.), Current Protocols in Molecular Biology (1995) (John Wiley & Sons); Sambrook, Fritsch, & Maniatis (eds.), Molecular Cloning (1989) (Cold Spring Harbor Laboratory Press, NY); Berger & Kimmel, Methods in Enzymology 152: Guide to Molecular Cloning Techniques (1987) (Academic Press); Bukhari et al. (eds.) A 3.5 kbp plasmid backbone containing pUC57-scel-galTK-T1-galKM-scel, was amplified using primers O40 (SEQ ID:7) and O79 (SEQ ID: 8) (Table 8) and a 3.3 kbp DNA fragment containing lacZ was amplified from chromosomal DNA isolated from E. coli K-12 DH1.

Chromosomal DNA obtained from E. coli DH1 was used to amplify a 300 bp DNA fragment containing the promoter PglpF (SEQ ID NO:57) using oligos O261 (SEQ ID NO:102) and O262 (SEQ ID NO:103), or the promoter Plac (SEQ ID NO:SEQ ID NO:11) using oligos O68 and O113 (SEQ ID NOs:84 and 117) (Table 8). Similar to the 107 bp DNA fragment containing the Plac promoter, Plac_org, a 182 bp DNA fragment containing the PglpA promoter, PglpA_org, a 190 bp DNA fragment containing the PglpD promoter, PglpD_org, a 245 bp DNA fragment containing the PglpT promoter, PglpT_org, and a 300 bp DNA fragment containing the PglpF promoter, PglpF_org, was amplified from the E. coli DH1 genome.

The six-teen nucleotide sequence located upstream of the translational start site of the glp promoters (SEQ ID NOs: 5-8—glpF, A, D and T, correspondingly) (comprising the ribosomal binding site) were altered by PCR in the original (org) promoter fragments. Likewise, the Shine Dalgarno sequence of the PglpF expression element was modified using primers by introducing specific modifications in the oligos used for amplification of the DNA fragments resulting in promoter expression elements PglpF_SD1, PglpF_SD2, PglpF_SD3, PglpF_SD4, PglpF_SD5, PglpF_SD6, PglpF_SD7, PglpF_SD8, PglpF_SD9, and PglpF_SD10 (SEQ ID NOs:13-22, correspondingly).

Truncation of the 5'end of the PglpF expression element was done using specific primers resulting in promoter expression elements Δ15PglpF, Δ140PglpF, Δ165PglpF and Δ198PglpF (SEQ ID NOs:29-32).

All PCR fragments were purified, and plasmid backbone, a promoter element (Plac_org, Plac, PglpF_org, PglpF, PglpT_org, PglpT, PglpA_org, PglpA, PglpD_org, PglpD, PglpF_SD1, PglpF_SD2, PglpF_SD3, PglpF_SD4, PglpF_SD5, PglpF_SD6, PglpF_SD7, PglpF_SD8, PglpF_SD9, PglpF_SD10, Δ15PglpF, Δ140PglpF, Δ165PglpF or Δ180PglpF), and lacZ were cloned, transformed into TOP10 cells and selected on LB plates containing 100 μ/ml ampicillin and 0.2% glucose. The constructed plasmids (see Table 10) were purified. The promoter sequence and the 5'end of the lacZgene was verified by DNA sequencing (MWG Eurofins Genomics).

Plasmid backbones based on pTOPO (ThermoFisher Scientific) or any other plasmid can be made in a similar way as described above. All plasmid backbones constructed contained two specific DNA fragments homologous to Escherichia coli K-12 DH1 used for homologous recombination. In this way, a genetic cassette containing the PglpF or Plac promoter, any gene of interest, and the T1 transcriptional terminator was inserted specifically in the Escherichia coli genome. Construction of plasmids used for recombineering was done using standard cloning techniques.

DNA sequences of heterologous genes coding for glycosyltransferases or other enzymes of interest were codon optimized and synthesized by Genescript. Any gene of interest e.g. host genes or the heterologous genes, lgtA, galT, galTK, futC, neuA, neuB, neuB, nst, or Pd2 (Table 9), could be amplified by PCR using appropriated primers covering the start codon, ATG and the stop codon, TAA, of the gene (Table 10). For instance, the Pd2 gene was amplified using primer O26 (SEQ ID NO:98) and O27 (SEQ ID NO:99), while the nst gene was amplified using the O95 and O93 (SEQ ID NOs:115 and 116) (Table 9). To construct donor plasmids with these genes, the following procedure was followed: A 3.5 kbp plasmid backbone containing the PglpF (SEQ ID NO: 12) was amplified using pMAP205 as template. The coding sequences of Pd2 gene from Photobacterium damselae (JT0160) (for ref. see Drouillart et al. 2010. Carbohydrate Research. 345: 1394-1399. *Efficient synthesis of 6'-sialyllactose, 6,6'-disiallyllactose, and 6'-KDO-lactose by metabolically engeineered E. coli expressing a multifunctional sialyltransferase from the Photobacterium sp. JT-ISH*-224) and nst gene from *Neisseria meningitides* (MC58) ((for ref. see Fierfort and Samian. 2008. J. Biotech. 134: 261-265. *Genetic engineering of Escherichia coli for the economical production of sialylated oligosaccharides*) were codon optimized for expression in *E. coli* and synthesized by Genescript. The genes, Pd2 and nst, were cloned in the plasmid backbones as described above resulting in plasmids pMAP216, pMAP228, pMAP99, pMAP391 (Table 3). The plasmids were purified, transformed into TOP10 cells and selected on LB plates containing 100 µ/ml ampicillin and 0.2% glucose. The promoter sequence and the 5'end of the Pd2 of nst gene were verified by DNA sequencing (MWG Eurofins Genomics).

In general and for any heterologous gene of interest, all PCR fragments were purified, and the plasmid backbone, glpF promoter element (SEQ ID NO:54), the synthetic DNA sequence (i) (70UTR/SEQ ID NO:37/synDNA(i)—see Table 1)) and the gene of interest was cloned by standard USER cloning. Cloning in an appropriated plasmid could be done using any standard DNA cloning technique. Following cloning the DNA was transformed into TOP10 cells and selected on LB plates containing 100 µ/ml ampicillin (or 50 mg/ml kanamycin in case of pTOPO-based constructs) and 0.2% glucose. The constructed plasmids were purified and the promoter sequence and the 5'end of the gene of interest were verified by DNA sequencing (MWG Eurofins Genomics).

Construction of Strains

Insertion of promoter expression elements fused to a reporter gene or a recombining gene was performed by Gene Gorging essentially as described by Herring et al (Herring, C. D., Glasner, J. D. and Blattner, F. R. (2003). Gene (311). 153-163). Briefly, the donor plasmid and the helper plasmid were co-transformed into MDO and selected on LB plates containing 0.2% glucose, ampicillin (100 µg/ml) or kanamycin (50 mg/mL) and chloramphenicol (20 µg/ml). A single colony was inoculated in 1 ml LB containing chloramphenicol (20 µg/ml) and 10 µl of 20% L-arabinose and incubated at 37° C. with shaking for 7-8 hours. Cells were then plated on M9-DOG plates and incubated at 37° C. for 48 hours. Single colonies formed on MM-DOG plates were re-streaked on LB plates containing 0.2% glucose and incubated for 24 hours at 37° C.

For insertions at the galK locus, colonies that appeared white on MacConkey-galactose agar plates and were sensitive for both ampicillin and chloramphenicol were expected to have lost the donor and the helper plasmid, and contain an insertion in the galK loci. Insertions in the galK site was identified by colony PCR using primers O48 and O49 located outside the galK loci. Chromosomal DNA was purified, the galK locus was amplified using primers O48 and O49 and the inserted DNA was verified by sequencing (Eurofins Genomics, Germany). Strains MAP1365, MAP1366, MAP1367, MAP1368, and MAP1370 were constructed using donor plasmids pMAP689, pMAP690, pMAP691, pMAP693, and pMAP695 resulting in insertion of pglpABC, pglpD, pglpTQ or pglpFKX, or plac fused to lacZ, respectively, in the galK locus of *E. coli* MDO.

Figures 6A, 6B:
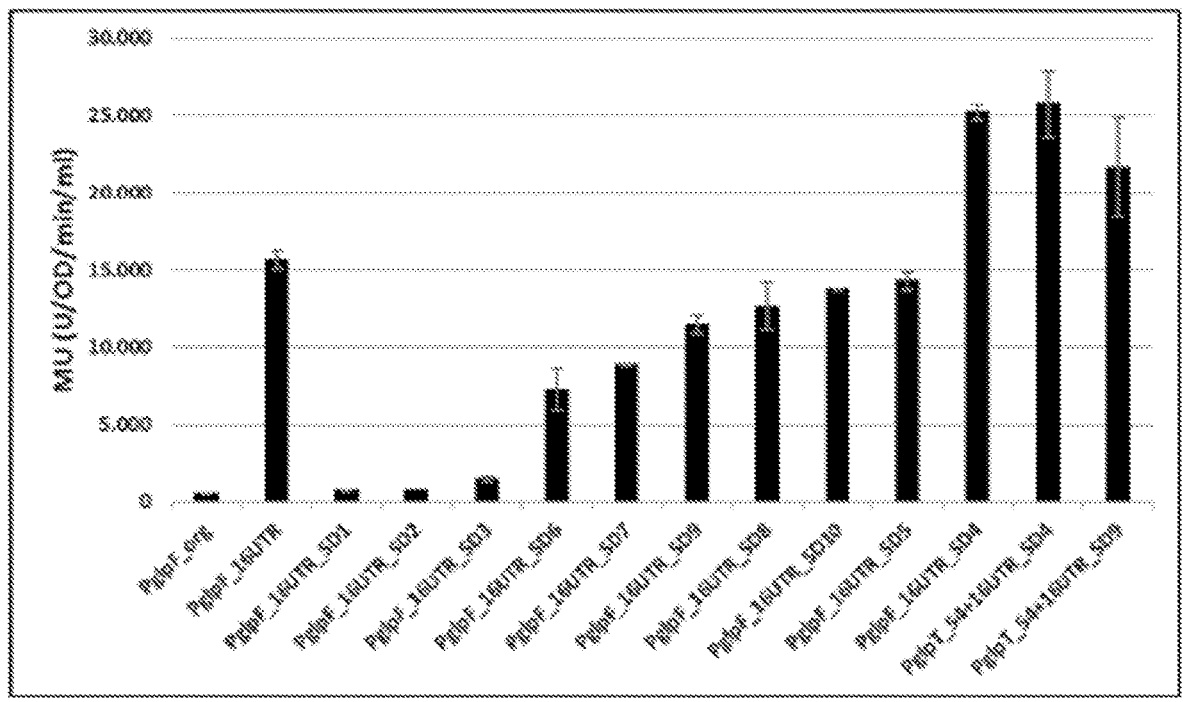

Strains MAP1025, MAP1026, MAP1027, and MAP808, were constructed using donor plasmids pMAP431, pMAP432, pMAP433, and pMAP205, respectively, resulting in insertion of PglpA, PglpD, PglpT, and PglpF, were the six-teen base pairs located upstream of the translational start site was change to 5'-CAAGGAGGAAACAGCT-3' (SEQ ID NO: 10), fused to lacZ and inserted in the galK locus of *E. coli* MDO Strains MAP1176 to MAP1185 were constructed using donor plasmids pMAP486 to pMAP495, respectively, resulting in insertion of PglpF_SD1, PglpF_SD2, PglpF_SD3, PglpF_SD4, PglpF_SD5, PglpF_SD6, PglpF_SD7, PglpF_SD8, PglpF_SD9 and PglpF_SD10 fused to lacZ and inserted in the galK loci of *E. coli* MDO. The modifications introduced in the Shine Dalgarno sequence of the PglpF expression element are shown in FIG. 6A and listed in Table 1.

Figures 7A, 7B:
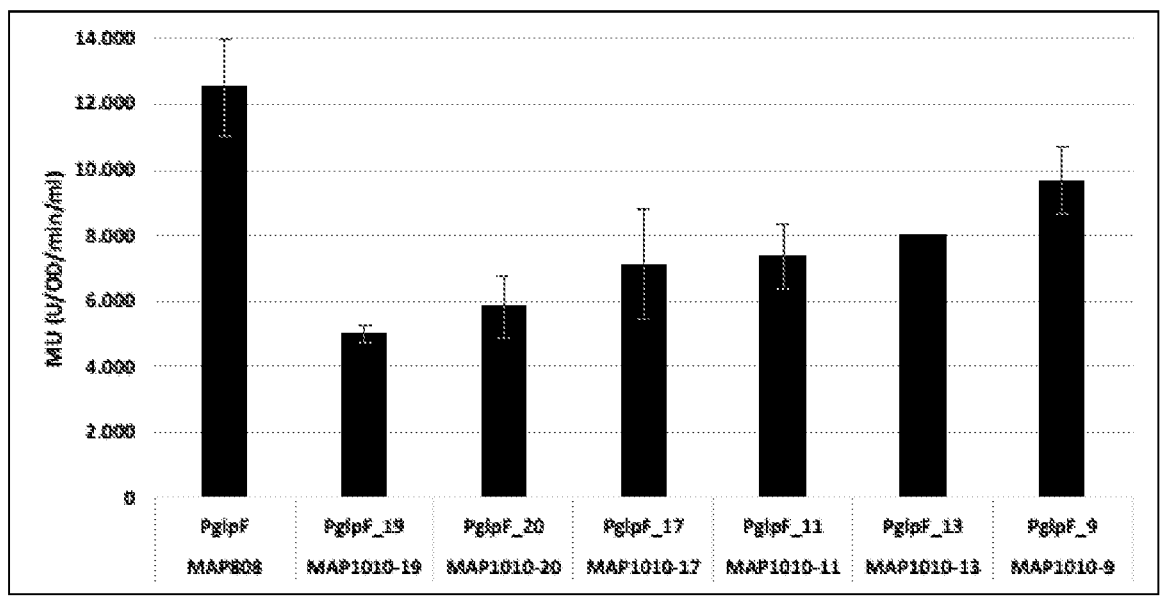

Strains MAP1010-9, MAP1010-11, MAP1010-13, MAP1010-17, MAP1010-19, and MAP1010-20 were constructed using a plasmid preparation generated by a degenerated primer. The modified PglpF expression element fused to lacZ was identified by sequencing and the promoter-lacZ fusion inserted into the galK locus of *E. coli* MDO. The modifications introduced in the −10 region of the PglpF expression element are shown in FIG. 7A and listed in Table 1.

Strains MAP1210, MAP1211, MAP1086, and MAP1209, were constructed using donor plasmids pMAP457, pMAP462, pMAP463, and pMAP537 resulting in insertion of the PglpF expression element deleted by 25, 150, 175, or 190 base pairs at the 5'-end. The truncated versions of the PglpF expression elements were fused to lacZ and inserted in the galK loci of *E. coli* MDO. The modifications of the PglpF expression elements are listed in Table 1.

Strain MAP1356 was constructed by double strand recombineering as described by Sharan et al (2009). Nat. Protoc. 4(29: 206-223). The glpR gene in MAP808 was replaced by a kanamycin resistant gene resulting in MAP1356.

MAP700 and MAP710: the strains were constructed using the helper plasmid and donor plasmids containing nst cassettes (PglpF- or Plac-based), resulting in *E. coli* MDO strains expressing the Nst glycosyltransferase.

MAP219 and MAP986: the strains were constructed using the helper plasmid and donor plasmids containing Pd2 cassettes (PglpF- or Plac-based) presulting in *E. coli* MDO strains expressing the Pd2 enzyme.

MDO1 and MDO15: Chemical competent *Escherichia coli* K-12 (DH1) MDO were transformed with 2 plasmids (Table 10) in order to produce LNnT and LNT, respectively. MP1497-MP1499: *Escherichia coli* K-12 (DH1) MDO was transformed with the helper plasmid pACBSR and donor plasmids containing the gene cassettes of interest (PglpF-IgtA or PglpF-galT) in order to integrate a given glycosyltransferase in the genome. The resulting hosts were subsequently transformed with a relevant plasmid harboring an antibiotic marker (Table 10).

MP166, MP245, MP1825, MP1920, MP2239, MP2374, MP2525: *Escherichia coli* K-12 (DH1) MDO was sequentially transformed with the helper plasmid pACBSR and donor plasmids containing the gene cassettes of interest to enable the integration of the corresponding modifications in its genome through gene gorging experiments (Table 10). MAP265 and MAP425: *Escherichia coli* K-12 (DH1) MDO was transformed with the helper plasmid pACBSR and donor plasmids containing gene cassettes of interest to enable the introduction of the desired integrations at the genome of the host by gene gorging. The nadC gene was deleted by insertion of galK into the nadC loci also by gene gorging. Finally, the strains were transformed with plasmid pMAP101 to create strains MAP265 and MAP425. MAP1200 and MAP1214: Escherichia coli K-12 (DH1) MDO was transformed with helper plasmid pACBSR and donor plasmids containing gene cassettes of interest to enable the introduction of the desired integrations at the genome of the host by gene gorging (Herring, C. D., Glasner, J. D. and Blattner, F. R. (2003). Gene (311). 153-163) (Table 10). All insertions were verified by sequencing (Eurofins Genomics, Germany).

Enzyme Assay: lacZ

The β-Galactosidase activity was assayed as described previously (see e.g. Miller J. H. Experiments in molecular genetics, Cold spring Harbor Laboratory Press, NY, 1972). Briefly the cells were diluted in Z-buffer and permeabilized with sodium dodecyl sulfate (0.1%) and chloroform. Assays were performed at 30° C. Samples were preheated, the assay initiated by addition of 200 µl ortho-nitro-phenyl-β-galactosidase (4 mg/ml) and stopped by addition of 500 µl of 1 M $Na_2CO_3$ when the sample had turned slightly yellow. The release of ortho-nitrophenol was subsequently determined as the change in optical density at 420 nm. The specific activities are reported in Miller Units [A420/(min*ml*A600)]. The activities listed in Table 7 are average values from at least two independent experiments.

Enzyme Assay: Heterologous Gene Expression of Pd2 and Δ29nst

Strains MAP219, MAP986, MAP700, and MAP710, were pre-cultured in 1 ml Basal media (see above) supplied with $MgSO_4$, Thiamine and glucose at 34° C. for 24 hours. The pre-culture, 0.5 ml, was inoculated in 50 ml Basal minimum media supplied with $MgSO_4$, Thiamine and 0.5% glycerol and incubated with shaking at 28° C. for 24 hours. 10 ml cell cultures were harvested in 50 ml falcon tubes at 8.000×g, at −10° C. for 15 minutes. The supernatant was removed, and the cell pellet stored at −80° C. until used.

The cell pellets were resuspended in 1 ml 1-X in vivo like media (125 mM KCl, 25 mM $K_3PO_4$, 10 mM Monosodium Glutamate, 0.001 mM $CaCl_2$, 5 mM $MgSO_4$ pH 7.5) containing 1× BugBuster (Merk Milipore). The cell samples were lysed by sonication 4 times 20 seconds at 30% amplitude. The insoluble cell debris was removed by centrifugation at 10.000×g for 10 minutes at −10° C. In the in vitro assay 5 mM CMP-SA was used as donor, and 10 mM lactose used as acceptor. Donor, acceptor, and lysate was mixed, and samples withdrawn after reaction of 0, 5, 10, 20, and 30 minutes. The samples were boiled for 10 minutes and the supernatant analyzed for 3'SL and 6'SL. The activity of the enzymes was measured as mM production of 6'SL or 3'SL per hour and corrected for cell OD.

and insertion of genetic cassettes was done by gene gorging as described below but could be done by any other technique using homologue DNA recombineering.

Deep Well Assay

A single colony from an LB-plate was pre-cultured in 1 ml Basal Minimum media containing glucose (0.5%) in a 10 ml 24 deep-well plate (Axygen). The plate was sealed before culturing with a Hydrophobic Gas Permeable Adhesive Seal (Axygen) and incubated for 24 hours at 34° C. with shaking at 700 rpm in an orbital shaker (Edmund Buhler GmbH). Cell density of the culture was monitored at 600 nm using an S-20 spectrophotometer (Boeco, Germany). 40 µl of the overnight culture was used for inoculation in 2 ml Basal Minimum media containing 0.01% glucose, 0.5% lactose, and 200 µg SUH (Sigma). IPTG were added if appropriated. The Deep well plates were covered with sealing foil and incubated for 48 or 72 hours at 28° C. with orbital shaking at 700 rpm. After incubation, OD600 was measured and the plate covered with sealing tape for heating (Saveen Werner) and incubated in a Thermomixer for 1 hour at 100° C. with shaking at 400 rpm. The cell lysate was pelleted by centrifugation for 10 minutes at 4.000 rpm. The HMO concentration in the supernatant was determined by HPLC or HPAC methods.

EXAMPLE 1

Cloning of 17 Randomly Selected Regulatory Elements Isolated from of E. coli

To identify single-copy number expression cassettes efficient for expression in an E. coli host strain, seventeen DNA fragments containing promoter elements were amplified from the E. coli K-12 DH1 chromosomal DNA. All promoter elements contained transcriptional regulatory binding sites, as well as binding site for the RNA polymerase (−35, −10 regions), transcriptional initiation sites, and a 5'-end untranslated sequence located 16 base pairs upstream of the translational initiation codon. A sixteen-nucleotide DNA sequence (5'-CAAGGAGGAAACAGCT-3') (SEQ ID NO: 10) covering the ribosomal binding site (including Shine-Dalgarno site) was introduced at the 3'-end in all DNA fragments using sequence specific oligos. Promoter names, lengths of promoter fragments, and oligos used for amplification and introducing SEQ ID NO:10 are listed in Table 11 below:

| Promoter Element | Base pairs amplified from DH1 | Oligo Name | Oligo Sequence | SEQ ID NO |
|---|---|---|---|---|
| PacnB | 334 | 0350 | ATGCGCAAAUCGGATCTCAAGGAAATCGCAATGG | SEQ ID NO: 60 |
|  |  | 0351 | AGCTGTTUCCTCCTTGCTCATTGTCATAGTGCGGCAGG | SEQ ID NO: 61 |
| Pactp | 134 | 0354 | ATGCGCAAAUGCTGAATCCGAACACCAGCGTC | SEQ ID NO: 62 |
|  |  | 0355 | AGCTGTTUCCTCCTTGGCAGGACTTCATTATTAAGACGG | SEQ ID NO: 63 |
| PdcuB | 584 | 0358 | ATGCGCAAAUTACTCACTACTGAAACAATATTGCC | SEQ ID NO: 64 |
|  |  | 0359 | AGCTGTTUCCTCCTTGTAATCCTATTTAAATTTTTGCTGAATAG | SEQ ID NO: 65 |
| Pdps | 182 | 0274 | ATGCGCAAAUCCGAAAATTCCTGGCGAGCAG | SEQ ID NO: 66 |
|  |  | 0275 | AGCTGTTUCCTCCTTGGATGTTATGTCCCAGTAATTAAC | SEQ ID NO: 67 |

-continued

| Promoter Element | Base pairs amplified from DH1 | Oligo Name | Oligo Sequence | SEQ ID NO |
|---|---|---|---|---|
| PgalP | 414 | 0360 | ATGCGCAAAUGAAGTAATCTTTCTTCACCTGCGTTC | SEQ ID NO: 68 |
|  |  | 0361 | AGCTGTTUCCTCCTTGGTTATTTTTTATTGTGAATTAAGATAGG | SEQ ID NO: 69 |
| PgapA | 355 | 0265 | ATGCGCAAAUCAGTTCTTCTGCCGAAGGTT | SEQ ID NO: 70 |
|  |  | 0266 | AGCTGTTUCCTCCTTGTTGTTAGTGAATAAAAGGTTGCC | SEQ ID NO: 71 |
| PglpA | 166 | 0378 | ATGCGCAAAUGAAAACATTCATAAATTAAATGTG | SEQ ID NO: 72 |
|  |  | 0379 | AGCTGTTUCCTCCTTGTTCGTTTTTTACCATTTAGC-CATAG | SEQ ID NO: 73 |
| PglpD | 173 | 0376 | ATGCGCAAAUGCGTCTCTCTTTCTTTACAAAC | SEQ ID NO: 74 |
|  |  |  | AGCTGTTUCCTCCTTGTTCGTTAAAGCTCATAAATGTTCG | SEQ ID NO: 75 |
| PglpF | 284 | 0261 | ATGCGCAAAUGCGGCACGCCTTGCAGATTACG | SEQ ID NO: 76 |
|  |  | 0262 | AGCTGTTUCCTCCTTGGTTAATGTTTGTTGTATGCG | SEQ ID NO: 77 |
| PglpT | 229 | 0380 | ATGCGCAAAUCCATTTAGCCATAGTAAAAACATG | SEQ ID NO: 78 |
|  |  | 0381 | AGCTGTTUCCTCCTTGCCGTGGTCTTATTTATGATTAAC | SEQ ID NO: 79 |
| PkatE | 254 | 0270 | ATGCGCAAAUGCGCGGGTTCCGTGCGTGGG | SEQ ID NO: 80 |
|  |  | 0271 | AGCTGTTUCCTCCTTGATTTATTACTGAAAGGGCCGC | SEQ ID NO: 81 |
| PkatG | 254 | 0272 | ATGCGCAAAUGTGATCACAAATTTTAAACAG | SEQ ID NO: 82 |
|  |  | 0273 | AGCTGTTUCCTCCTTGACAGTGTTACCGTTACGATAC | SEQ ID NO: 83 |
| Plac | 91 | 068 | ATGCGCAAAUTGTGAGTTAGCTCACTCATTAG | SEQ ID NO: 84 |
|  |  | 0268 | AGCTGTTUCCTCCTTGAAATTGTTATCCGCTCACAA | SEQ ID NO: 85 |
| Pmlc | 134 | 0257 | ATGCGCAAAUGAATGCTCTCAGGTGAGGG | SEQ ID NO: 86 |
|  |  | 0258 | AGCTGTTUCCTCCTTGTTTCGCGCTCCGAAATAATC | SEQ ID NO: 87 |
| PpoxB | 184 | 0366 | ATGCGCAAAUCCGAAATCGCTGAAGGTTACGTAC | SEQ ID NO: 88 |
|  |  | 0367 | AGCTGTTUCCTCCTTGAATGTGATAACGGTAACAAGTTTAG | SEQ ID NO: 89 |
| PptsG | 384 | 0255 | ATGCGCAAAUGGCTGTGTTGAAAGGTGTTG | SEQ ID NO: 90 |
|  |  | 0256 | AGCTGTTUCCTCCTTGAGTATGGGTGCTTTTTTTACG | SEQ ID NO: 91 |
| PptsH | 382 | 0259 | ATGCGCAAAUGAATTGCAACAGTAATGCCAG | SEQ ID NO: 92 |
|  |  | 0260 | AGCTGTTUCCTCCTTGATAGGTTTAGTGTTGTGGAAC | SEQ ID NO: 93 |

Figure 1A:
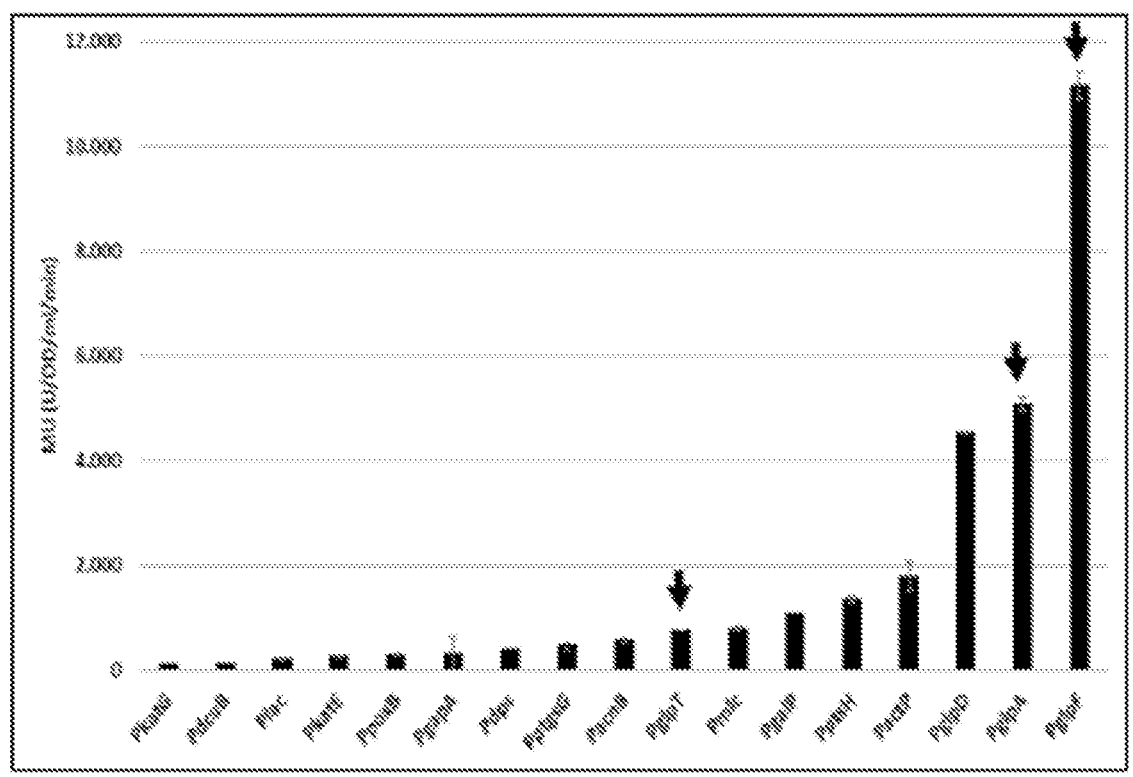
FIG. 1 presents
(A) The expression levels of reporter gene (lacZ) from nucleic acid constructs comprising seventeen different promoter elements combined with SEQ ID NO:10. Every expression cassette comprising a single promoter also comprises a native 5'UTR sequence (downstream the promoter and upstream SEQ ID NO:10) of the gene which is naturally transcribed from the promoter of the construct. (B) The expression levels of lacZ from the expression cassettes of (A) comprising selected promoters—PglpT, PglpA and PglpF, (dashed bars; b) compared to the expression levels of lacZ from expression cassettes comprising the promoter and the original 5'UTR DNA fragment of the corresponding gene, i.e. glpT, glpA and glpF (open bars; a).

The cloned seventeen DNA fragments (17-Promoters), are all identical at the 3'end (SEQ ID NO:10), were all fused to a promoter-less lacZ gene linked to a transcriptional terminator sequence, T1. A single copy of the lacZ expression cassette, Promoter-SEQ ID NO:10-lacZ-T1, was integrated into the chromosomal DNA. The expression activity of the lacZ gene introduced in a single copy was measured as the activity of the β-galactosidase. The activity of the lac promoter was measured in the presence of IPTG. The results of expression of the reporter gene from the constructs are shown in FIG. 1A. Notably, not all tested promoters demonstrated an increase activity following substitution of the native 16-nucleotide fragment upstream of the translation initiation codon comprising a ribosomal binding site (RBS) for SEQ ID NO:10. A remarkable activity was observed for glpF promoter, activity of both glpA and D was also significant, but activity of the majority of the tested promoters was either not changed at all or did not increase to a significant extend (which could be expected according to Meynial-Salles I, et al (2005) *Appl Eviron Microbiol* 71:2140-2144; and WO 03/089605).

Figure 1B:
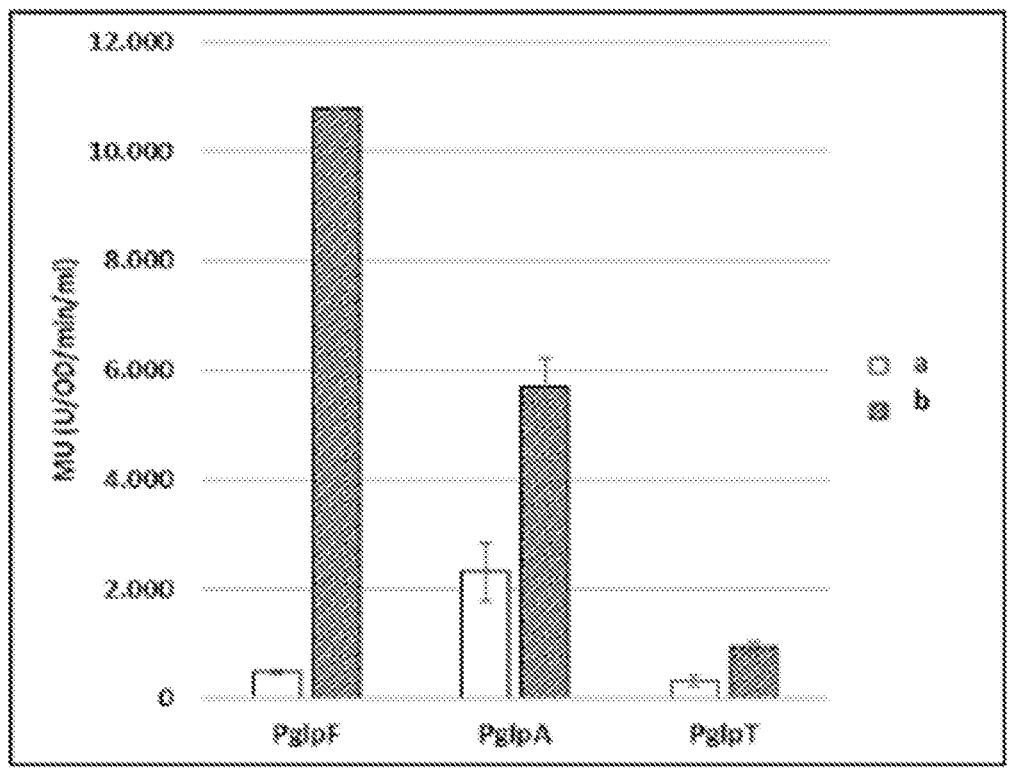

FIG. 1B presents data on expression of the reporter gene from constructs comprising three representative promoters of FIG. 1A (PglpF, PglpA and PglpT) and either the native 16-nucleotide sequence derived from the 5'UTR DNA upstream the corresponding gene (i.e. glpF, glpA and glpT) or SEQ ID NO:10.

FIG. 2 shows the comparison of the levels of expression of the reporter gene from a promoter sequence isolated from the glp operons: glpFKX, glpABC, glpTQ, and glpD. All the promoters are negatively regulated by GlpR repressor. All cloned DNA fragments contained DNA binding's sites for cAMP-CRP plus a number of other regulatory elements, such as one or more sites for binding of GlpR repressor. A schematic view of the cloned promoter elements is shown in FIGS. 2 and 3 The cloning was done as described above.

EXAMPLE 2

Expression Level from Single Copy Pglp-lacZ Fusions

A promoter-probe plasmid containing a promoter-less lacZ gene was used as a cloning system to identify *E. coli* promoter elements that could sustain high and regulated protein expression. The expression levels of lacZ was determined both from a single copy of Pglp-lacZ integrated into the chromosomal DNA and from a high-copy-number plasmid (as described in Example 11). The ΔlacZM15 deletion in the lacZ gene in E. coli MDO is unable to produce an active β-galactosidase enzyme and was therefore used as strain background in the screen. As a positive reference for lacZ expression the Plac promoter element was used. Promoter elements originating from the glp operons, glpTQ, glpACB, glpD, and glpFKX, or Plac were fused to the promoter-less lacZ gene and inserted into the genome of Escherichia coli by site specific recombineering resulting in strains MAP1367, MAP1365, MAP1366, MAP1368, and MAP1370, respectively. All isolated promoter DNA fragments, pglpTQ, pglpACB, pglpD, pglpFKX, and plac fused to lacZ could express the β-galactosidase enzyme and the activity of the enzyme was measured as shown in FIG. 4. Note that the activity of the Plac promoter was measured in the presence of IPTG. In another set of experiments, the 16 base pair nucleotide sequence located upstream of the translational start sites in glpF, glpA, glpD, glpT, and lacZ genes, included in the expression cassettes comprising pglpFKX, pglpACB, pglpD, and pglpTQ, were modified to sequence: 5'-CAAGGAGGAAACAGCT-3'(SEQ ID NO:10) resulting in strains MAP808, MAP1025, MAP1026, and MAP1027, respectively. Modification of the 16 base pairs upstream of translational start site in the constructs comprising the promoter elements PglpF, PglpA and PglpT and an original 5'UTR DNA fragment of the corresponding glp gene increased expression of the β-galactosidase enzyme by approximately 10. 000-fold for PglpF, 2-fold for PglpA and PglpT (FIG. 4). Surprisingly, the further substitution of the original 54-nucleotide 5'UTR DNA sequence located downstream of the transcription start in PglpA and PglpT constructs for SEQ ID NO:36 from 5'UTR DNA of the glpF gene (resulting in the DNA constructs PglpA_70UTR (SEQ ID NO:50) and PglpT_70UTR (SEQ ID NO:51)) resulted in a great increase of the reporter gene expression from these constructs (FIG. 4), demonstrating an unexpected synergetic effect of the 70UTR sequence of the gene expression.

TABLE 12

Primers used for the construction of PglpA_70UTR and PglpT_70UTR

| PglpA_70 UTR | 0378 | ATGCGCAAAUGAAAACATTCA TAAATTAAATGTG | SEQ ID NO: 94 |
|---|---|---|---|
| | 0812 | AGCTGTTUCCTCCTTGGTTAA TGTTTGTTGTATGCGTGAAAG TCACGGACCTCCACGATGCTT GTAGGCATCGCGCATATTCGC TCATAATTC | SEQ ID NO: 95 |
| PglpT_70 UTR | 0380 | ATGCGCAAAUCCATTTAGCAT AGTAAAAACATG | SEQ ID NO: 96 |
| | 0815 | AGCTGTTUCCTCCTTGGTTAA TGTTTGTTGTATGCGTGAAAG TCACGGACCTCCACGATGCTT GTAGGCATGCCGCGATGTTAA GAAAAC | SEQ ID NO: 97 |

EXAMPLE 3

Expression Level from Single Copy Pglp-lacZ Fusions is Catabolic Repressed

Since expression from the glp promoters are known to be catabolically repressed, the level of expression of the Pglp-lacZfusions containing SEQ ID NO:10 were measured. Strains MAP808, MAP1025, MAP1026, and MAP1027, were grown in the presence or absence of glucose and the activity of the β-galactosidase encoded by lacZ was determined (Table 13). In both LB and minimal media the expression level was significantly reduced in the presence of glucose.

TABLE 13

Expression levels from Pglp-lacZ fusions in single copy

| Strain | Promoter Element | LB (MU) | LB-glucose (MU) | Fold repression | MM-Glycerol | MM-Glucose | Fold repression |
|---|---|---|---|---|---|---|---|
| MAP808 | PglpF | 8.850 ± 1.415 | 279 ± 3 | 32 | 13.450 ± 786 | 3.699 ± 353 | 4 |
| MAP1025 | PglpA | 3.732 ± 234 | 72 ± 70 | 51 | 5.677 ± 154 | 1.874 ± 332 | 3 |
| MAP1026 | PglpD | 3.969 ± 603 | 618 ± 223 | 6 | 4.529 ± 132 | 1.398 ± 121 | 3 |
| MAP1027 | PglpT | 647 ± 23 | 15 ± 15 | 43 | 1.110 ± 139 | 290 ± 44 | 4 |

EXAMPLE 4

Expression from Single Copy PglpF-lacZ is Regulated and Affected by the Carbon Source in the Media To determine if the expression level from PglpF-lacZ is regulated by other carbon sources than glucose strain MAP808, which comprises a single copy of the PglpF-lacZ fusion, was grown in LB media with and without glucose, and in minimal media using glycerol, sorbitol, maltose or glucose as the sole carbon source. High expression of lacZ was observed in LB media, however, addition of 0.2% glucose significantly reduced expression of lacZ (32-fold) in LB media (Table 13, FIG. 5). High expression of lacZ in strain MAP808 was observed in Minimal media when glycerol or sorbitol was used as the sole carbon source, whereas using maltose or glucose in minimal media reduced the expression of lacZ.

EXAMPLE 5

The Expression Level from PglpF and T Constructs can be Modified Significantly by Altering the Ribosomal Binding Site Comprised in SEQ ID NO:10

The effect of modifications of the recombining sequence (SEQ ID NO:10) comprising a ribosomal binding site (Sine Dalgarno sequence) from the constructs comprising PglpF and PglpT (SEQ ID NOs:54 and 49) and the 70UTR sequence (SEQ ID NO:37) on gene expression was determined by measuring, the expression level of the reporter gene (lacZ) expressed from different PglpF and PglpT constructs comprising variants of SEQ ID NO:10, as shown in FIG. 6. The expression level of lacZ was significantly altered (reduced by 9%-95%, or increased by 60%) (FIG. 6).

EXAMPLE 6

The Expression Level From PglpF can be Modified by Altering the Sequence of the −10 region Base pair modifications were introduced in the −10 region: 5'-TAAGT-3' of the 310 bp PglpF expression element resulting in strains MAP1010-19, MAP1010-20, MAP1010-13, MAP1010-17, MAP1010-11, and MAP1010-9. The expression level of lacZ was measured in each strain and the results showed that the expression of lacZ was reduced from 16% and up to 60% showing the importance of the −10 region for altering the level of expression (FIG. 7).

EXAMPLE 7

A 120 bp Fragment Comprising PglpF Contains a Functional Promoter

The activity of the PglpF was examined by truncating 15, 140, 165, or 180 base pairs from the 5'-end resulting in strains MAP1210, MAP1211, MAP1086, and MAP1209, respectively. The expression level of lacZ was measured in each strain and the results show that expression from PglpF is maintained even if the PglpF sequence is reduced from 300 base pairs to 120 base pairs (FIG. 8).

EXAMPLE 8

Removing the Transcriptional Repressor GlpR Increase Expression from the PglpF Element The PglpF promoter is known to be negatively regulated by the transcriptional repressor protein, GlpR. The PglpF of 300 base pairs contains four binding sites for the GlpR repressor protein (FIG. 2). To determine the importance of the GlpR repressor on transcription from PglpF the repressor gene, glpR, was knocked out resulting in strain MAP1356. The expression level of lacZ was measured in the absence and presence of GlpR repressor and the expression level was elevated by nearly 20% in its absence (FIG. 9).

EXAMPLE 9

Expression of Recombinant Genes Using the PglpF Expression Element is Affected by the Carbon Source Used in the Growth Media Growing cells in different media have a significant impact on the level of LacZ expressed from PglpF (FIG. 5). To test if heterologous genes can be expressed from the PglpF promoter element linked to the 70UTR DNA sequence, and if expression is affected by the carbon source used in the media, strain MAP710 and MAP986, expressing the trans-sialidase nst or Pd2 from PglpF in single copy, respectively, were constructed and cultivated in minimal media containing either glucose or glycerol as carbon source. When glycerol was used as carbon source the enzymatic activity was at least 7-fold higher than when cells were grown in media containing glucose as carbon source (FIG. 10) showing that recombining genes can be expressed using PglpF and that this expression can be regulated by the carbons source present in the media.

EXAMPLE 10

High Expression of Recombinant Genes Using the PglpF Expression Element Compared to Using the Plac Promoter Element Heterologous gene expression from the constructs PglpF-70UTR-Pd2 and PglpF-70UTR-nst fusions were determined from single copies integrated into the host chromosome followed by measurement of the enzymatic activities of the expressed proteins. The enzymatic activities were measured in cell lysates expressing Pd2 from the Plac promoter (induced with IPTG) or from the PglpF promoter (FIG. 10). The production of 6'SL is 7-fold higher in cell lysates expressing Pd2 from PglpF compared to Plac. In a similar way, the enzymatic activity from a cell lysate expressing the nst siallyltransferase from the Plac promoter (induced with IPTG) or from the PglpF promoter (FIG. 10) showed an almost 14-fold higher activity when nst was expressed from PglpF than from Plac.

EXAMPLE 11

The PglP-Containing Nucleic Acid Constructs Can be Used For Expression from Multi Copy Number Plasmids The PglpF, PglpA, and PglpT nucleic acid constructs, all contain the promoter DNA fragment isolated from the corresponding glp operons and a synthetic DNA sequence containing a sequence of the 5'UTR DNA isolated from the corresponding promoter that has been fused to SEQ ID NO:10 and placed upstream of the translational start site of the reporter gene (lacZ). The constructs were cloned into a high copy number plasmid. The expression levels of lacZ was measured as the activity of the β-galactosidase enzyme in cells grown in LB media in the presence or absence of glucose (Table 14, FIG. 11). The results in table 4 shows that the Pglp supports high expression from high copy number plasmids and that the expression is regulated by catabolic repression in the presence of glucose (Table 14, FIG. 11).

TABLE 14

| Plasmid | Promoter Element | Original Operon | Activity in LB (MU) | Activity in LB-glucose (MU) |
|---|---|---|---|---|
| pMAP205 | PglpF | glpFKX | 51.245 ± 4.560 | 6.664 |
| pMAP431 | PglpA | glpACB | 27.377 ± 549 | 457 ± 469 |
| pMAP433 | PglpT | glpTQ | 11.019 ± 575 | 400 ± 10 |

EXAMPLE 12

Figure 12A:
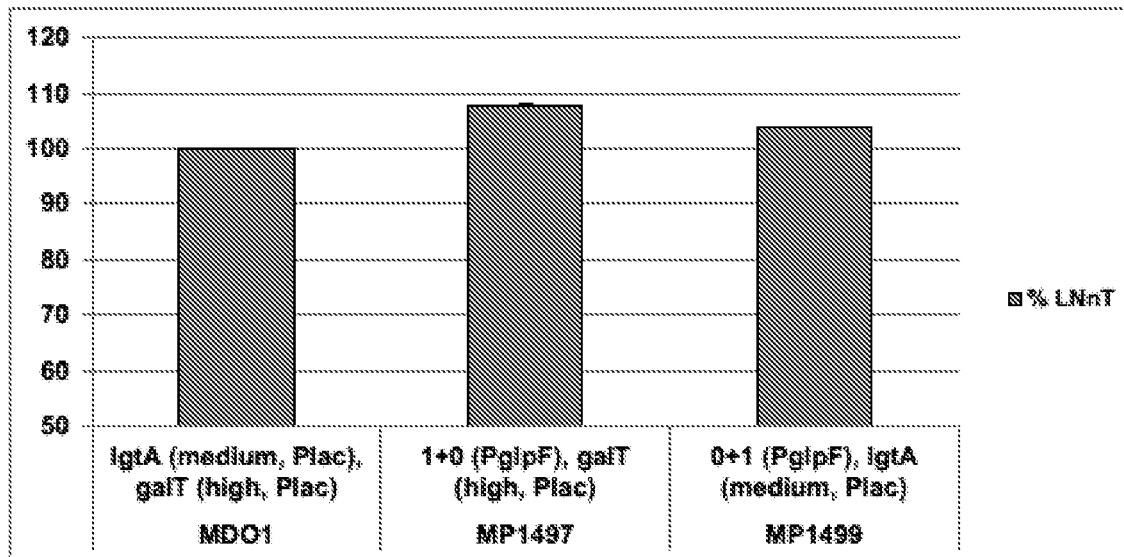
Figure 12B:
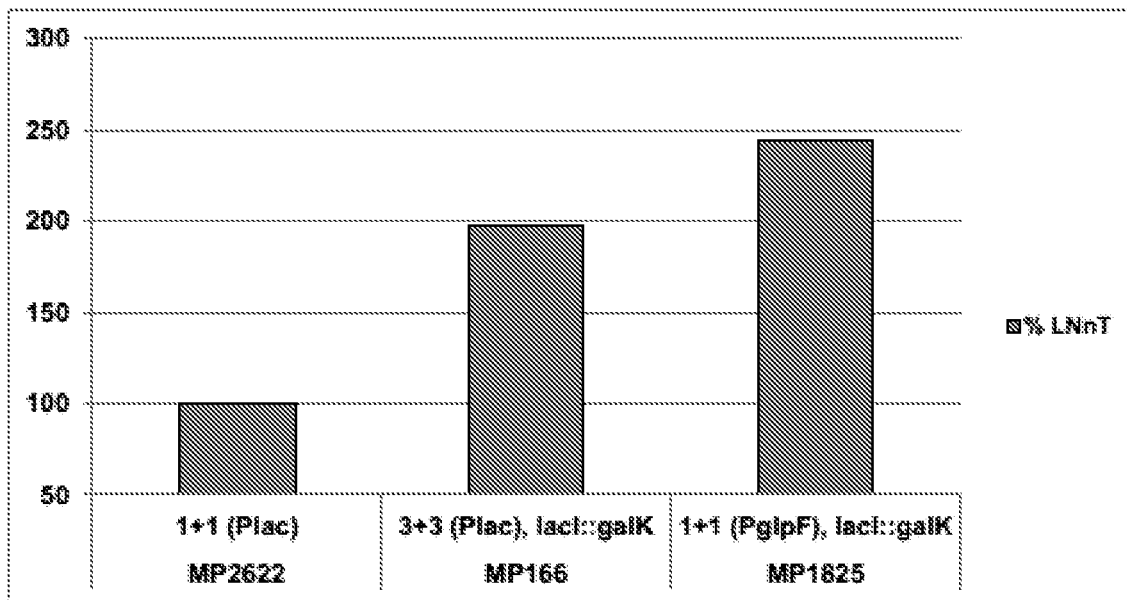

Engineering of *Escherichia coli* for LNnT Production Using the PglpF Promoter The *Escherichia coli* K-12 (DH1) MDO strain can be manipulated to episomically express heterologous genes of interest. For instance, the strain MDO1 is a 2-plasmid strain with a medium-copy number plasmid (30-40 copies per cell) bearing the lgtA gene and a high-copy number plasmid (300-500 copies per cell) with the galT gene. The Plac promoter controls the expression of both heterologous genes in these plasmids. Alternatively, heterologous genes can be integrated in the genome of the *Escherichia coli* K-12 (DH1) MDO strain to generate genome-engineered production systems. In this manner, the medium-copy plasmid with the IgtA gene is replaced by a single genomic copy of the PglpF-IgtA expression cassette in strain MP1497, which still bears the high-copy number plasmid with Plac-galT. In another example, the high-copy number plasmid with the galT gene is replaced by a single genomic copy of the PglpF-galT expression cassette in strain MP1499, which still bears the medium-copy number plasmid with Plac-IgtA. As shown in FIG. 12A, similar LNnT titers is reached when the expression of both heterologous genes, IgtA and galT, are expressed from a plasmid-borne Plac promoter (strain MDO1) or when one of the genes is expressed from the PglpF promoter fragment integrated into the chromosomal DNA and the second gene is expressed from a plasmid-borne Plac promoter (strains MP1497 and MP1499).

The strains MP2622 and MP1825 express the IgtA and galT genes from a single genomic copy under the control of the Plac or PglpF promoter, respectively. The strain MP166 has three Plac-controlled genomic copies of both genes. Except from the strain MP2622, the lacI gene is deleted from the genome of the strains discussed here, and the CP6-galK cassette is inserted at the lacI locus. It is obvious from the histograms in FIG. 12B that expression of the IgtA and galT genes from a single, PglpF-controlled genomic copy (strain MP1825) suffices to reach LNnT titers that are much higher than the ones achieved when single (strain MP2622) or multiple (strain MP166) Plac-controlled IgtA and galT genomic copies are integrated in the genome.

EXAMPLE 13

Engineering of *Escherichia coli* for LNT Production Using the PglpF Promoter

Figure 13A:
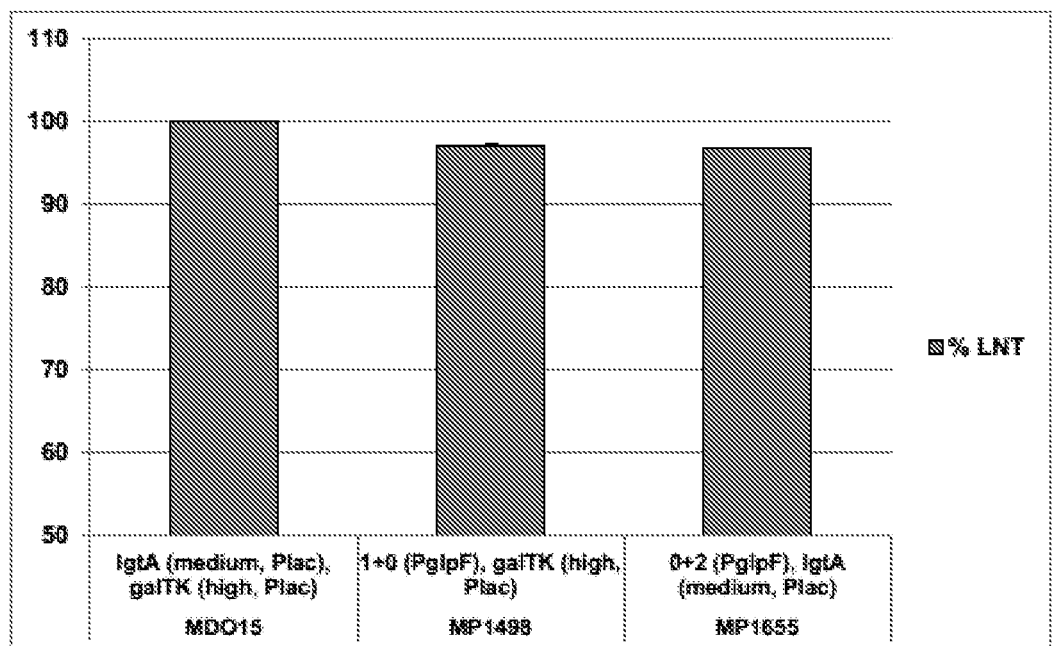
Figure 13B:
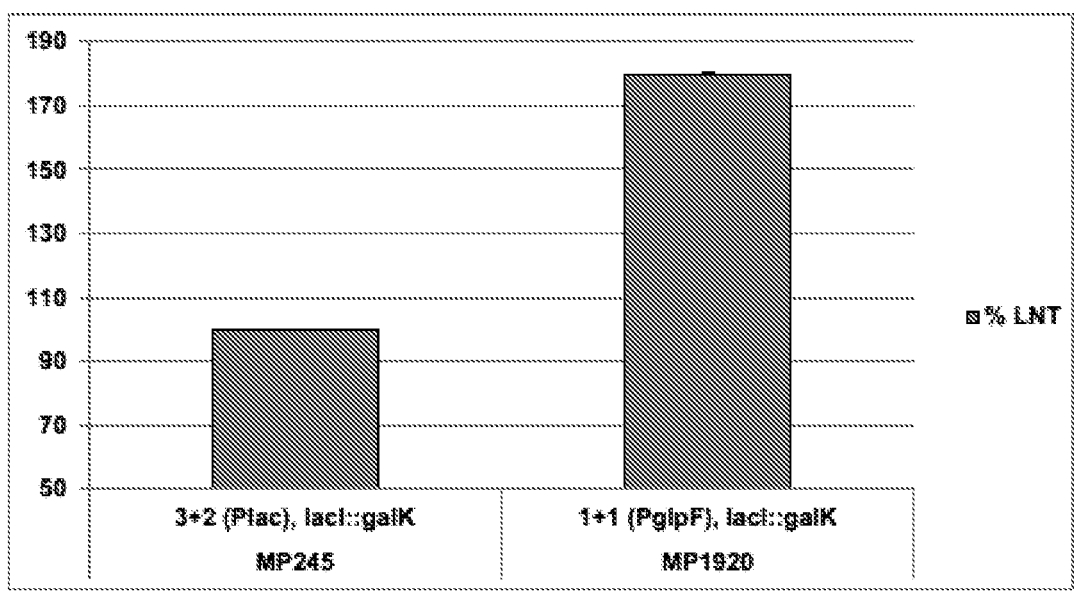

The *Escherichia coli* K-12 (DH1) MDO strain can be manipulated to episomically express heterologous genes of interest. The strain MDO15 is a 2-plasmid strain with a medium-copy number plasmid (30-40 copies per cell) bearing the IgtA gene and a high-copy number plasmid (300-500 copies per cell) with the galTK gene. The expression of both heterologous genes in these plasmids is controlled by the Plac promoter. Alternatively, heterologous genes can be integrated in the genome of the *Escherichia coli* K-12 (DH1) MDO strain to generate genome-engineered production systems. In this manner, the medium-copy number plasmid with the IgtA gene is replaced by a single copy of the PglpF-IgtA expression cassette in strain MP1498, which still bears the high-copy number plasmid with Plac-galTK (FIG. 13A). In another example, the high-copy number plasmid with the galTK gene is replaced by two genomic copies of the PglpF-galTK expression cassette in strain MP1655, which still bears the medium-copy number plasmid with Plac-IgtA (FIG. 13A). As shown in FIG. 13A, similar LNT titers can be reached when the expression of both heterologous genes, IgtA and galTK, is controlled by a plasmid-borne Plac promoter (strain MDO15) or when the expression of IgtA is driven by a PglpF-IgtA cassette inserted in the chromosomal DNA of the host and the plasmid-borne Plac promoter controls the expression of the galTK gene (strain MP1498). Similar product titers can also be achieved when two genomically integrated PglpF-IgtA cassettes drive the expression of the galTK gene and the expression of IgtA is under the control of a plasmid-borne Plac promoter (strain MP1655 in FIG. 13A).

The expression of three IgtA and two galTK genomic copies in strain MP245 is under the control of the Plac promoter. A single copy of each heterologous gene is expressed from the PglpF promoter in the strain MP1920. The lacI gene is deleted from the genome of these strains by insertion of the CP6-galK cassette at the lacI locus. It is obvious from the graphs in FIG. 13B that expression of the IgtA and galTK genes from a single, PglpF-controlled genomic copy (strain MP1920) reaches LNT titers that are much higher than the ones achieved when multiple Plac-controlled IgtA and galT genomic copies (strain MP245) are integrated in the chromosome.

EXAMPLE 14

Engineering of *Escherichia coli* for LNFP-I Production Using the PglpF Promoter An LNFP-I genome-engineered production system can be developed by integrating relevant heterologous genes in the genome of the *Escherichia coli* K-12 (DH1) MDO strain. For instance, the strain MP2239 expresses the heterologous genes IgtA, galTK and futC from a single genomic copy under the control of the PglpF promoter, while the expression of the colanic acid (CA) genes gmd, wcaJ (fcl), wcaH (gmm), wcaI, cpsB (manC), and cpsG (manB) is Plac-driven. Integration of an extra genomic copy of the CA genes in strain MP2239 under the control of the PglpF promoter results in strain MP2374. The lacI gene is deleted from the genetic background of both strains. A marked improvement of the LNFP-I titer is observed when an extra copy of the CA genes is integrated in strain MP2239 and expressed from the PglpF promoter (FIG. 14).

EXAMPLE 15

Engineering of *Escherichia coli* for 3'SL Production Using the PglpF Promoter

In strain MAP425 the Plac promoter was used to express i) the heterologous gene nst, and the heterologous gene cluster neuBCA integrated into the chromosome of *Escherichia coli* K-12 (DH1) MDO and ii) the heterologous gene cluster neuBCA from a multi-copy number plasmid (300-500 copies per cell). In strain MAP1214 the PglpF promoter was used to express the heterologous genes nst, neuA, neuB, and neuC, integrated in single copies into the chromosome of *Escherichia coli* K-12 (DH1) MDO. As shown in FIG. 15, similar 3'SL titers were reached when Plac was used for expressing the gene cluster neuBCA from a multi-copy number plasmid (strain MAP425), and when PglpF was used for expressing nst, neuA, neuB, and neuC from single integrated gene copies (strain MAP1214) (FIG. 15).

EXAMPLE 16

Engineering of *Escherichia coli* for 6'SL Production Using the PglpF Promoter

In strain MAP265 the Plac promoter was used to express i) the heterologous gene Pd2 introduced into the chromosome of *Escherichia coli* K-12 (DH1) MDO and ii) the heterologous gene cluster neuBCA from a multi-copy number plasmid (300-500 copies per cell). In strain MAP1200 the PglpF promoter fragment was used to express the heterologous genes Pd2, neuA, neuB, and neuC, integrated in single copies into the chromosome of *Escherichia coli*

K-12 (DH1) MDO. As shown in FIG. 16, the 6'SL titer was significantly higher when PglpF was used for expression of Pd2, neuA, neuB, and neuC, from single integrated gene copies than when Plac was used for expression of the gene cluster neuBCA from a multi-copy number plasmid (strain MAP265) (FIG. 16).

EXAMPLE 17

Engineering of *Escherichia coli* for 2'FL Production Using the PglpF Promoter

The strain FT18 is a 2-plasmid strain with a medium-copy number plasmid (30-40 copies per cell) bearing the CA genes gmd, wcaJ (fcl), cpsB (manC) and cpsG (manB), isolated from *Escherichia coli* K-12 DH1, and a high-copy number plasmid (300-500 copies per cell) with the futC gene. The Plac promoter controls the expression of the cloned genes in these plasmids. The expression of futC and the CA genes gmd, wcaJ (fcl), cpsB (manC) and cpsG (manB) in strain MP965 is under the control of the PglpF promoter. A single copy of futC and the colonic acid genes are expressed from the PglpF promoter in the strain MAP965. The results presented in FIG. 17 show that expression of futC and the CA genes from a single, PglpF-controlled genomic copy (strain MAP965) reaches almost the same 2'FL titers as when the genes are expressed from multiple gene copies controlled by Plac (FIG. 17).

The invention claimed is:

1. A synthetic nucleic acid construct comprising a synthetic non-coding DNA sequence (i) that comprises a first DNA fragment and a second DNA fragment,
wherein the first DNA fragment is a DNA sequence derived from the 5'-untranslated region (5'-UTR) of a glp gene of *Escherichia coli* and is located upstream from the second DNA fragment; and
wherein the nucleotide sequence of the second DNA fragment is selected from the group consisting of SEQ ID NO: 10, 38, 39, 40, 41, 42, 43, 44, 45, 46 and 47.

2. The nucleic acid construct of claim 1, further comprising a promoter DNA sequence (ii), wherein the promoter DNA is operably linked to the synthetic non-coding DNA sequence (i) and located upstream of the first DNA fragment of the synthetic non-coding DNA sequence (i).

3. The nucleic acid construct of claim 2, wherein the promoter DNA sequence (ii) comprises a promoter DNA sequence capable of initiating transcription of the glpFKX, glpABC, glpD or glpTQ operon of *Escherichia coli*.

4. The nucleic acid construct of claim 3, wherein the nucleotide sequence of the promoter DNA sequence (ii) is selected from the group consisting of SEQ ID NO: 1, 2, 3, 4, 48, 49 and 54.

5. The nucleic acid construct of claim 1, further comprising a coding DNA sequence (iii), wherein the coding DNA sequence (iii) is operably linked to the synthetic non-coding DNA sequence (i) and located downstream of the second fragment of the synthetic non-coding DNA sequence (i).

6. The nucleic acid construct of claim 5, wherein the coding DNA sequence (iii) encodes a protein or a RNA.

7. The nucleic acid construct of claim 6, wherein the protein or RNA has a function that is essential or beneficial for the production of one or more human milk oligosaccharides (HMOs) in a recombinant organism.

8. The nucleic acid construct of claim 1, wherein the glp gene is selected from the group consisting of glpF, glpA and glpD.

9. The nucleic acid construct of claim 1, wherein the first DNA fragment of the synthetic non-coding DNA sequence (i) comprises from about 5 to about 65 contiguous nucleotides downstream of the transcription start of the glp gene.

10. The nucleic acid construct of claim 9, wherein the glp gene is glpF.

11. The nucleic acid construct of claim 1, wherein the first DNA fragment is or comprises SEQ ID NO: 36, a fragment thereof.

12. The nucleic acid construct of claim 1, wherein the construct comprises a nucleotide sequence selected from of the group consisting of SEQ ID NOs:13-27 and 28.

13. The nucleic acid construct of claim 1, wherein the construct is an expression cassette that is integrated in the genomic or plasmid DNA of a recombinant organism.

14. The nucleic acid construct of claim 1, wherein in the synthetic non-coding DNA sequence (i) is or comprises SEQ ID NO: 37.

15. A recombinant cell comprising the synthetic nucleic acid construct of claim 1.

16. The recombinant cell of claim 15, wherein the cell is *E. coli*.

17. The recombinant cell of claim 15, wherein the cell comprises more than one copy of the same nucleic acid construct.

18. The recombinant cell of claim 15, wherein the cell comprises at least two different nucleic acid constructs.

19. The recombinant cell of claim 18, wherein the nucleic acid constructs differ either/both in the promoter DNA sequence (ii), synthetic non-coding DNA sequence (i) or/and coding DNA sequence (iii).

20. An expression system comprising the recombinant cell of claim 15.

* * * * *

SEQUENCE LISTING

```
<160> NUMBER OF SEQ ID NOS: 117

<210> SEQ ID NO 1
<211> LENGTH: 284
<212> TYPE: DNA
<213> ORGANISM: Artificial Sequence
<220> FEATURE:
<223> OTHER INFORMATION: 284-nucleotide DNA fragment derived from
      genomic DNA of E. coli (ref. seq ID U00096.3) located 16 bp
      upstream the glpF translation initiation codon

<400> SEQUENCE: 1
gcggcacgcc ttgcagatta cggtttgcca cacttttcat ccttctcctg gtgacataat      60
ccacatcaat cgaaaatgtt aataaatttg ttgcgcgaat gatctaacaa acatgcatca     120
tgtacaatca gatggaataa atggcgcgat aacgctcatt ttatgacgag gcacacacat     180
tttaagttcg atatttctcg tttttgctcg ttaacgataa gtttacagca tgcctacaag     240
catcgtggag gtccgtgact ttcacgcata caacaaacat taac                      284

<210> SEQ ID NO 2
<211> LENGTH: 166
<212> TYPE: DNA
<213> ORGANISM: Artificial Sequence
<220> FEATURE:
<223> OTHER INFORMATION: 166-nucleotide DNA fragment derived from
      genomic DNA of E. coli (ref. seq ID U00096.3) located 16 bp
      upstream of the glpA translation initiation codon

<400> SEQUENCE: 2
gaaaacattc ataaattaaa tgtgaattgc cgcacacatt attaaataag atttacaaaa      60
tgttcaaaat gacgcatgaa atcacgtttc actttcgaat tatgagcgaa tatgcgcgaa     120
atcaaacaat tcatgttttt actatggcta aatggtaaaa aacgaa                    166

<210> SEQ ID NO 3
<211> LENGTH: 174
<212> TYPE: DNA
<213> ORGANISM: Artificial Sequence
<220> FEATURE:
<223> OTHER INFORMATION: 174 bp DNA fragment derived from genomic DNA of
      E. coli (ref. seq ID U00096.3). located 16 bp upstream of the glpD
      translation initiation codon

<400> SEQUENCE: 3
tgcgtctctc tttctttaca aacaagtggg caaatttacc gcacagttta cgtcgaagcg      60
gcagataaac gccataatgt tatacatatc actctaaaat gttttttcaa tgttacctaa     120
agcgcgattc tttgctaata tgttcgataa cgaacattta tgagctttaa cgaa          174
```

```
<210> SEQ ID NO 4
<211> LENGTH: 229
<212> TYPE: DNA
<213> ORGANISM: Artificial Sequence
<220> FEATURE:
<223> OTHER INFORMATION: 229 bp DNA fragment derived from genomic DNA of
      E. coli (ref. seq ID U00096.3). Located 60 bp upstream of the glpT
      translation initiation codon

<400> SEQUENCE: 4
ccatttagcc atagtaaaaa catgaattgt ttgatttcgc gcatattcgc tcataattcg      60
aaagtgaaac gtgatttcat gcgtcatttt gaacattttg taaatcttat ttaataatgt     120
gtgcggcaat tcacatttaa tttatgaatg ttttcttaac atcgcggcaa ctcaagaaac     180
ggcaggttct ctcactgaat caggctgtta atcataaata agaccacgg                 229

<210> SEQ ID NO 5
<211> LENGTH: 16
<212> TYPE: DNA
<213> ORGANISM: Artificial Sequence
<220> FEATURE:
<223> OTHER INFORMATION: 16-nucleotide DNA fragment derived from genomic
      DNA of E. coli (ref. seq ID U00096.3) located directly upstream
      the translational initiation codon of glpF

<400> SEQUENCE: 5
tcttcaggat ccgatt                                                      16

<210> SEQ ID NO 6
<211> LENGTH: 16
<212> TYPE: DNA
<213> ORGANISM: Artificial Sequence
<220> FEATURE:
<223> OTHER INFORMATION: 16-nucleotide DNA fragment derived from genomic
      DNA of E. coli (ref. seq ID U00096.3) located directly upstream
      the translational initiation codon of glpA

<400> SEQUENCE: 6
cttcagaggg ataaca                                                      16

<210> SEQ ID NO 7
<211> LENGTH: 16
<212> TYPE: DNA
<213> ORGANISM: Artificial Sequence
<220> FEATURE:
<223> OTHER INFORMATION: 16-nucleotide DNA fragment derived from genomic
      DNA of E. coli (ref. seq ID U00096.3) located upstream the
      translational initiation codon of glpD

<400> SEQUENCE: 7
agtgaatgag ggcagc                                                      16

<210> SEQ ID NO 8
<211> LENGTH: 16
<212> TYPE: DNA
<213> ORGANISM: Artificial Sequence
<220> FEATURE:
<223> OTHER INFORMATION: 16 -nucleotide DNA fragment derived from
      genomic DNA of E. coli (ref. seq ID U00096.3) located directly
      upstream the translational initiation codon of glpT

<400> SEQUENCE: 8
gccacggagg ctatca                                                      16

<210> SEQ ID NO 9
<211> LENGTH: 16
<212> TYPE: DNA
```

```
<213> ORGANISM: Artificial Sequence
<220> FEATURE:
<223> OTHER INFORMATION: 16-nucleotide DNA fragment derived from genomic
      DNA of E. coli (ref. seq ID U00096.3). located upstream of lacZ

<400> SEQUENCE: 9
cacacaggaa acagct                                                         16

<210> SEQ ID NO 10
<211> LENGTH: 16
<212> TYPE: DNA
<213> ORGANISM: Artificial Sequence
<220> FEATURE:
<223> OTHER INFORMATION: Variant of SEQ ID NO: 9 ) (CAC -> AGG )

<400> SEQUENCE: 10
caaggaggaa acagct                                                         16

<210> SEQ ID NO 11
<211> LENGTH: 107
<212> TYPE: DNA
<213> ORGANISM: Artificial Sequence
<220> FEATURE:
<223> OTHER INFORMATION: 107-nucleotide DNA fragment located upstream of
      lacZ derived from genomic DNA of E. coli (ref. seq ID U00096.3);
      lac operon promoter element

<400> SEQUENCE: 11
tgtgagttag ctcactcatt aggcacccca ggctttacac tttatgcttc cggctcgtat         60
gttgtgtgga attgtgagcg ataacaatt tcacacagga aacagct                       107

<210> SEQ ID NO 12
<211> LENGTH: 300
<212> TYPE: DNA
<213> ORGANISM: Artificial Sequence
<220> FEATURE:
<223> OTHER INFORMATION: 300 -nucleotide DNA fragment comprising SEQ ID
      NO: 1 and SEQ ID NO: 10

<400> SEQUENCE: 12
gcggcacgcc ttgcagatta cggtttgcca cactttcat ccttctcctg gtgacataat         60
ccacatcaat cgaaaatgtt aataaatttg ttgcgcgaat gatctaacaa acatgcatca       120
tgtacaatca gatggaataa atggcgcgat aacgctcatt ttatgacgag gcacacacat       180
tttaagttcg atatttctcg ttttgctcg ttaacgataa gtttacagca tgcctacaag        240
catcgtggag gtccgtgact ttcacgcata caacaaacat taaccaagga ggaaacagct       300

<210> SEQ ID NO 13
<211> LENGTH: 300
<212> TYPE: DNA
<213> ORGANISM: Artificial Sequence
<220> FEATURE:
<223> OTHER INFORMATION: 300-nucleotide DNA fragment comprising SEQ ID
      NO: 1 and SEQ ID NO: 38

<400> SEQUENCE: 13
gcggcacgcc ttgcagatta cggtttgcca cactttcat ccttctcctg gtgacataat         60
ccacatcaat cgaaaatgtt aataaatttg ttgcgcgaat gatctaacaa acatgcatca       120
tgtacaatca gatggaataa atggcgcgat aacgctcatt ttatgacgag gcacacacat       180
tttaagttcg atatttctcg ttttgctcg ttaacgataa gtttacagca tgcctacaag        240
catcgtggag gtccgtgact ttcacgcata caacaaacat taaccaaatt cgaaacagct       300
```

<210> SEQ ID NO 14
<211> LENGTH: 300
<212> TYPE: DNA
<213> ORGANISM: Artificial Sequence
<220> FEATURE:
<223> OTHER INFORMATION: 300-nucleotide DNA fragment comprising SEQ ID
      NO: 1 and SEQ ID NO: 39

<400> SEQUENCE: 14
gcggcacgcc ttgcagatta cggtttgcca cactttcat ccttctcctg gtgacataat       60
ccacatcaat cgaaaatgtt aataaatttg ttgcgcgaat gatctaacaa acatgcatca      120
tgtacaatca gatggaataa atggcgcgat aacgctcatt ttatgacgag gcacacacat     180
tttaagttcg atatttctcg tttttgctcg ttaacgataa gtttacagca tgcctacaag     240
catcgtggag gtccgtgact ttcacgcata caacaaacat taaccaagcg caaaacagct    300

<210> SEQ ID NO 15
<211> LENGTH: 300
<212> TYPE: DNA
<213> ORGANISM: Artificial Sequence
<220> FEATURE:
<223> OTHER INFORMATION: 300 -nucleotide DNA fragment comprising SEQ ID
      NO: 1 and SEQ ID NO:40

<400> SEQUENCE: 15
gcggcacgcc ttgcagatta cggtttgcca cactttcat ccttctcctg gtgacataat       60
ccacatcaat cgaaaatgtt aataaatttg ttgcgcgaat gatctaacaa acatgcatca      120
tgtacaatca gatggaataa atggcgcgat aacgctcatt ttatgacgag gcacacacat     180
tttaagttcg atatttctcg tttttgctcg ttaacgataa gtttacagca tgcctacaag     240
catcgtggag gtccgtgact ttcacgcata caacaaacat taaccaagaa caaaacagct    300

<210> SEQ ID NO 16
<211> LENGTH: 300
<212> TYPE: DNA
<213> ORGANISM: Artificial Sequence
<220> FEATURE:
<223> OTHER INFORMATION: 300-nucleotide DNA fragment comprising SEQ ID
      NO: 1 and SEQ ID NO:41

<400> SEQUENCE: 16
gcggcacgcc ttgcagatta cggtttgcca cactttcat ccttctcctg gtgacataat       60
ccacatcaat cgaaaatgtt aataaatttg ttgcgcgaat gatctaacaa acatgcatca      120
tgtacaatca gatggaataa atggcgcgat aacgctcatt ttatgacgag gcacacacat     180
tttaagttcg atatttctcg tttttgctcg ttaacgataa gtttacagca tgcctacaag     240
catcgtggag gtccgtgact ttcacgcata caacaaacat taaccaacta ggaaacagct    300

<210> SEQ ID NO 17
<211> LENGTH: 300
<212> TYPE: DNA
<213> ORGANISM: Artificial Sequence
<220> FEATURE:
<223> OTHER INFORMATION: 300-nucleotide DNA fragment comprising SEQ ID
      NO: 1 and SEQ ID NO:42

<400> SEQUENCE: 17
gcggcacgcc ttgcagatta cggtttgcca cactttcat ccttctcctg gtgacataat       60
ccacatcaat cgaaaatgtt aataaatttg ttgcgcgaat gatctaacaa acatgcatca      120
tgtacaatca gatggaataa atggcgcgat aacgctcatt ttatgacgag gcacacacat     180

```
tttaagttcg atatttctcg tttttgctcg ttaacgataa gtttacagca tgcctacaag    240
catcgtggag gtccgtgact ttcacgcata caacaaacat taaccaaccg agaaacagct   300
```

<210> SEQ ID NO 18
<211> LENGTH: 300
<212> TYPE: DNA
<213> ORGANISM: Artificial Sequence
<220> FEATURE:
<223> OTHER INFORMATION: 300-nucleotide DNA fragment comprising SEQ ID
      NO: 1 and SEQ ID NO:43

<400> SEQUENCE: 18

```
gcggcacgcc ttgcagatta cggtttgcca cacttttcat ccttctcctg gtgacataat    60
ccacatcaat cgaaaatgtt aataaatttg ttgcgcgaat gatctaacaa acatgcatca   120
tgtacaatca gatggaataa atggcgcgat aacgctcatt ttatgacgag gcacacacat   180
tttaagttcg atatttctcg tttttgctcg ttaacgataa gtttacagca tgcctacaag   240
catcgtggag gtccgtgact ttcacgcata caacaaacat taaccaagag ctaaacagct   300
```

<210> SEQ ID NO 19
<211> LENGTH: 300
<212> TYPE: DNA
<213> ORGANISM: Artificial Sequence
<220> FEATURE:
<223> OTHER INFORMATION: 300-nucleotide DNA fragment comprising SEQ ID
      NO: 1 and SEQ ID NO:44

<400> SEQUENCE: 19

```
gcggcacgcc ttgcagatta cggtttgcca cacttttcat ccttctcctg gtgacataat    60
ccacatcaat cgaaaatgtt aataaatttg ttgcgcgaat gatctaacaa acatgcatca   120
tgtacaatca gatggaataa atggcgcgat aacgctcatt ttatgacgag gcacacacat   180
tttaagttcg atatttctcg tttttgctcg ttaacgataa gtttacagca tgcctacaag   240
catcgtggag gtccgtgact ttcacgcata caacaaacat taaccaagag caaaacagct   300
```

<210> SEQ ID NO 20
<211> LENGTH: 300
<212> TYPE: DNA
<213> ORGANISM: Artificial Sequence
<220> FEATURE:
<223> OTHER INFORMATION: 300-nucleotide DNA fragment comprising SEQ ID
      NO: 1 and SEQ ID NO:45

<400> SEQUENCE: 20

```
gcggcacgcc ttgcagatta cggtttgcca cacttttcat ccttctcctg gtgacataat    60
ccacatcaat cgaaaatgtt aataaatttg ttgcgcgaat gatctaacaa acatgcatca   120
tgtacaatca gatggaataa atggcgcgat aacgctcatt ttatgacgag gcacacacat   180
tttaagttcg atatttctcg tttttgctcg ttaacgataa gtttacagca tgcctacaag   240
catcgtggag gtccgtgact ttcacgcata caacaaacat taaccaagag aaaaacagct   300
```

<210> SEQ ID NO 21
<211> LENGTH: 300
<212> TYPE: DNA
<213> ORGANISM: Artificial Sequence
<220> FEATURE:
<223> OTHER INFORMATION: 300-nucleotide DNA fragment comprising SEQ ID
      NO: 1 and SEQ ID NO:46

<400> SEQUENCE: 21

```
gcggcacgcc ttgcagatta cggtttgcca cacttttcat ccttctcctg gtgacataat    60
ccacatcaat cgaaaatgtt aataaatttg ttgcgcgaat gatctaacaa acatgcatca   120
tgtacaatca gatggaataa atggcgcgat aacgctcatt ttatgacgag gcacacacat   180
tttaagttcg atatttctcg ttttttgctcg ttaacgataa gtttacagca tgcctacaag   240
catcgtggag gtccgtgact ttcacgcata caacaaacat taaccaaagg aaaaacagct   300
```

<210> SEQ ID NO 22
<211> LENGTH: 300
<212> TYPE: DNA
<213> ORGANISM: Artificial Sequence
<220> FEATURE:
<223> OTHER INFORMATION: 300-nucleotide DNA fragment comprising SEQ ID
      NO: 1 and SEQ ID NO: 47

<400> SEQUENCE: 22

```
gcggcacgcc ttgcagatta cggtttgcca cacttttcat ccttctcctg gtgacataat    60
ccacatcaat cgaaaatgtt aataaatttg ttgcgcgaat gatctaacaa acatgcatca   120
tgtacaatca gatggaataa atggcgcgat aacgctcatt ttatgacgag gcacacacat   180
tttaagttcg atatttctcg ttttttgctcg ttaacgataa gtttacagca tgcctacaag   240
catcgtggag gtccgtgact ttcacgcata caacaaacat taaccaactg agaaacagct   300
```

<210> SEQ ID NO 23
<211> LENGTH: 300
<212> TYPE: DNA
<213> ORGANISM: Artificial Sequence
<220> FEATURE:
<223> OTHER INFORMATION: Variant of SEQ ID NO:12 comprising a
      modification of the -10 region (See Figure 7)

<400> SEQUENCE: 23

```
gcggcacgcc ttgcagatta cggtttgcca cacttttcat ccttctcctg gtgacataat    60
ccacatcaat cgaaaatgtt aataaatttg ttgcgcgaat gatctaacaa acatgcatca   120
tgtacaatca gatggaataa atggcgcgat aacgctcatt ttatgacgag gcacacacat   180
tttaagttcg atatttctcg ttttttgctcg ttaacgattt aattacagca tgcctacaag   240
catcgtggag gtccgtgact ttcacgcata caacaaacat taaccaagga ggaaacagct   300
```

<210> SEQ ID NO 24
<211> LENGTH: 300
<212> TYPE: DNA
<213> ORGANISM: Artificial Sequence
<220> FEATURE:
<223> OTHER INFORMATION: Variant of SEQ ID NO:12 comprising a
      modification of the -10 region

<400> SEQUENCE: 24

```
gcggcacgcc ttgcagatta cggtttgcca cacttttcat ccttctcctg gtgacataat    60
ccacatcaat cgaaaatgtt aataaatttg ttgcgcgaat gatctaacaa acatgcatca   120
tgtacaatca gatggaataa atggcgcgat aacgctcatt ttatgacgag gcacacacat   180
tttaagttcg atatttctcg ttttttgctcg ttaacgatca gaatacagca tgcctacaag   240
catcgtggag gtccgtgact ttcacgcata caacaaacat taaccaagga ggaaacagct   300
```

<210> SEQ ID NO 25
<211> LENGTH: 300
<212> TYPE: DNA
<213> ORGANISM: Artificial Sequence
<220> FEATURE:

<223> OTHER INFORMATION: Variant of SEQ ID NO:12 comprising a
       modification of the -10 region

<400> SEQUENCE: 25
gcggcacgcc ttgcagatta cggtttgcca cacttttcat ccttctcctg gtgacataat    60
ccacatcaat cgaaaatgtt aataaatttg ttgcgcgaat gatctaacaa acatgcatca   120
tgtacaatca gatggaataa atggcgcgat aacgctcatt ttatgacgag gcacacacat   180
tttaagttcg atatttctcg ttttttgctcg ttaacgatat tcctacagca tgcctacaag   240
catcgtggag gtccgtgact ttcacgcata caacaaacat taaccaagga ggaaacagct   300

<210> SEQ ID NO 26
<211> LENGTH: 300
<212> TYPE: DNA
<213> ORGANISM: Artificial Sequence
<220> FEATURE:
<223> OTHER INFORMATION: Variant of SEQ ID NO:12 comprising a
       modification of the -10 region

<400> SEQUENCE: 26
gcggcacgcc ttgcagatta cggtttgcca cacttttcat ccttctcctg gtgacataat    60
ccacatcaat cgaaaatgtt aataaatttg ttgcgcgaat gatctaacaa acatgcatca   120
tgtacaatca gatggaataa atggcgcgat aacgctcatt ttatgacgag gcacacacat   180
tttaagttcg atatttctcg ttttttgctcg ttaacgataa tgatacagca tgcctacaag   240
catcgtggag gtccgtgact ttcacgcata caacaaacat taaccaagga ggaaacagct   300

<210> SEQ ID NO 27
<211> LENGTH: 300
<212> TYPE: DNA
<213> ORGANISM: Artificial Sequence
<220> FEATURE:
<223> OTHER INFORMATION: Variant of SEQ ID NO:12 comprising a
       modification of the -10 region

<400> SEQUENCE: 27
gcggcacgcc ttgcagatta cggtttgcca cacttttcat ccttctcctg gtgacataat    60
ccacatcaat cgaaaatgtt aataaatttg ttgcgcgaat gatctaacaa acatgcatca   120
tgtacaatca gatggaataa atggcgcgat aacgctcatt ttatgacgag gcacacacat   180
tttaagttcg atatttctcg ttttttgctcg ttaacgatga agctacagca tgcctacaag   240
catcgtggag gtccgtgact ttcacgcata caacaaacat taaccaagga ggaaacagct   300

<210> SEQ ID NO 28
<211> LENGTH: 300
<212> TYPE: DNA
<213> ORGANISM: Artificial Sequence
<220> FEATURE:
<223> OTHER INFORMATION: Variant of SEQ ID NO:12 comprising a
       modification of the -10 region

<400> SEQUENCE: 28
gcggcacgcc ttgcagatta cggtttgcca cacttttcat ccttctcctg gtgacataat    60
ccacatcaat cgaaaatgtt aataaatttg ttgcgcgaat gatctaacaa acatgcatca   120
tgtacaatca gatggaataa atggcgcgat aacgctcatt ttatgacgag gcacacacat   180
tttaagttcg atatttctcg ttttttgctcg ttaacgatca gtatacagca tgcctacaag   240
catcgtggag gtccgtgact ttcacgcata caacaaacat taaccaagga ggaaacagct   300

```
<210> SEQ ID NO 29
<211> LENGTH: 285
<212> TYPE: DNA
<213> ORGANISM: Artificial Sequence
<220> FEATURE:
<223> OTHER INFORMATION: 285-nucleotide DNA fragment of SEQ ID NO: 12

<400> SEQUENCE: 29
gattacggtt tgccacactt ttcatccttc tcctggtgac ataatccaca tcaatcgaaa      60
atgttaataa atttgttgcg cgaatgatct aacaaacatg catcatgtac aatcagatgg     120
aataaatggc gcgataacgc tcattttatg acgaggcaca cacattttaa gttcgatatt     180
tctcgttttt gctcgttaac gataagttta cagcatgcct acaagcatcg tggaggtccg     240
tgactttcac gcatacaaca aacattaacc aaggaggaaa cagct                    285

<210> SEQ ID NO 30
<211> LENGTH: 160
<212> TYPE: DNA
<213> ORGANISM: Artificial Sequence
<220> FEATURE:
<223> OTHER INFORMATION: 160-nucleotide DNA fragment of SEQ ID NO: 12

<400> SEQUENCE: 30
atggcgcgat aacgctcatt ttatgacgag gcacacacat tttaagttcg atatttctcg      60 ttttgctcg ttaacgataa gtttacagca tgcctacaag catcgtggag gtccgtgact     120
ttcacgcata caacaaacat taaccaagga ggaaacagct                          160

<210> SEQ ID NO 31
<211> LENGTH: 135
<212> TYPE: DNA
<213> ORGANISM: Artificial Sequence
<220> FEATURE:
<223> OTHER INFORMATION: 135-nucleotide DNA fragment of SEQ ID NO: 12

<400> SEQUENCE: 31
acgaggcaca cacattttaa gttcgatatt tctcgttttt gctcgttaac gataagttta      60
cagcatgcct acaagcatcg tggaggtccg tgactttcac gcatacaaca aacattaacc     120
aaggaggaaa cagct                                                     135

<210> SEQ ID NO 32
<211> LENGTH: 120
<212> TYPE: DNA
<213> ORGANISM: Artificial Sequence
<220> FEATURE:
<223> OTHER INFORMATION: 120-nucleotide DNA fragment of SEQ ID NO: 12

<400> SEQUENCE: 32
tttaagttcg atatttctcg tttttgctcg ttaacgataa gtttacagca tgcctacaag      60
catcgtggag gtccgtgact ttcacgcata caacaaacat taaccaagga ggaaacagct     120

<210> SEQ ID NO 33
<211> LENGTH: 182
<212> TYPE: DNA
<213> ORGANISM: Artificial Sequence
<220> FEATURE:
<223> OTHER INFORMATION: 182-nucleotide DNA fragment comprising SEQ ID
      NO: 2 and SEQ ID NO: 10

<400> SEQUENCE: 33 gaaacattc ataaattaaa tgtgaattgc cgcacacatt attaaataag atttacaaaa       60
tgttcaaaat gacgcatgaa atcacgtttc actttcgaat tatgagcgaa tatgcgcgaa    120
```

```
atcaaacaat tcatgttttt actatggcta aatggtaaaa aacgaacaag gaggaaacag    180
ct                                                                  182
```

<210> SEQ ID NO 34
<211> LENGTH: 190
<212> TYPE: DNA
<213> ORGANISM: Artificial Sequence
<220> FEATURE:
<223> OTHER INFORMATION: 190-nucleotide DNA fragment comprising SEQ ID
      NO: 3 and SEQ ID NO: 10

<400> SEQUENCE: 34

```
tgcgtctctc tttctttaca aacaagtggg caaatttacc gcacagttta cgtcgaagcg     60
gcagataaac gccataatgt tatacatatc actctaaaat gttttttcaa tgttacctaa    120
agcgcgattc tttgctaata tgttcgataa cgaacattta tgagctttaa cgaacaagga    180
ggaaacagct                                                          190
```

<210> SEQ ID NO 35
<211> LENGTH: 245
<212> TYPE: DNA
<213> ORGANISM: Artificial Sequence
<220> FEATURE:
<223> OTHER INFORMATION: 245-nucleotide DNA fragment comprising SEQ ID
      NO: 4 and SEQ ID NO: 10

<400> SEQUENCE: 35

```
ccatttagcc atagtaaaaa catgaattgt ttgatttcgc gcatattcgc tcataattcg     60
aaagtgaaac gtgatttcat gcgtcatttt gaacattttg taaatcttat ttaataatgt    120
gtgcggcaat tcacatttaa tttatgaatg ttttcttaac atcgcggcaa ctcaagaaac    180
ggcaggttct ctcactgaat caggctgtta atcataaata agaccacggc aaggaggaaa    240
cagct                                                               245
```

<210> SEQ ID NO 36
<211> LENGTH: 54
<212> TYPE: DNA
<213> ORGANISM: Artificial Sequence
<220> FEATURE:
<223> OTHER INFORMATION: 54-nucleotide DNA fragment of the 5'UTR- glpF
      located downstream of the transcription initiation site and 16
      nucleotides upstream the translation initiation codon

<400> SEQUENCE: 36

```
tgcctacaag catcgtggag gtccgtgact ttcacgcata caacaaacat taac             54
```

<210> SEQ ID NO 37
<211> LENGTH: 70
<212> TYPE: DNA
<213> ORGANISM: Artificial Sequence
<220> FEATURE:
<223> OTHER INFORMATION: 70-nucleotide synthetic non-coding DNA sequence
      (ii) comprising SEQ ID NO: 36 and SEQ ID NO: 10

<400> SEQUENCE: 37

```
tgcctacaag catcgtggag gtccgtgact ttcacgcata caacaaacat taaccaagga     60
ggaaacagct                                                          70
```

<210> SEQ ID NO 38
<211> LENGTH: 16
<212> TYPE: DNA
<213> ORGANISM: Artificial Sequence

```
<220> FEATURE:
<223> OTHER INFORMATION: Variant of SEQ ID NO: 10

<400> SEQUENCE: 38
caaattcgaa acagct                                                      16

<210> SEQ ID NO 39
<211> LENGTH: 16
<212> TYPE: DNA
<213> ORGANISM: Artificial Sequence
<220> FEATURE:
<223> OTHER INFORMATION: Variant of SEQ ID NO: 10

<400> SEQUENCE: 39
caagcgcaaa acagct                                                      16

<210> SEQ ID NO 40
<211> LENGTH: 16
<212> TYPE: DNA
<213> ORGANISM: Artificial Sequence
<220> FEATURE:
<223> OTHER INFORMATION: Variant of SEQ ID NO: 10

<400> SEQUENCE: 40
caagaacaaa acagct                                                      16

<210> SEQ ID NO 41
<211> LENGTH: 16
<212> TYPE: DNA
<213> ORGANISM: Artificial Sequence
<220> FEATURE:
<223> OTHER INFORMATION: Variant of SEQ ID NO: 10

<400> SEQUENCE: 41
caactaggaa acagct                                                      16

<210> SEQ ID NO 42
<211> LENGTH: 16
<212> TYPE: DNA
<213> ORGANISM: Artificial Sequence
<220> FEATURE:
<223> OTHER INFORMATION: Variant of SEQ ID NO: 10

<400> SEQUENCE: 42
caaccgagaa acagct                                                      16

<210> SEQ ID NO 43
<211> LENGTH: 16
<212> TYPE: DNA
<213> ORGANISM: Artificial Sequence
<220> FEATURE:
<223> OTHER INFORMATION: Variant of SEQ ID NO: 10

<400> SEQUENCE: 43
caagagctaa acagct                                                      16

<210> SEQ ID NO 44
<211> LENGTH: 16
<212> TYPE: DNA
<213> ORGANISM: Artificial Sequence
<220> FEATURE:
<223> OTHER INFORMATION: Variant of SEQ ID NO: 10

<400> SEQUENCE: 44
caagagcaaa acagct                                                      16
```

<210> SEQ ID NO 45
<211> LENGTH: 16
<212> TYPE: DNA
<213> ORGANISM: Artificial Sequence
<220> FEATURE:
<223> OTHER INFORMATION: Variant of SEQ ID NO: 10

<400> SEQUENCE: 45
caagagaaaa acagct                                                   16

<210> SEQ ID NO 46
<211> LENGTH: 16
<212> TYPE: DNA
<213> ORGANISM: Artificial Sequence
<220> FEATURE:
<223> OTHER INFORMATION: Variant of SEQ ID NO: 10

<400> SEQUENCE: 46
caaaggaaaa acagct                                                   16

<210> SEQ ID NO 47
<211> LENGTH: 16
<212> TYPE: DNA
<213> ORGANISM: Artificial Sequence
<220> FEATURE:
<223> OTHER INFORMATION: Variant of SEQ ID NO: 10

<400> SEQUENCE: 47
caactgagaa acagct                                                   16

<210> SEQ ID NO 48
<211> LENGTH: 119
<212> TYPE: DNA
<213> ORGANISM: Artificial Sequence
<220> FEATURE:
<223> OTHER INFORMATION: 119-nucleotide DNA fragment derived from
      genomic DNA of E. coli (ref. seq ID U00096.3) located upstream of
      the glpA transcription initiation start; glpA promoter element

<400> SEQUENCE: 48
gaaaacattc ataaattaaa tgtgaattgc cgcacacatt attaaataag atttacaaaa    60
tgttcaaaat gacgcatgaa atcacgtttc actttcgaat tatgagcgaa tatgcgcga    119

<210> SEQ ID NO 49
<211> LENGTH: 169
<212> TYPE: DNA
<213> ORGANISM: Artificial Sequence
<220> FEATURE:
<223> OTHER INFORMATION: 169-nucleotide DNA fragment derived from
      genomic DNA of E. coli (ref. seq ID U00096.3) located upstream of
      the glpT transcription initiation start; glpT promoter element

<400> SEQUENCE: 49
ccatttagcc atagtaaaaa catgaattgt tgatttcgc gcatattcgc tcataattcg     60
aaagtgaaac gtgatttcat gcgtcatttt gaacattttg taaatcttat ttaataatgt   120
gtgcggcaat tcacatttaa tttatgaatg ttttcttaac atcgcggca              169

<210> SEQ ID NO 50
<211> LENGTH: 189
<212> TYPE: DNA
<213> ORGANISM: Artificial Sequence
<220> FEATURE:
<223> OTHER INFORMATION: 189-nucleotide DNA fragment obtained by
      combining SEQ ID NO: 49 with SEQ ID NO 37

<400> SEQUENCE: 50
gaaaacattc ataaattaaa tgtgaattgc cgcacacatt attaaataag atttacaaaa    60
tgttcaaaat gacgcatgaa atcacgtttc actttcgaat tatgagcgaa tatgcgcgat   120
gcctacaagc atcgtggagg tccgtgactt tcacgcatac aacaaacatt aaccaaggag   180
gaaacagct                                                           189

<210> SEQ ID NO 51
<211> LENGTH: 239
<212> TYPE: DNA
<213> ORGANISM: Artificial Sequence
<220> FEATURE:
<223> OTHER INFORMATION: 239-nucleotide DNA fragment obtained by
      combining SEQ ID NO: 50 with synthetic non-coding DNA sequence
      (ii) (SEQ ID NO 37)

<400> SEQUENCE: 51
ccatttagcc atagtaaaaa catgaattgt ttgatttcgc gcatattcgc tcataattcg    60
aaagtgaaac gtgatttcat gcgtcatttt gaacattttg taaatcttat ttaataatgt   120
gtgcggcaat tcacatttaa tttatgaatg ttttcttaac atcgcggcat gcctacaagc   180
atcgtggagg tccgtgactt tcacgcatac aacaaacatt aaccaaggag gaaacagct   239

<210> SEQ ID NO 52
<211> LENGTH: 239
<212> TYPE: DNA
<213> ORGANISM: Artificial Sequence
<220> FEATURE:
<223> OTHER INFORMATION: 239-nucleotide DNA fragment SEQ ID NO: 50 where
      the 16 bp located upstream of the translation initiation site is
      identical to SEQ ID NO 41

<400> SEQUENCE: 52
ccatttagcc atagtaaaaa catgaattgt ttgatttcgc gcatattcgc tcataattcg    60
aaagtgaaac gtgatttcat gcgtcatttt gaacattttg taaatcttat ttaataatgt   120
gtgcggcaat tcacatttaa tttatgaatg ttttcttaac atcgcggcat gcctacaagc   180
atcgtggagg tccgtgactt tcacgcatac aacaaacatt aaccaactag gaaacagct   239

<210> SEQ ID NO 53
<211> LENGTH: 239
<212> TYPE: DNA
<213> ORGANISM: Artificial Sequence
<220> FEATURE:
<223> OTHER INFORMATION: 239-nucleotide DNA fragment SEQ ID NO: 50 where
      the 16 bp located upstream of the translation initiation site is
      identical to SEQ ID NO 46

<400> SEQUENCE: 53
ccatttagcc atagtaaaaa catgaattgt ttgatttcgc gcatattcgc tcataattcg    60
aaagtgaaac gtgatttcat gcgtcatttt gaacattttg taaatcttat ttaataatgt   120
gtgcggcaat tcacatttaa tttatgaatg ttttcttaac atcgcggcat gcctacaagc   180
atcgtggagg tccgtgactt tcacgcatac aacaaacatt aaccaaagga aaaacagct   239

<210> SEQ ID NO 54
<211> LENGTH: 230
<212> TYPE: DNA
<213> ORGANISM: Artificial Sequence
<220> FEATURE:
<223> OTHER INFORMATION: 230-nucleotide DNA sequence derived from
      genomic DNA of E. coli (ref. seq ID U00096.3) located upstream the
      initiation of transcription of glpF; glpF promoter element

<400> SEQUENCE: 54

```
gcggcacgcc ttgcagatta cggtttgcca cactttcat ccttctcctg gtgacataat      60
ccacatcaat cgaaaatgtt aataaatttg ttgcgcgaat gatctaacaa acatgcatca     120
tgtacaatca gatggaataa atggcgcgat aacgctcatt ttatgacgag gcacacacat    180
tttaagttcg atatttctcg tttttgctcg ttaacgataa gtttacagca                230
```

<210> SEQ ID NO 55
<211> LENGTH: 245
<212> TYPE: DNA
<213> ORGANISM: Artificial Sequence
<220> FEATURE:
<223> OTHER INFORMATION: 245-nucleotide nucleotide DNA sequence derived
      from genomic DNA of E. coli (ref. seq ID U00096.3) located
      upstream the initiation of translation of glpT

<400> SEQUENCE: 55

```
ccatttagcc atagtaaaaa catgaattgt ttgatttcgc gcatattcgc tcataattcg      60
aaagtgaaac gtgatttcat gcgtcatttt gaacattttg taaatcttat ttaataatgt    120
gtgcggcaat tcacatttaa tttatgaatg ttttcttaac atcgcggcaa ctcaagaaac    180
ggcaggttct ctcactgaat caggctgtta atcataaata gaccacggg ccacggaggc    240 tatca                                                                 245
```

<210> SEQ ID NO 56
<211> LENGTH: 182
<212> TYPE: DNA
<213> ORGANISM: Artificial Sequence
<220> FEATURE:
<223> OTHER INFORMATION: 182-nucleotide DNA sequence derived from
      genomic DNA of E. coli (ref. seq ID U00096.3) located upstream the
      initiation of translation of glpA

<400> SEQUENCE: 56

```
gaaaacattc ataaattaaa tgtgaattgc cgcacacatt attaaataag atttacaaaa      60
tgttcaaaat gacgcatgaa atcacgtttc actttcgaat tatgagcgaa tatgcgcgaa    120
atcaaacaat tcatgttttt actatggcta aatggtaaaa aacgaacttc agagggataa    180
ca                                                                    182
```

<210> SEQ ID NO 57
<211> LENGTH: 300
<212> TYPE: DNA
<213> ORGANISM: Artificial Sequence
<220> FEATURE:
<223> OTHER INFORMATION: 300-nucleotide DNA sequence derived from
      genomic DNA of E. coli (ref. seq ID U00096.3) located upstream the
      initiation of translation of glpF

<400> SEQUENCE: 57

```
gcggcacgcc ttgcagatta cggtttgcca cactttcat ccttctcctg gtgacataat      60
ccacatcaat cgaaaatgtt aataaatttg ttgcgcgaat gatctaacaa acatgcatca    120
tgtacaatca gatggaataa atggcgcgat aacgctcatt ttatgacgag gcacacacat    180
tttaagttcg atatttctcg tttttgctcg ttaacgataa gtttacagca tgcctacaag    240
catcgtggag gtccgtgact ttcacgcata caacaaacat taactcttca ggatccgatt    300
```

<210> SEQ ID NO 58
<211> LENGTH: 24
<212> TYPE: DNA

```
<213> ORGANISM: Artificial Sequence
<220> FEATURE:
<223> OTHER INFORMATION: combined DNA/RNA artificial sequence - primer

<400> SEQUENCE: 58
cccagcgaga cctgaccgca gaac                                          24

<210> SEQ ID NO 59
<211> LENGTH: 24
<212> TYPE: DNA
<213> ORGANISM: Artificial Sequence
<220> FEATURE:
<223> OTHER INFORMATION: Combined DNA/RNA artificial sequence - primer

<400> SEQUENCE: 59
ccccagtcca tcagcgtgac tacc                                          24

<210> SEQ ID NO 60
<211> LENGTH: 34
<212> TYPE: DNA
<213> ORGANISM: Artificial Sequence
<220> FEATURE:
<223> OTHER INFORMATION: Combined DNA/RNA artificial sequence - primer

<400> SEQUENCE: 60
atgcgcaaau cggatctcaa ggaaatcgca atgg                               34

<210> SEQ ID NO 61
<211> LENGTH: 38
<212> TYPE: DNA
<213> ORGANISM: Artificial Sequence
<220> FEATURE:
<223> OTHER INFORMATION: Combined DNA/RNA artificial sequence - primer

<400> SEQUENCE: 61
agctgttucc tccttgctca ttgtcatagt gcggcagg                           38

<210> SEQ ID NO 62
<211> LENGTH: 32
<212> TYPE: DNA
<213> ORGANISM: Artificial Sequence
<220> FEATURE:
<223> OTHER INFORMATION: Combined DNA/RNA artificial sequence - primer

<400> SEQUENCE: 62
atgcgcaaau gctgaatccg aacaccagcg tc                                 32

<210> SEQ ID NO 63
<211> LENGTH: 39
<212> TYPE: DNA
<213> ORGANISM: Artificial Sequence
<220> FEATURE:
<223> OTHER INFORMATION: Combined DNA/RNA artificial sequence - primer

<400> SEQUENCE: 63
agctgttucc tccttggcag gacttcatta ttaagacgg                          39

<210> SEQ ID NO 64
<211> LENGTH: 35
<212> TYPE: DNA
<213> ORGANISM: Artificial Sequence
<220> FEATURE:
<223> OTHER INFORMATION: Combined DNA/RNA artificial sequence - primer

<400> SEQUENCE: 64
atgcgcaaau tactcactac tgaaacaata ttgcc                              35
```

<210> SEQ ID NO 65
<211> LENGTH: 44
<212> TYPE: DNA
<213> ORGANISM: Artificial Sequence
<220> FEATURE:
<223> OTHER INFORMATION: Combined DNA/RNA artificial sequence - primer

<400> SEQUENCE: 65
agctgttucc tccttgtaat cctatttaaa tttttgctga atag                      44

<210> SEQ ID NO 66
<211> LENGTH: 31
<212> TYPE: DNA
<213> ORGANISM: Artificial Sequence
<220> FEATURE:
<223> OTHER INFORMATION: Combined DNA/RNA artificial sequence - primer

<400> SEQUENCE: 66
atgcgcaaau ccgaaaattc ctggcgagca g                                    31

<210> SEQ ID NO 67
<211> LENGTH: 39
<212> TYPE: DNA
<213> ORGANISM: Artificial Sequence
<220> FEATURE:
<223> OTHER INFORMATION: Combined DNA/RNA artificial sequence - primer

<400> SEQUENCE: 67
agctgttucc tccttggatg ttatgtccca gtaattaac                            39

<210> SEQ ID NO 68
<211> LENGTH: 36
<212> TYPE: DNA
<213> ORGANISM: Artificial Sequence
<220> FEATURE:
<223> OTHER INFORMATION: Combined DNA/RNA artificial sequence - primer

<400> SEQUENCE: 68
atgcgcaaau gaagtaatct ttcttcacct gcgttc                               36

<210> SEQ ID NO 69
<211> LENGTH: 44
<212> TYPE: DNA
<213> ORGANISM: Artificial Sequence
<220> FEATURE:
<223> OTHER INFORMATION: Combined DNA/RNA artificial sequence - primer

<400> SEQUENCE: 69
agctgttucc tccttggtta tttttttattg tgaattaaga tagg                     44

<210> SEQ ID NO 70
<211> LENGTH: 30
<212> TYPE: DNA
<213> ORGANISM: Artificial Sequence
<220> FEATURE:
<223> OTHER INFORMATION: Combined DNA/RNA artificial sequence - primer

<400> SEQUENCE: 70
atgcgcaaau cagttcttct gccgaaggtt                                      30

<210> SEQ ID NO 71
<211> LENGTH: 39
<212> TYPE: DNA
<213> ORGANISM: Artificial Sequence
<220> FEATURE:

<223> OTHER INFORMATION: Combined DNA/RNA artificial sequence - primer

<400> SEQUENCE: 71
agctgttucc tccttgttgt tagtgaataa aaggttgcc                     39

<210> SEQ ID NO 72
<211> LENGTH: 34
<212> TYPE: DNA
<213> ORGANISM: Artificial Sequence
<220> FEATURE:
<223> OTHER INFORMATION: Combined DNA/RNA artificial sequence - primer

<400> SEQUENCE: 72
atgcgcaaau gaaaacattc ataaattaaa tgtg                          34

<210> SEQ ID NO 73
<211> LENGTH: 41
<212> TYPE: DNA
<213> ORGANISM: Artificial Sequence
<220> FEATURE:
<223> OTHER INFORMATION: Combined DNA/RNA artificial sequence - primer

<400> SEQUENCE: 73
agctgttucc tccttgttcg tttttttacca tttagccata g                 41

<210> SEQ ID NO 74
<211> LENGTH: 31
<212> TYPE: DNA
<213> ORGANISM: Artificial Sequence
<220> FEATURE:
<223> OTHER INFORMATION: Combined DNA/RNA artificial sequence - primer

<400> SEQUENCE: 74
tgcgcaaaug cgtctctctt tctttacaaa c                             31

<210> SEQ ID NO 75
<211> LENGTH: 40
<212> TYPE: DNA
<213> ORGANISM: Artificial Sequence
<220> FEATURE:
<223> OTHER INFORMATION: Combined DNA/RNA artificial sequence - primer

<400> SEQUENCE: 75
agctgttucc tccttgttcg ttaaagctca taaatgttcg                    40

<210> SEQ ID NO 76
<211> LENGTH: 32
<212> TYPE: DNA
<213> ORGANISM: Artificial Sequence
<220> FEATURE:
<223> OTHER INFORMATION: Combined DNA/RNA artificial sequence - primer

<400> SEQUENCE: 76
atgcgcaaau gcggcacgcc ttgcagatta cg                            32

<210> SEQ ID NO 77
<211> LENGTH: 36
<212> TYPE: DNA
<213> ORGANISM: Artificial Sequence
<220> FEATURE:
<223> OTHER INFORMATION: Combined DNA/RNA artificial sequence - primer

<400> SEQUENCE: 77
agctgttucc tccttggtta atgtttgttg tatgcg                        36

<210> SEQ ID NO 78
<211> LENGTH: 34
<212> TYPE: DNA
<213> ORGANISM: Artificial Sequence
<220> FEATURE:
<223> OTHER INFORMATION: Combined DNA/RNA artificial sequence - primer

<400> SEQUENCE: 78
atgcgcaaau ccatttagcc atagtaaaaa catg                                34

<210> SEQ ID NO 79
<211> LENGTH: 38
<212> TYPE: DNA
<213> ORGANISM: Artificial Sequence
<220> FEATURE:
<223> OTHER INFORMATION: Combined DNA/RNA artificial sequence - primer

<400> SEQUENCE: 79
gctgttucct ccttgccgtg gtcttattta tgattaac                            38

<210> SEQ ID NO 80
<211> LENGTH: 30
<212> TYPE: DNA
<213> ORGANISM: Artificial Sequence
<220> FEATURE:
<223> OTHER INFORMATION: Combined DNA/RNA artificial sequence - primer

<400> SEQUENCE: 80
atgcgcaaau gcgcgggttc cgtgcgtggg                                     30

<210> SEQ ID NO 81
<211> LENGTH: 37
<212> TYPE: DNA
<213> ORGANISM: Artificial Sequence
<220> FEATURE:
<223> OTHER INFORMATION: Combined DNA/RNA artificial sequence - primer

<400> SEQUENCE: 81
agctgttucc ccttgattt attactgaaa gggccgc                              37

<210> SEQ ID NO 82
<211> LENGTH: 31
<212> TYPE: DNA
<213> ORGANISM: Artificial Sequence
<220> FEATURE:
<223> OTHER INFORMATION: Combined DNA/RNA artificial sequence - primer

<400> SEQUENCE: 82
atgcgcaaau gtgatcacaa attttaaaca g                                   31

<210> SEQ ID NO 83
<211> LENGTH: 37
<212> TYPE: DNA
<213> ORGANISM: Artificial Sequence
<220> FEATURE:
<223> OTHER INFORMATION: Combined DNA/RNA artificial sequence - primer

<400> SEQUENCE: 83
agctgttucc ccttgacag tgttaccgtt acgatac                              37

<210> SEQ ID NO 84
<211> LENGTH: 32
<212> TYPE: DNA
<213> ORGANISM: Artificial Sequence
<220> FEATURE:
<223> OTHER INFORMATION: Combined DNA/RNA artificial sequence - primer

```
<400> SEQUENCE: 84
atgcgcaaau tgtgagttag ctcactcatt ag                                    32

<210> SEQ ID NO 85
<211> LENGTH: 36
<212> TYPE: DNA
<213> ORGANISM: Artificial Sequence
<220> FEATURE:
<223> OTHER INFORMATION: Combined DNA/RNA artificial sequence - primer

<400> SEQUENCE: 85
agctgttucc tccttgaaat tgttatccgc tcacaa                                36

<210> SEQ ID NO 86
<211> LENGTH: 29
<212> TYPE: DNA
<213> ORGANISM: Artificial Sequence
<220> FEATURE:
<223> OTHER INFORMATION: Combined DNA/RNA artificial sequence - primer

<400> SEQUENCE: 86
atgcgcaaau gaatgctctc aggtgaggg                                        29

<210> SEQ ID NO 87
<211> LENGTH: 36
<212> TYPE: DNA
<213> ORGANISM: Artificial Sequence
<220> FEATURE:
<223> OTHER INFORMATION: Combined DNA/RNA artificial sequence - primer

<400> SEQUENCE: 87
agctgttucc tccttgtttc gcgctccgaa ataatc                                36

<210> SEQ ID NO 88
<211> LENGTH: 34
<212> TYPE: DNA
<213> ORGANISM: Artificial Sequence
<220> FEATURE:
<223> OTHER INFORMATION: Combined DNA/RNA artificial sequence - primer

<400> SEQUENCE: 88
atgcgcaaau ccgaaatcgc tgaaggttac gtac                                  34

<210> SEQ ID NO 89
<211> LENGTH: 41
<212> TYPE: DNA
<213> ORGANISM: Artificial Sequence
<220> FEATURE:
<223> OTHER INFORMATION: Combined DNA/RNA artificial sequence - primer

<400> SEQUENCE: 89
agctgttucc tccttgaatg tgataacggt aacaagttta g                          41

<210> SEQ ID NO 90
<211> LENGTH: 30
<212> TYPE: DNA
<213> ORGANISM: Artificial Sequence
<220> FEATURE:
<223> OTHER INFORMATION: Combined DNA/RNA artificial sequence - primer

<400> SEQUENCE: 90
atgcgcaaau ggctgtgttg aaaggtgttg                                       30

<210> SEQ ID NO 91
<211> LENGTH: 37
```

<212> TYPE: DNA
<213> ORGANISM: Artificial Sequence
<220> FEATURE:
<223> OTHER INFORMATION: Combined DNA/RNA artificial sequence - primer

<400> SEQUENCE: 91
agctgttucc tccttgagta tgggtgcttt ttttacg          37

<210> SEQ ID NO 92
<211> LENGTH: 31
<212> TYPE: DNA
<213> ORGANISM: Artificial Sequence
<220> FEATURE:
<223> OTHER INFORMATION: Combined DNA/RNA artificial sequence - primer

<400> SEQUENCE: 92
atgcgcaaau gaattgcaac agtaatgcca g                31

<210> SEQ ID NO 93
<211> LENGTH: 37
<212> TYPE: DNA
<213> ORGANISM: Artificial Sequence
<220> FEATURE:
<223> OTHER INFORMATION: Combined DNA/RNA artificial sequence - primer

<400> SEQUENCE: 93
agctgttucc tccttgatag gtttagtgtt gtggaac          37

<210> SEQ ID NO 94
<211> LENGTH: 34
<212> TYPE: DNA
<213> ORGANISM: Artificial Sequence
<220> FEATURE:
<223> OTHER INFORMATION: Combined DNA/RNA artificial sequence - primer

<400> SEQUENCE: 94
atgcgcaaau gaaacattc ataaattaaa tgtg              34

<210> SEQ ID NO 95
<211> LENGTH: 93
<212> TYPE: DNA
<213> ORGANISM: Artificial Sequence
<220> FEATURE:
<223> OTHER INFORMATION: Combined DNA/RNA artificial sequence - primer

<400> SEQUENCE: 95
agctgttucc tccttggtta atgtttgttg tatgcgtgaa agtcacggac ctccacgatg    60
cttgtaggca tcgcgcatat tcgctcataa ttc                                93

<210> SEQ ID NO 96
<211> LENGTH: 34
<212> TYPE: DNA
<213> ORGANISM: Artificial Sequence
<220> FEATURE:
<223> OTHER INFORMATION: Combined DNA/RNA artificial sequence - primer

<400> SEQUENCE: 96
atgcgcaaau ccatttagcc atagtaaaaa catg             34

<210> SEQ ID NO 97
<211> LENGTH: 90
<212> TYPE: DNA
<213> ORGANISM: Artificial Sequence
<220> FEATURE:
<223> OTHER INFORMATION: Combined DNA/RNA artificial sequence - primer

```
<400> SEQUENCE: 97
agctgttucc tccttggtta atgtttgttg tatgcgtgaa agtcacggac ctccacgatg    60
cttgtaggca tgccgcgatg ttaagaaaac                                    90

<210> SEQ ID NO 98
<211> LENGTH: 29
<212> TYPE: DNA
<213> ORGANISM: Artificial Sequence
<220> FEATURE:
<223> OTHER INFORMATION: Combined DNA/RNA artificial sequence - primer

<400> SEQUENCE: 98
aaacagcuat gtgcaatagc gataacacc                                     29

<210> SEQ ID NO 99
<211> LENGTH: 36
<212> TYPE: DNA
<213> ORGANISM: Artificial Sequence
<220> FEATURE:
<223> OTHER INFORMATION: Combined DNA/RNA artificial sequence - primer

<400> SEQUENCE: 99
agggttaaut gcgcgttagg cccagaacag aacatc                             36

<210> SEQ ID NO 100
<211> LENGTH: 34
<212> TYPE: DNA
<213> ORGANISM: Artificial Sequence
<220> FEATURE:
<223> OTHER INFORMATION: Combined DNA/RNA artificial sequence - primer

<400> SEQUENCE: 100
attaacccuc caggcatcaa ataaaacgaa aggc                               34

<210> SEQ ID NO 101
<211> LENGTH: 32
<212> TYPE: DNA
<213> ORGANISM: Artificial Sequence
<220> FEATURE:
<223> OTHER INFORMATION: Combined DNA/RNA artificial sequence - primer

<400> SEQUENCE: 101
atttgcgcau caccaatcaa attcacgcgg cc                                 32

<210> SEQ ID NO 102
<211> LENGTH: 32
<212> TYPE: DNA
<213> ORGANISM: Artificial Sequence
<220> FEATURE:
<223> OTHER INFORMATION: Combined DNA/RNA artificial sequence - primer

<400> SEQUENCE: 102
atgcgcaaau gcggcacgcc ttgcagatta cg                                 32

<210> SEQ ID NO 103
<211> LENGTH: 36
<212> TYPE: DNA
<213> ORGANISM: Artificial Sequence
<220> FEATURE:
<223> OTHER INFORMATION: Combined DNA/RNA artificial sequence - primer

<400> SEQUENCE: 103
agctgttucc tccttggtta atgtttgttg tatgcg                             36
```

<210> SEQ ID NO 104
<211> LENGTH: 190
<212> TYPE: DNA
<213> ORGANISM: Artificial Sequence
<220> FEATURE:
<223> OTHER INFORMATION: 190-nucleotide DNA sequence derived from genomic DNA of E. coli (ref. seq ID U00096.3) located upstream the initiation of translation of glpD

<400> SEQUENCE: 104

| | | |
|---|---|---|
| tgcgtctctc tttctttaca aacaagtggg caaatttacc gcacagttta cgtcgaagcg | 60 |
| gcagataaac gccataatgt tatacatatc actctaaaat gttttttcaa tgttacctaa | 120 |
| agcgcgattc tttgctaata tgttcgataa cgaacattta tgagctttaa cgaaagtgaa | 180 |
| tgagggcagc | 190 |

<210> SEQ ID NO 105
<211> LENGTH: 35
<212> TYPE: DNA
<213> ORGANISM: Artificial Sequence
<220> FEATURE:
<223> OTHER INFORMATION: Primer - Combined DNA/RNA sequence

<400> SEQUENCE: 105
aaacagcuat gatctctgtc tacatcatca gtctg          35

<210> SEQ ID NO 106
<211> LENGTH: 38
<212> TYPE: DNA
<213> ORGANISM: Artificial Sequence
<220> FEATURE:
<223> OTHER INFORMATION: Primer - combined DNA/RNA sequence

<400> SEQUENCE: 106
agggttaaut gcgcgttaga cttctttcgg ggttttca       38

<210> SEQ ID NO 107
<211> LENGTH: 32
<212> TYPE: DNA
<213> ORGANISM: Artificial Sequence
<220> FEATURE:
<223> OTHER INFORMATION: Primer - combined DNA/RNA sequence

<400> SEQUENCE: 107
aaacagcuat ggcgttcaaa gtggtccaaa tc             32

<210> SEQ ID NO 108
<211> LENGTH: 39
<212> TYPE: DNA
<213> ORGANISM: Artificial Sequence
<220> FEATURE:
<223> OTHER INFORMATION: Primer - combined DNA/RNA sequence

<400> SEQUENCE: 108
agggttaaut gcgcgttagc ccagcgcgtt atatttctg      39

<210> SEQ ID NO 109
<211> LENGTH: 30
<212> TYPE: DNA
<213> ORGANISM: Artificial Sequence
<220> FEATURE:
<223> OTHER INFORMATION: Primer - combined DNA/RNA sequence

<400> SEQUENCE: 109
aaacagcuat gcaaccgctg gtctccgtgc                30

<210> SEQ ID NO 110
<211> LENGTH: 37
<212> TYPE: DNA
<213> ORGANISM: Artificial Sequence
<220> FEATURE:
<223> OTHER INFORMATION: Primer - combined DNA/RNA sequence

<400> SEQUENCE: 110
agggttaaut gcgcgttaac ggtttttcag caggcgg                              37

<210> SEQ ID NO 111
<211> LENGTH: 34
<212> TYPE: DNA
<213> ORGANISM: Artificial Sequence
<220> FEATURE:
<223> OTHER INFORMATION: Primer - combined DNA/RNA sequence

<400> SEQUENCE: 111
aaacagcuat gtcaaaagtc gctctcatca ccgg                                 34

<210> SEQ ID NO 112
<211> LENGTH: 37
<212> TYPE: DNA
<213> ORGANISM: Artificial Sequence
<220> FEATURE:
<223> OTHER INFORMATION: Primer - combined DNA/RNA sequence

<400> SEQUENCE: 112
agggttaaut gcgcgttact cgttcagcaa cgtcagc                              37

<210> SEQ ID NO 113
<211> LENGTH: 30
<212> TYPE: DNA
<213> ORGANISM: Artificial Sequence
<220> FEATURE:
<223> OTHER INFORMATION: Primer - combined DNA/RNA sequence

<400> SEQUENCE: 113
aaacagcuat gcgtgtcttc gccatttctc                                      30

<210> SEQ ID NO 114
<211> LENGTH: 40
<212> TYPE: DNA
<213> ORGANISM: Artificial Sequence
<220> FEATURE:
<223> OTHER INFORMATION: Primer - combined DNA/RNA sequence

<400> SEQUENCE: 114
agggttaaut gcgcgttaga cgaattgcca gtatttcagg                           40

<210> SEQ ID NO 115
<211> LENGTH: 33
<212> TYPE: DNA
<213> ORGANISM: Artificial Sequence
<220> FEATURE:
<223> OTHER INFORMATION: Primer - combined DNA/RNA sequence

<400> SEQUENCE: 115
aaacagcuat ggaacgtaac gccgtgagcc tgc                                  33

<210> SEQ ID NO 116
<211> LENGTH: 39
<212> TYPE: DNA
<213> ORGANISM: Artificial Sequence
<220> FEATURE:
<223> OTHER INFORMATION: Primer - combined DNA/RNA sequence

```
<400> SEQUENCE: 116
agggttaaut gcggcttagt ttttatcgtc aaaggtcag                                    39

<210> SEQ ID NO 117
<211> LENGTH: 36
<212> TYPE: DNA
<213> ORGANISM: Artificial Sequence
<220> FEATURE:
<223> OTHER INFORMATION: Primer - combined DNA/RNA sequence

<400> SEQUENCE: 117
agctgttucc tccttaggta cccagctttt gttccc                                       36
```